US008613924B2

(12) United States Patent
Yokoseki et al.

(10) Patent No.: US 8,613,924 B2
(45) Date of Patent: Dec. 24, 2013

(54) ANTIBODIES THAT SPECIFICALLY BIND TO A BETA OLIGOMERS AND USE THEREOF

(75) Inventors: Tatsuki Yokoseki, Kanagawa (JP); Yasuhide Okamoto, Kanagawa (JP); Makoto Umeda, Kanagawa (JP); Naofumi Takamatsu, Kanagawa (JP); Toshiyuki Ito, Kanagawa (JP); Yukiho Imai, Kanagawa (JP); Shinobu Fujii, Kanagawa (JP)

(73) Assignee: Immunas Pharma, Inc., Kawasaki-shi, Kanagawa (JP)

( * ) Notice: Subject to any disclaimer, the term of this patent is extended or adjusted under 35 U.S.C. 154(b) by 0 days.

(21) Appl. No.: 13/389,228

(22) PCT Filed: Aug. 5, 2010

(86) PCT No.: PCT/JP2010/004926
§ 371 (c)(1),
(2), (4) Date: Feb. 6, 2012

(87) PCT Pub. No.: WO2011/016239
PCT Pub. Date: Feb. 10, 2011

(65) Prior Publication Data
US 2012/0156193 A1    Jun. 21, 2012

Related U.S. Application Data

(60) Provisional application No. 61/231,797, filed on Aug. 6, 2009, provisional application No. 61/282,550, filed on Feb. 26, 2010.

(51) Int. Cl.
*A61K 39/395* (2006.01)
*G01N 33/53* (2006.01)
*C07K 16/18* (2006.01)
*C12P 21/08* (2006.01)

(52) U.S. Cl.
USPC ... 424/141.1; 424/133.1; 435/7.1; 530/387.3; 530/388.25; 530/388.1

(58) Field of Classification Search
None
See application file for complete search history.

(56) References Cited

U.S. PATENT DOCUMENTS

| | | | |
|---|---|---|---|
| 6,218,506 B1 | 4/2001 | Krafft et al. |
| 6,706,487 B1 | 3/2004 | Abdel-Meguid et al. |
| 7,339,035 B2 | 3/2008 | Yanagisawa et al. |
| 7,638,283 B2 | 12/2009 | Krafft et al. |
| 7,741,448 B2 | 6/2010 | Yanagisawa et al. |
| 8,378,081 B2 | 2/2013 | Matsubara et al. |
| 2003/0068316 A1 | 4/2003 | Klein et al. |
| 2006/0228349 A1 | 10/2006 | Acton et al. |
| 2006/0257396 A1 | 11/2006 | Jacobsen |
| 2007/0098721 A1 | 5/2007 | Hillen et al. |
| 2007/0218499 A1 | 9/2007 | Lambert et al. |
| 2010/0028357 A1 | 2/2010 | Matsubara et al. |
| 2010/0183611 A1 | 7/2010 | Imboden et al. |
| 2010/0260783 A1 | 10/2010 | Matsubara et al. |
| 2010/0291071 A1 | 11/2010 | Matsubara et al. |
| 2011/0097319 A1 | 4/2011 | Matsubara et al. |
| 2012/0082667 A1 | 4/2012 | Yokoseki et al. |
| 2012/0141477 A1 | 6/2012 | Matsubara et al. |
| 2012/0177664 A1 | 7/2012 | Yokoseki et al. |

FOREIGN PATENT DOCUMENTS

| | | |
|---|---|---|
| JP | 3512815 B2 | 1/2004 |
| JP | 2008-527005 A | 7/2008 |
| WO | WO 00/56771 A1 | 9/2000 |
| WO | WO 03/004056 A1 | 1/2003 |
| WO | WO 03/014162 A1 | 2/2003 |
| WO | WO 03/104437 A2 | 12/2003 |
| WO | WO 2006/047254 A1 | 5/2006 |
| WO | WO 2006/055178 A2 | 5/2006 |
| WO | WO 2006077471 A2 * | 7/2006 |
| WO | WO 2006/083533 A2 | 8/2006 |
| WO | WO 2006/094724 A2 | 9/2006 |
| WO | WO 2006/137354 A1 | 12/2006 |
| WO | WO 2007/010040 A1 | 1/2007 |
| WO | WO 2007108756 A1 * | 9/2007 |
| WO | WO 2008/150946 A1 | 12/2008 |
| WO | WO 2009/051220 A1 | 4/2009 |
| WO | WO 2009/099176 A1 | 8/2009 |
| WO | WO 2010/012004 A2 | 1/2010 |

OTHER PUBLICATIONS

Novotny J et al. (1983) Amino acid sequence of the light chain variable region from a mouse anti-digoxin hybridoma antibody. Biochemistry, 22(5):1153-1158; Abstract only.*
Kayed, R. and Glabe, C.G., "Conformation-Dependent Anti-Amyloid Oligomer Antibodies," *Methods Enzymol.* 413:326-344, Elsevier Inc. (2006).
Klein, W.L., "Aβ toxicity in Alzheimer's disease: globular oligomers (ADDLs) as new vaccine and drug targets," *Neurochemistry International* 41:345-352, Elsevier Science Ltd. (2002).
Casset, F., et al., "A peptide mimetic of an anti-CD4 monoclonal antibody by rational design," *Biochem. Biophys. Res. Commun.* 307:198-205, Elsevier Science, United States (2003).
MacCallum, R.M., et al. "Antibody-antigen Interactions: Contact Analysis and Binding Site Topography," *J. Mol. Biol.* 262:732-745, Academic Press Limited, Netherlands (1996).
Padlan, E.A., et al., "Structure of an antibody—antigen complex: Crystal structure of the HyHEL-10 Fab—lysozyme complex," *Proc. Natl. Acad. Sci. USA* 86:5938-5942, National Academy of Science, United States (Aug. 1989).
Paul, W.E., ed., *Fundamental Immunology, Third Edition*, pp. 292-295, Raven Press, Ltd., New York, United States (1993).

(Continued)

*Primary Examiner* — Kimberly A Ballard
(74) *Attorney, Agent, or Firm* — Sterne, Kessler, Goldstein & Fox P.L.L.C.

(57) ABSTRACT

The present inventors successfully produced monoclonal antibodies that are specific to only soluble A beta oligomers, but do not recognize soluble A beta monomers, which are physiological molecules. It was demonstrated that the antibodies are useful as diagnostic/therapeutic monoclonal antibodies for Alzheimer's disease.

13 Claims, 7 Drawing Sheets

(56) References Cited

OTHER PUBLICATIONS

Rudikoff, S., et al. "Single amino acid substitution altering antigen-binding specificity," *Proc. Natl. Acad. Sci. USA* 79:1979-1983, National Academy of Science, United States (Mar. 1982).

Terryberry, J.W., et al., "Autoantibodies in Neurodegenerative Diseases: Antigen-Specific Frequencies and Intrathecal Analysis," *Neurobiol. Aging* 19(3):205-216, Elsevier Science Inc., United States (1998).

Vajdos, F. F., et al. "Comprehensive Functional Maps of the Antigen-binding Site of an Anti-ErbB2 Antibody Obtained with Shotgun Scanning Mutagenesis," *J. Mol. Biol.* 320:415-428, Elsevier Science Ltd., United States (2002).

International Search Report for International Application No. PCT/JP2010/004926, Japan Patent Office, Japan, mailed on Oct. 26, 2010.

Co-pending, U.S. Appl. No. 13/369,807, inventors Matsubara, E., et al., filed Feb. 9, 2012 (Not Yet Published).

Office Action mailed Apr. 12, 2011, in U.S. Appl. No. 12/533,348, inventors Matsubara, E., et al., filed Jul. 31, 2009, U.S. Patent and Trademark Office, Alexandria, VA.

Haass, C., et al., "Soluble protein oligomers in neurodegeneration: lessons from the Alzheimer's amyloid β-peptide," *Nat. Rev. Mol. Cell Bio.* 8:101-112, Nature Publishing Group, England (2007).

Kayed, R., et al., "Common Structure of Soluble Amyloid Oligomers Implies Common Mechanism of Pathogenesis," *Science* 300:486-489, American Association for the Advancement of Science, United States (2003).

Kayed, R., et al., "Fibril specific, conformation dependent antibodies recognize a generic epitope common to amyloid fibrils and fibrillar oligomers that is absent in prefibrillar oligomers," *Mol. Neurodegener.* 2:18, BioMed Central Ltd., England (2007).

Klein, W. L., et al., "Targeting small Aβ oligomers: the solution to an Alzheimer's disease conundrum?" *Trends Neurosci.* 24(4):219-224, Elsevier Inc., England (2001).

Lambert, M. P., et al., "Vaccination with soluble Aβ oligomers generates toxicity-neutralizing antibodies," *J. Neurochem.* 79:595-605, International Society for Neurochemisty, England (2001).

Lambert, M. P., et al., "Monoclonal antibodies that target pathological assemblies of Aβ," *J. Neurochem.* 100:23-35, International Society for Neurochemistry, England (2007).

Lee, E. B., et al., "Targeting Amyloid-β Peptide (Aβ) Oligomers by Passive Immunization with a Conformation-selective Monoclonal Antibody Improves Learning and Memory in Aβ Precursor Protein (APP) Transgenic Mice," *J. Biol. Chem.* 281:4292-4299, American Society for Biochemistry and Molecular Biology, United States (2006).

Lesné, S., et al., "A specific amyloid-β protein assembly in the brain impairs memory," *Nature* 440:352-357, nature Publishing Group, England (2006).

Matsubara, E., et al., "Development of a diagnosing system for Alzheimer's disease using anti-Aβ oligomer antibodies," Abstract 1-2-9, The 46th Annual Meeting of Japanese Society of Neurology, Kagoshima, Japan, May 25-27, 2005.

Matsubara, Etsuro, "Aβ oligomers," *Dementia Japan* 21:253-259, Japan (2007).

Matsubara, Etsuro, "Immunotherapy targeting Aβ oligomers for Alzheimer's disease," Abstract S31-2 and presentation, 8th Asia/Oceania Regional Congress of Gerontology and Geriatrics, Beijing, China, Oct. 22, 2007.

Matsubara, Etsuro, "Passive immunotherapy Aβ oligomer in Alzheimer's disease," Abstract S38-4, 128th Annual Meeting of the Pharmaceutical Society of Japan, Yokohama, Japan, Mar. 26-28, 2008.

Matsubara, Etsuro, "The Aβ-oligomer specific passive immunization in Alzheimer's disease," 128th Annual Meeting of the Pharmaceutical Society of Japan, Yokohama, Japan, Feb. 1, 2007.

Matsubara, Etsuro, "Neurotoxic Aβ oligomer being the basis of developmental pathology of Alzheimer's disease," Abstract SY-2-2, The 49th Annual Meeting of Japanese Society of Neurology, Yokohama, Japan, Apr. 25, 2008.

Matsubara, Etsuro, "The Aβ-oligomer specific passive immunization in Alzheimer's disease," The 49th Annual Meeting of Japanese Society of Neurology, Yokohama, Japan, May 16, 2008.

Moretto, N., et al., "Conformation-sensitive Antibodies against Alzheimer Amyloid-β by Immunization with a Thioredoxin-constrained B-cell Epitope Peptide," *J. Biol. Chem.* 282:11436-11445, American Society for Biochemistry and Molecular Biology, United States (2007).

Selkoe, Dennis J., "Alzheimer's Disease is a Synaptic Failure," *Science* 298:789-791, American Association for the Advancement of Science, United States (2002).

Shoji, M., et al., "Investigation pathogenicity of Aβ peptide and development of pathogenic Aβ oligomer removal therapy," Health and Labour Sciences ResearchA Grants (Research on specified diseases), pp. 68-72 (2004).

Shoji, M., et al., "Antibody therapy for Alzheimer's disease," Health and Labour Sciences Research Grants, Study and research group on amyloidosis, pp. 76-78 (2008).

Sun, H., et al., "Characterization of therapeutic antibody against Aβ oligomers for Alzheimers disease," *Dementia Japan* 21:183, Abstract p. 2-261, Japan (2007).

Sun, H., et al., "Characterization of therapeutic antibody against Aβ oligomers for Alzheimer's disease," The 26th Annual Meeting of Japan Society for Dementia Research, Oct. 17-18, 2007.

Sun, H., et al., "Characterization of therapeutic antibody against Aβ oligomers for Alzheimer's disease," Abstract, Neuroscience 2007, San Diego, United States, Aug. 16, 2007.

Sun, H., et al., "Characterization of therapeutic antibody against Aβ oligomers for Alzheimer's disease," Poster 485.15/W10, Neuroscience 2007, San Diego, United States, Nov. 5, 2007.

Unverified English language translation of Matsubara, E., et al., "Development of a diagnosing system for Alzheimer' disease using anti-Aβ oligomer antibodies," Abstract 1-2-9, The 46th Annual Meeting of Japanese Society of Neurology, Kagoshima, Japan, May 25-27, 2005.

Unverified English language translation of Abstract of Matsubara, Etsuro, "Aβ oligomers," *Dementia Japan* 21:253-259, Japan (2007).

Unverified English language translation of Matsubara, Etsuro, "Passive immunotherapy Aβ oligomer in Alzheimer's disease," Abstract S38-4, 128th Annual Meeting of the Pharmaceutical Society of Japan, Yokohama, Japan, Mar. 26-28, 2008.

Unverified English language translation of Matsubara, Etsuro, "The Aβ-oligomer specific passive immunization in Alzheimer's disease," 128th Annual Meeting of thw Pharmaceutical Society of Japan, Yokohama, Japan, Mar. 28, 2008.

Unverified English language translation of Matsubara, Etsuro, "Neurotoxic Aβ oligomer being the basis of developmental pathology of Alzheimer's disease," Abstract SY-2-2, The 49th Annual Meeting of Japanese Society of Neurology, Yokohama, Japan, May 15-17, 2008.

Unverified English language translation of Matsubara, Etsuro, "The Aβ-oligomer specific passive immunization in Alzheimer's disease," The 49th Annual Meeting of Japanese Society of Neurology, Yokohama, Japan, May 16, 2008.

Unverified English language translation of Shoji, M., et al., "Investigation on pathogenicity of Aβ peptide and development of pathogenic Aβ oligomer removal therapy," Health and Labour Sciences ResearchA Grants (Research on specified diseases), pp. 68-72 (2004).

Unverified English language translation of Shoji, M., et al., "Antibody therapy for Alzheimer's disease," Health and Labour Sciences Research Grants, Study and research group on amyloidosis, pp. 76-78 (2008).

Office Action mailed Apr. 13, 2011, in U.S. Appl. No. 12/533,294, inventors Matsubara, E., et al., filed Jul. 31, 2009, U.S. Patent and Trademark Office, Alexandria, VA.

Office Action mailed Jan. 19, 2012, in U.S. Appl. No. 12/762,878, inventors Matsubara, E., et al., filed Apr. 19, 2010, U.S. Patent and Trademark Office, Alexandria, VA.

(56) References Cited

OTHER PUBLICATIONS

Co-pending, U.S. Appl. No. 13/389,229, et al., inventors Yokoseki, T., et al., Int'l Filing Date: Aug. 5, 2010 (Not Yet Published).

Brookmeyer, R. et al., "Forecasting the global burden of Alzheimer's disease," *Alzheimer's & Dementia* 3:186-191, The Alzheimer's Association (2007).

Ma, Q.-L. et al., "Antibodies Against β-Amyloid Reduce Aβ Oligomers, Glycogen Synthase Kinase-3β Activation and τ Phosphorylation In Vivo and In Vitro," *J. Neurosci. Res.* 83:374-384, Wiley-Liss, Inc. (2006).

Wang, X.-p. et al., "Conformation-dependent single-chain variable fragment antibodies specifically recognize beta-amyloid oligomers," *FEBS Letts.* 583:579-584, Elsevier B.V. (2009).

Co-pending, U.S. Appl. No. 13/760,936, inventors Matsubara, E., et al., filed Feb. 6, 2013 (Not Yet Published).

Bussière, T. et al., "Animal Model: Morphological Characterization of Thioflavin-S-Positive Amyloid Plaques in Transgenic Alzheimer Mice and Effect of Passive Aβ Immunotherapy on Their Clearance," *Am. J. Pathol.* 165:987-995, American Society for Investigative Pathology (2004).

Querfurth, H.W. and LaFerla, F.M., "Mechanisms of Disease: Alzheimer's Disease," *N. Engl. J Med.* 362:329-344, Massachusetts Medical Society (2010).

Office Action mailed Aug. 29, 2012, in U.S. Appl. No. 12/762,878, inventor Matsubara, E., et al., filed Apr. 19, 2010, U.S. Patent and Trademark Office, Alexandria, VA.

\* cited by examiner

Fig. 5
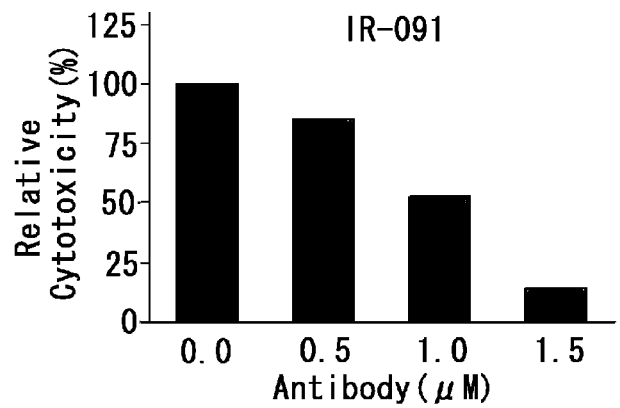
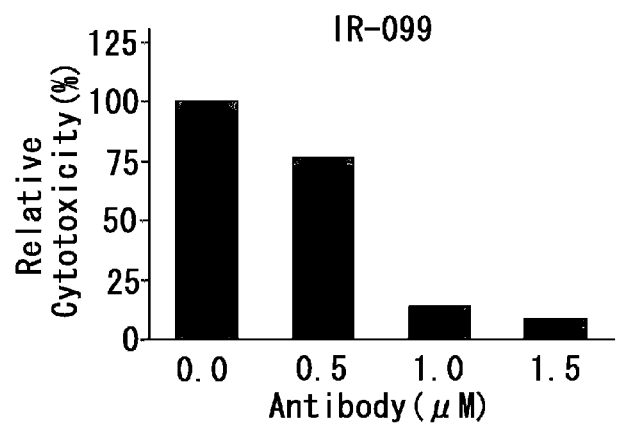
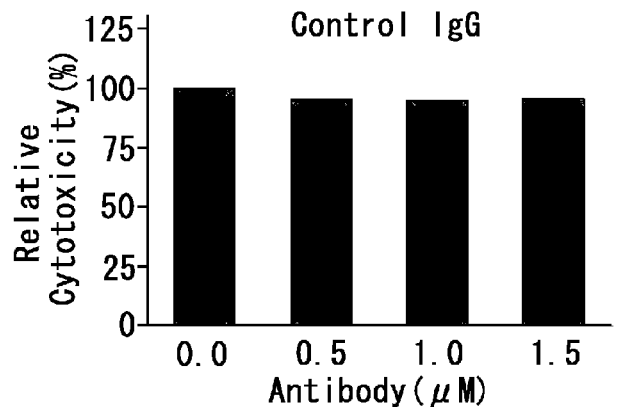

Fig. 6
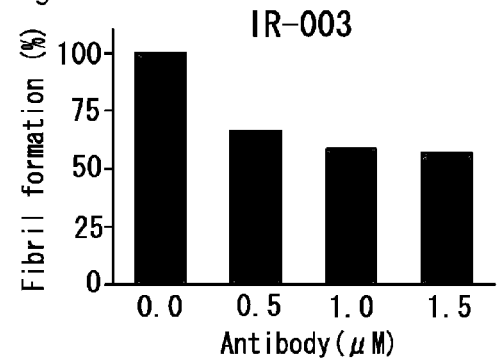
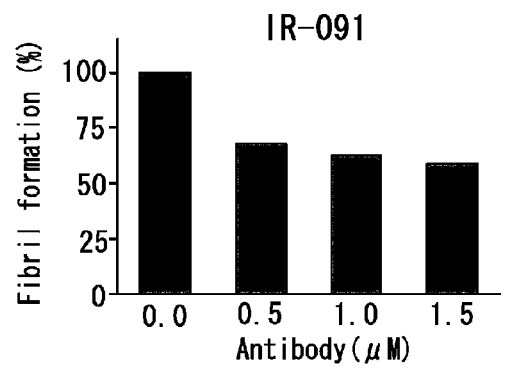
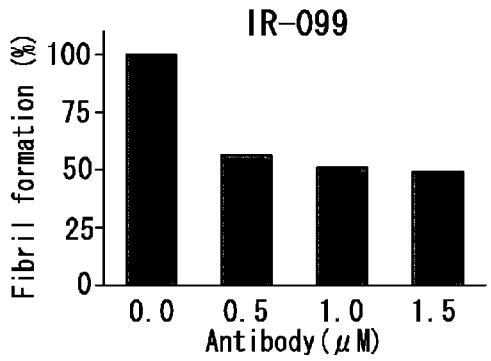
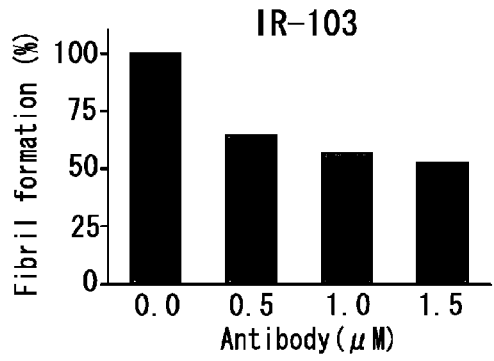
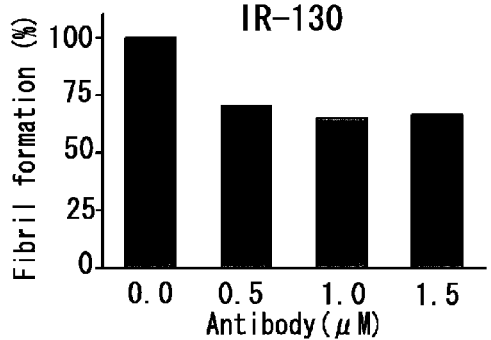
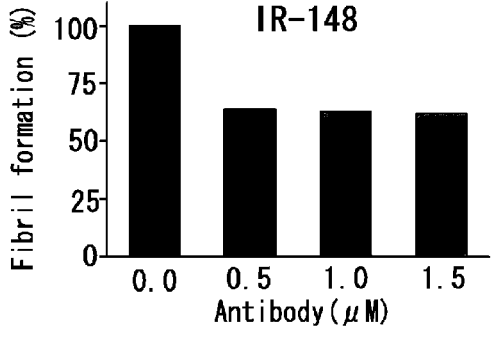
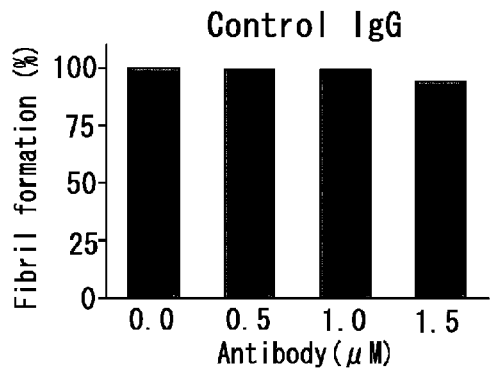

ANTIBODIES THAT SPECIFICALLY BIND TO A BETA OLIGOMERS AND USE THEREOF

PRIORITY

The present application claims the benefit of U.S. Provisional Application No. 61/231,797, filed on Aug. 6, 2009, and U.S. Provisional Application No. 61/282,550, filed on Feb. 26, 2010, the entire contents of which are incorporated by reference herein.

REFERENCE TO SEQUENCE LISTING SUBMITTED ELECTRONICALLY

The content of the electronically submitted sequence listing, file name: 21440480002 sequencelstg.txt; Size: 56,393 bytes; Date of Creation: Feb. 28, 2012, filed herewith, is incorporated herein by reference in its entirety.

TECHNICAL FIELD

1. Technical Field

The present invention relates to antibodies that specifically bind to A beta oligomers and uses thereof.

2. Background Art

The number of Alzheimer's disease (AD) patients is more than about 26 million worldwide in 2006, and it is predicted to continue increasing in an aging society (Non-Patent Literature (NPL) 1). However, there is no curative therapeutic agent that arrests or reverses the progression of Alzheimer's disease, although therapeutic agents that retard the progression of the disease are commercially available.

Various evidence has shown that deterioration of memory arises from synaptic dysfunction triggered by soluble amyloid beta (A beta) oligomers (see Non-Patent Literatures 2 and 3). Excessive accumulation and deposition of A beta oligomers may be the trigger for a series of pathological cascades that lead to Alzheimer's disease. Therefore, therapeutic intervention targeting A beta oligomers may be effective for blocking these cascades (see Non-Patent Literatures 4 and 5).

Recently, antibody pharmaceuticals that target A beta are being developed. However, previously-reported anti-A beta oligomer antibodies do not specifically bind to A beta oligomers, but bind to all of the three forms, i.e., A beta monomers, oligomers, and fibrils. Thus, even if they are administered in vivo, it is thought that the amount of antibodies that bind to A beta oligomers would be relatively low, and the dosage may need to be increased to obtain effect. Moreover, since A beta monomers are present in the brain of healthy individuals, side effects may be cause by the binding of the antibodies to A beta monomers.

Furthermore, the amount of A beta oligomer could be an index of Alzheimer's disease; however, it was difficult to measure A beta oligomers alone using conventional anti-A beta antibodies.

Prior art information related to the present invention is shown below.

CITATION LIST

Non Patent Literature

NPL 1: Brookmeyer R et al., Alzheimers Dement. July; 3(3): 186-91, 2007
NPL 2: Klein W L, Trends Neurosci. 24: 219-224, 2001
NPL 3: Selkoe D J, Science 298: 789-791, 2002
NPL 4: Haass C et al.: Nat Rev Mol Cell Biol. 8: 101-12, 2007
NPL 5: Lee E B, et al.: J. Biol. Chem. 281: 4292-4299, 2006

SUMMARY OF INVENTION

Technical Problem

The present invention was achieved in view of the above circumstances. An objective of the present invention is to provide antibodies that bind specifically to A beta oligomers, and uses thereof. More specifically, the present invention provides antibodies that bind specifically to A beta oligomers, methods for detecting A beta oligomers using the antibodies, methods for diagnosing Alzheimer's disease using the antibodies, pharmaceutical compositions and agents comprising the antibodies, agents and kits for detecting A beta oligomers, and agents and kits for diagnosing Alzheimer's disease.

Solution to Problem

The present inventors successfully produced multiple monoclonal antibodies that are specific to only soluble amyloid beta (A beta) oligomers and do not recognize soluble A beta monomers which are physiological molecules, using an isolated A beta tetramer as an antigen.

Thus, the present inventors disclose that the multiple antibodies are promising candidates for therapeutic antibodies for treating/preventing Alzheimer's disease, or for diagnostic antibodies for diagnosing Alzheimer's disease.

More specifically, the present invention provides the following:

[1] An antibody that recognizes an isolated A beta oligomer as an antigen, wherein the antibody does not bind to an A beta monomer.

[2] The antibody of [1], which is any one of (1) to (12) below:

(1) an antibody that comprises an H chain having CDR1, CDR2, and CDR3, which are identified in VH comprising the amino acid sequence of SEQ ID NO: 98;

(2) an antibody that comprises an L chain having CDR1, CDR2, and CDR3, which are identified in VL comprising the amino acid sequence of SEQ ID NO: 100;

(3) an antibody that comprises an H chain having CDR1, CDR2, and CDR3, which are identified in VH comprising the amino acid sequence of SEQ ID NO: 102;

(4) an antibody that comprises an L chain having CDR1, CDR2, and CDR3, which are identified in VL comprising the amino acid sequence of SEQ ID NO: 104;

(5) an antibody that comprises an H chain having CDR1, CDR2, and CDR3, which are identified in VH comprising the amino acid sequence of SEQ ID NO: 106;

(6) an antibody that comprises an L chain having CDR1, CDR2, and CDR3, which are identified in VL comprising the amino acid sequence of SEQ ID NO: 108;

(7) an antibody that comprises an H chain having CDR1, CDR2, and CDR3, which are identified in VH comprising the amino acid sequence of SEQ ID NO: 110;

(8) an antibody that comprises an L chain having CDR1, CDR2, and CDR3, which are identified in VL comprising the amino acid sequence of SEQ ID NO: 112;

(9) an antibody that comprises an H chain having CDR1, CDR2, and CDR3, which are identified in VH comprising the amino acid sequence of SEQ ID NO: 114;

(10) an antibody that comprises an L chain having CDR1, CDR2, and CDR3, which are identified in VL comprising the amino acid sequence of SEQ ID NO: 116;

(11) an antibody that comprises an H chain having CDR1, CDR2, and CDR3, which are identified in VH comprising the amino acid sequence of SEQ ID NO: 118;

(12) an antibody that comprises an L chain having CDR1, CDR2, and CDR3, which are identified in VL comprising the amino acid sequence of SEQ ID NO: 120.

[3] The antibody of [1], which is any one of (1) to (38) below:

(1) an antibody that comprises an H chain having the amino acid sequence of SEQ ID NO: 6 as CDR1, the amino acid sequence of SEQ ID NO: 8 as CDR2, and the amino acid sequence of SEQ ID NO: 10 as CDR3;

(2) an antibody that comprises an L chain having the amino acid sequence of SEQ ID NO: 12 as CDR1, the amino acid sequence of SEQ ID NO: 14 as CDR2, and the amino acid sequence of SEQ ID NO: 16 as CDR3;

(3) an antibody that comprises the H chain of (1) and the L chain of (2);

(4) an antibody that comprises an H chain having the amino acid sequence of SEQ ID NO: 98 as VH;

(5) an antibody that comprises an L chain having the amino acid sequence of SEQ ID NO: 100 as VL;

(6) an antibody that comprises the H chain of (4) and the L chain of (5);

(7) an antibody that comprises an H chain having the amino acid sequence of SEQ ID NO: 22 as CDR1, the amino acid sequence of SEQ ID NO: 24 as CDR2, and the amino acid sequence of SEQ ID NO: 26 as CDR3;

(8) an antibody that comprises an L chain having the amino acid sequence of SEQ ID NO: 28 as CDR1, the amino acid sequence of SEQ ID NO: 30 as CDR2, and the amino acid sequence of SEQ ID NO: 32 as CDR3;

(9) an antibody that comprises the H chain of (7) and the L chain of (8);

(10) an antibody that comprises an H chain having the amino acid sequence of SEQ ID NO: 102 as VH;

(11) an antibody that comprises an L chain having the amino acid sequence of SEQ ID NO: 104 as VL;

(12) an antibody that comprises the H chain of (10) and the L chain of (11);

(13) an antibody that comprises an H chain having the amino acid sequence of SEQ ID NO: 38 as CDR1, the amino acid sequence of SEQ ID NO: 40 as CDR2, and the amino acid sequence of SEQ ID NO: 42 as CDR3;

(14) an antibody that comprises an L chain having the amino acid sequence of SEQ ID NO: 44 as CDR1, the amino acid sequence of SEQ ID NO: 46 as CDR2, and the amino acid sequence of SEQ ID NO: 48 as CDR3;

(15) an antibody that comprises the H chain of (13) and the L chain of (14);

(16) an antibody that comprises an H chain having the amino acid sequence of SEQ ID NO: 106 as VH;

(17) an antibody that comprises an L chain having the amino acid sequence of SEQ ID NO: 108 as VL;

(18) an antibody that comprises the H chain of (16) and the L chain of (17);

(19) an antibody that comprises an H chain having the amino acid sequence of SEQ ID NO: 54 as CDR1, the amino acid sequence of SEQ ID NO: 56 as CDR2, and the amino acid sequence of SEQ ID NO: 58 as CDR3;

(20) an antibody that comprises an L chain having the amino acid sequence of SEQ ID NO: 60 as CDR1, the amino acid sequence of SEQ ID NO: 62 as CDR2, and the amino acid sequence of SEQ ID NO: 64 as CDR3;

(21) an antibody that comprises the H chain of (19) and the L chain of (20);

(22) an antibody that comprises an H chain having the amino acid sequence of SEQ ID NO: 110 as VH;

(23) an antibody that comprises an L chain having the amino acid sequence of SEQ ID NO: 112 as VL; (24) an antibody that comprises the H chain of (22) and the L chain of (23);

(25) an antibody that comprises an H chain having the amino acid sequence of SEQ ID NO: 70 as CDR1, the amino acid sequence of SEQ ID NO: 72 as CDR2, and the amino acid sequence of SEQ ID NO: 74 as CDR3;

(26) an antibody that comprises an L chain having the amino acid sequence of SEQ ID NO: 76 as CDR1, the amino acid sequence of SEQ ID NO: 78 as CDR2, and the amino acid sequence of SEQ ID NO: 80 as CDR3;

(27) an antibody that comprises the H chain of (25) and the L chain of (26);

(28) an antibody that comprises an H chain having the amino acid sequence of SEQ ID NO: 114 as VH;

(29) an antibody that comprises an L chain having the amino acid sequence of SEQ ID NO: 116 as VL;

(30) an antibody that comprises the H chain of (28) and the L chain of (29);

(31) an antibody that comprises an H chain having the amino acid sequence of SEQ ID NO: 86 as CDR1, the amino acid sequence of SEQ ID NO: 88 as CDR2, and the amino acid sequence of SEQ ID NO: 90 as CDR3;

(32) an antibody that comprises an L chain having the amino acid sequence of SEQ ID NO: 92 as CDR1, the amino acid sequence of SEQ ID NO: 94 as CDR2, and the amino acid sequence of SEQ ID NO: 96 as CDR3;

(33) an antibody that comprises the H chain of (31) and the L chain of (32);

(34) an antibody that comprises an H chain having the amino acid sequence of SEQ ID NO: 118 as VH;

(35) an antibody that comprises an L chain having the amino acid sequence of SEQ ID NO: 120 as VL;

(36) an antibody that comprises the H chain of (34) and the L chain of (35);

(37) an antibody that comprises one or more amino acid substitutions, deletions, additions, and/or insertions in the antibody of any one of (1) to (36), which has equivalent activity to the antibody of any one of (1) to (36); and

(38) an antibody that binds to the epitope bound by the antibody of any one of (1) to (36).

[4] The antibody of any one of [1] to [3], wherein the antibody is a chimeric antibody or a humanized antibody.

[5] An antigen-binding fragment of the antibody of any one of [1] to [4].

[6] A pharmaceutical composition comprising the antibody of any one of [1] to [4] or the antigen-binding fragment of [5], and a pharmaceutically acceptable carrier.

[7] The composition of [6], which is an agent against cognitive impairment, a therapeutic agent for Alzheimer's disease, an agent for suppressing the progression of Alzheimer's disease, an agent for suppressing senile plaque formation, an agent for suppressing A beta accumulation, an anti-neurotoxic agent, an agent for inhibiting A beta amyloid fibril formation, or an agent against synaptic toxicity.

[8] A method for detecting an A beta oligomer, which comprises the step of detecting an A beta oligomer contained in a sample using the antibody of any one of [1] to [4] or the antigen-binding fragment of [5].

[9] A method of diagnosing whether or not a subject is a possible Alzheimer's disease patient, which comprises using the antibody of any one of [1] to [4] or the antigen-binding fragment of [5], to detect an A beta oligomer in a sample collected from a subject.

[10] A method of diagnosing whether or not a subject is a possible Alzheimer's disease patient, which comprises the steps of:
(a) contacting a sample collected from a subject with the antibody of any one of [1] to
[4] or the antigen-binding fragment of [5]; and
(b) measuring the amount of A beta oligomer in the sample, wherein the subject is determined to be a possible Alzheimer's disease patient, when the amount measured in step (b) is higher than that of a healthy individual.

[11] A method of diagnosing whether or not a subject is a possible Alzheimer's disease patient, which comprises the steps of:
(a) contacting a sample collected from a subject with the antibody of any one of [1] to
[4] or the antigen-binding fragment of [5], and an antibody that binds to an A beta monomer; and
(b) measuring the ratio of A beta oligomer to A beta monomer in the sample,
wherein the subject is determined to be a possible Alzheimer's disease patient, when the ratio measured in step (b) is higher than that of a healthy individual.

[12] The method of any one of [8] to [11], wherein the sample is blood or cerebrospinal fluid.

[13] An agent for use in the method of any one of [8] to [12].

[14] A kit for use in the method of any one of [8] to [12].

Furthermore, the present invention provides the following:

[15] Use of the antibody of any one of [1] to [4] or the antigen-binding fragment of [5] for the manufacture of an agent against cognitive impairment, a therapeutic agent for Alzheimer's disease, an agent for suppressing the progression of Alzheimer's disease, an agent for suppressing senile plaque formation, an agent for suppressing A beta accumulation, an anti-neurotoxic agent, an agent for inhibiting A beta amyloid fibril formation, or an agent against synaptic toxicity.

[16] The antibody of any one of [1] to [4] or the antigen-binding fragment of [5] for use in preventing and/or treating cognitive impairment.

[17] The antibody of any one of [1] to [4] or the antigen-binding fragment of [5] for use in preventing and/or treating Alzheimer's disease.

[18] The antibody of any one of [1] to [4] or the antigen-binding fragment of [5] for use in suppressing the progression of Alzheimer's disease.

[19] The antibody of any one of [1] to [4] or the antigen-binding fragment of [5] for use in suppressing senile plaque formation.

[20] The antibody of any one of [1] to [4] or the antigen-binding fragment of [5] for use in suppressing A beta accumulation.

[21] The antibody of any one of [1] to [4] or the antigen-binding fragment of [5] for use in neutralizing (suppressing) neurotoxicity.

[22] The antibody of any one of [1] to [4] or the antigen-binding fragment of [5] for use in inhibiting A beta amyloid fibril formation.

[23] The antibody of any one of [1] to [4] or the antigen-binding fragment of [5] for use in neutralizing (suppressing) synaptic toxicity.

[24] A method for preventing and/or treating cognitive impairment, which comprises the step of administering a therapeutically effective amount of the antibody of any one of [1] to [4] or the antigen-binding fragment of [5].

[25] A method for preventing and/or treating Alzheimer's disease, which comprises the step of administering a therapeutically effective amount of the antibody of any one of [1] to [4] or the antigen-binding fragment of [5].

[26] A method for suppressing the progression of Alzheimer's disease, which comprises the step of administering a therapeutically effective amount of the antibody of any one of [1] to [4] or the antigen-binding fragment of [5].

[27] A method for suppressing senile plaque formation, which comprises the step of administering a therapeutically effective amount of the antibody of any one of [1] to [4] or the antigen-binding fragment of [5].

[28] A method for suppressing A beta accumulation, which comprises the step of administering a therapeutically effective amount of the antibody of any one of [1] to [4] or the antigen-binding fragment of [5].

[29] A method for neutralizing neurotoxicity, which comprises the step of administering a therapeutically effective amount of the antibody of any one of [1] to [4] or the antigen-binding fragment of [5].

[30] A method for inhibiting A beta amyloid fibril formation, which comprises the step of administering a therapeutically effective amount of the antibody of any one of [1] to [4] or the antigen-binding fragment of [5].

[31] A method for neutralizing synaptic toxicity, which comprises the step of administering a therapeutically effective amount of the antibody of any one of [1] to [4] or the antigen-binding fragment of [5].

[32] Use of the antibody of any one of [1] to [4] or the antigen-binding fragment of [5] for preventing and/or treating cognitive impairment.

[33] Use of the antibody of any one of [1] to [4] or the antigen-binding fragment of [5] for preventing and/or treating Alzheimer's disease.

[34] Use of the antibody of any one of [1] to [4] or the antigen-binding fragment of [5] for suppressing the progression of Alzheimer's disease.

[35] Use of the antibody of any one of [1] to [4] or the antigen-binding fragment of [5] for suppressing senile plaque formation.

[36] Use of the antibody of any one of [1] to [4] or the antigen-binding fragment of [5] for suppressing A beta accumulation.

[37] Use of the antibody of any one of [1] to [4] or the antigen-binding fragment of [5] for neutralizing neurotoxicity.

[38] Use of the antibody of any one of [1] to [4] or the antigen-binding fragment of [5] for inhibiting A beta amyloid fibril formation.

[39] Use of the antibody of any one of [1] to [4] or the antigen-binding fragment of [5] for neutralizing (suppressing) synaptic toxicity.

Advantageous Effects of Invention

The antibodies provided by the present invention are expected to contribute to the establishment of preventive/therapeutic methods selective to molecules responsible for evoking pathological conditions of Alzheimer's disease, and the establishment of early diagnostic markers for Alzheimer's disease.

BRIEF DESCRIPTION OF DRAWINGS

FIG. 5 shows the results of neutralization assay against A beta-induced cytotoxicity using each of the antibodies.

FIG. 6 shows the results of inhibition assay against A beta fibril formation using each of the antibodies.

DESCRIPTION OF EMBODIMENTS

Figure 1:
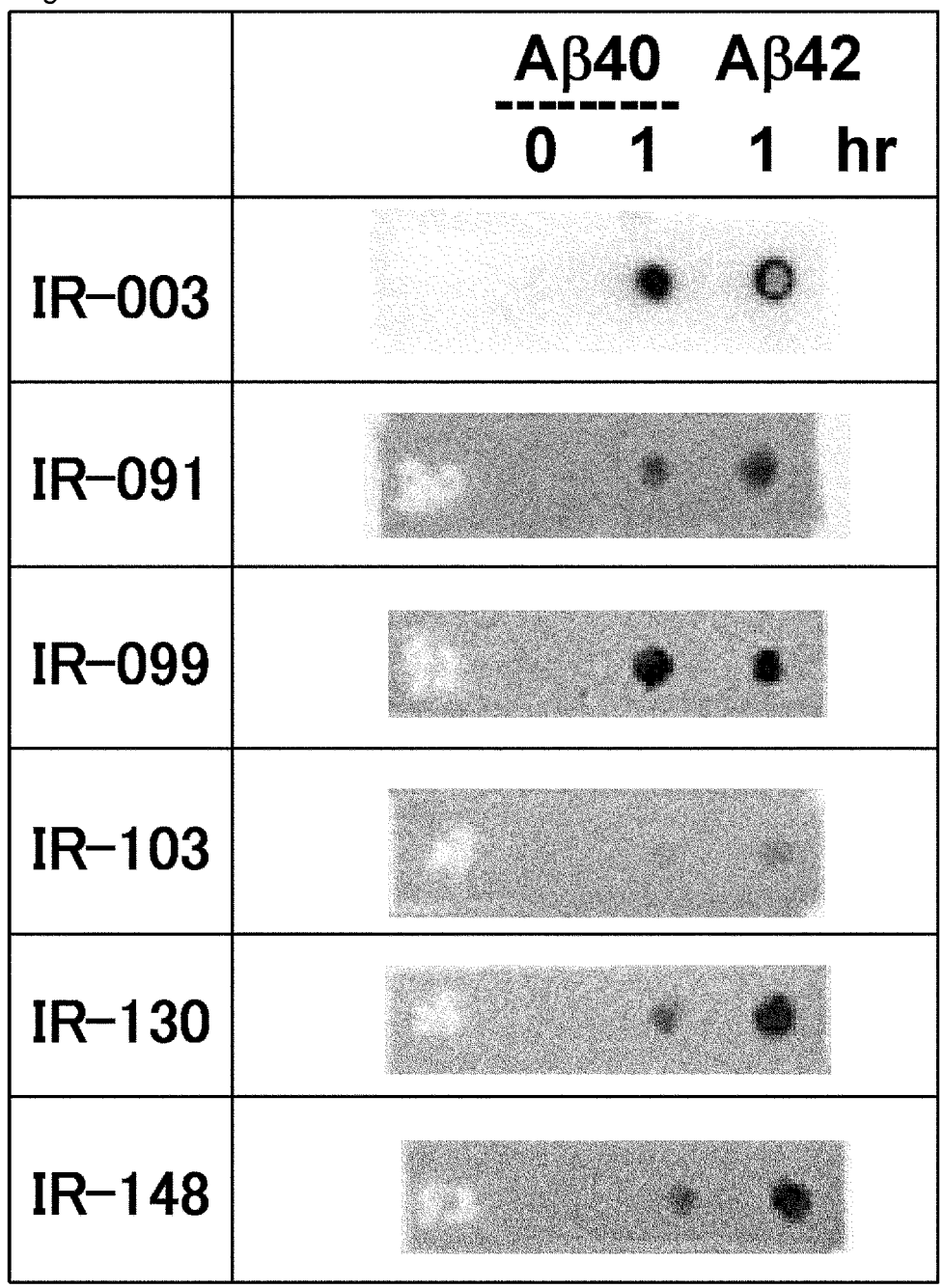
FIG. 1 presents photographs of dot-blot analysis results on each of the IR-003, IR-091, IR-099, IR-103, IR-130, and IR-148 antibodies.

The present invention will be described more specifically below.

As described above, the present inventors succeeded in obtaining antibodies that bind specifically to A beta oligomers but not to A beta monomers. That is, the present invention provides antibodies that bind to A beta oligomers but not to A beta monomers. Furthermore, the present invention provides antibodies that bind to A beta oligomers but not to A beta monomers and amyloid precursor protein (APP). The antibodies are preferably isolated or purified.

The terms "isolated" and "purified" used for substances (antibodies and such) of the present invention indicate that the substances do not substantially include at least one other substance that may be contained in the natural source. Therefore, "isolated antibodies" and "purified antibodies" refer to antibodies that do not substantially include cell materials such as hydrocarbons, lipids, or other contaminant proteins from the cell or tissue source from which the antibodies (proteins) are derived. When the antibodies are chemically synthesized, the terms refer to antibodies that do not substantially include chemical precursor substances or other chemical substances. In a preferred embodiment, the antibodies of the present invention are isolated or purified.

"Antibodies" refers to glycoproteins that have the same structural characteristics. Antibodies show binding specificity towards specific antigens. Herein, "antigens" refers to proteins that have the ability to bind to the corresponding antibodies, and induce antigen-antibody reactions in vivo.

Herein, the antibody heavy chain may be denoted as "H chain", the antibody light chain may be denoted as "L chain", the heavy chain variable region may be denoted as "VH", the light chain variable region may be denoted as "VL", the heavy chain constant region may be denoted as "CH", the light chain constant region may be denoted as "CL", the framework region may be denoted as "FR", and the complementarity-determining region may be denoted as "CDR".

A beta proteins, which are the major constituents of amyloids, are peptides consisting of 40 to 42 amino acids, and are known to be produced from precursor proteins called amyloid precursor proteins (APPs) by the action of proteases. Besides amyloid fibrils collected in ultracentrifuged sediment fractions, the amyloid molecules produced from APPs include oligomeric non-fibrous assemblies in addition to soluble monomers. "A beta oligomers" of the present invention refer to non-fibrous assemblies. The degree of A beta polymerization of "A beta oligomer" of the present invention is not particularly limited, but is typically 2 to 150. The "A beta oligomers" of the present invention include, for example, A beta40 (A beta 1-40) oligomers, A beta42 (A beta 1-42) oligomers, and A beta40/A beta42 oligomers (in which A beta40 and A beta42 are polymerized). For example, "A beta oligomers" of the present invention are, typically, molecules showing a molecular weight of 45 to 160 kDa in SDS-PAGE, and 22.5 to 1,035 kDa in Blue Native PAGE. Using molecular sieves, the molecules are collected mainly in the >100 kDa retention solution. When observed under an atomic force microscope, the molecules show mixed morphologies of granular, bead-shaped, and ring-shaped molecules having a height of 1.5 to 3.1 nm.

There is no limitation on the origin and form of the antibodies used in the present invention as long as they bind to A beta oligomers but not to A beta monomers, or they bind to A beta oligomers but not to A beta monomers and amyloid precursor protein.

The antibodies of the present invention are featured by the characteristics that they bind to A beta oligomers but not to A beta monomers, or they bind to A beta oligomers but not to A beta monomers and amyloid precursor protein. Preferably, these antibodies have the following characteristics.

In dot-blot analysis, they react with A beta40 oligomers and A beta42 oligomers, but not with A beta40 monomers.

In competitive ELISA assay using immobilized A beta oligomers, the 50%-inhibition concentration (IC50) of A beta monomer for the binding of the antibodies to the immobilized A beta oligomers is higher than that of A beta oligomer.

In competitive ELISA assay using immobilized A beta oligomers, IC50 of A beta monomer is 500 nmol/L or more, preferably 1000 nmol/L or more, more preferably 1500 nmol/L or more, or more preferably 2000 nmol/L or more.

In competitive ELISA assay using immobilized A beta oligomers, IC50 of A beta oligomer is 100 nmol/L or less, preferably 50 nmol/L or less, more preferably 25 nmol/L or less, or more preferably 20 nmol/L or less.

In competitive ELISA assay using immobilized A beta oligomers, the antigen selectivity shown by IC50 of A beta monomer versus A beta oligomer for the binding of the antibodies to the immobilized A beta oligomers, i.e., IC50 of A beta monomer/IC50 of A beta oligomer, is 50 or more, preferably 100 or more, more preferably 150 or more, or more preferably 200 or more.

In the affinity analysis for A beta oligomers using Biacore (Biacore 3000), the binding rate constant (kd) is $1.0E+04\ M^{-1}\ S^{-1}$ or more, preferably $2.0E+04\ M^{-1}\ S^{-1}$ or more, more preferably $5.0E+04\ M^{-1}\ S^{-1}$ or more, or more preferably $1.0E+05\ M^{-1}\ S^{-1}$ or more.

In the affinity analysis for A beta oligomers using Biacore (Biacore 3000), the dissociation rate constant (kd) is $0.5\ S^{-1}$ or less, preferably $0.2\ S^{-1}$ or less, more preferably $0.1\ S^{-1}$ or less, more preferably $0.05\ S^{-1}$ or less, more preferably $0.01\ S^{-1}$ or less, or more preferably $6.0E-03\ S^{-1}$ or less.

In the affinity analysis for A beta oligomers using Biacore (Biacore 3000), the dissociation constant (KD) is 5.0E-06 M or less, preferably 1.0E-06 M or less, more preferably 7.0E-07 M or less, more preferably 1.0E-07 M or less, or more preferably 5.0E-08 M or less.

In immunoblot analysis, they do not react with human amyloid precursor protein.

The antibodies of the present invention may be featured by at least one of the above characteristics. Furthermore, the antibodies may be featured by two or more of the above characteristics.

"Antibodies" of the present invention include both monoclonal and polyclonal antibodies. The antibodies of the present invention also include any type of antibodies such as non-human animal antibodies, humanized antibodies, chimeric antibodies, human antibodies, the later-described minibodies, amino acid sequence-modified antibodies, modified antibodies conjugated to other molecules (for example, polymers such as polyethylene glycol), and sugar chain-modified antibodies.

Herein, the term "monoclonal antibodies" refers to antibodies that are obtained from a substantially homogeneous population of antibodies. That is, the individual antibodies constituting the population are identical with the exception of possible natural mutants that may be present in a trace amount. Monoclonal antibodies are highly specific and recognize a single antigenic site. Each of the monoclonal antibodies recognizes a single determinant of the antigen, in contrast to conventional (polyclonal) antibody preparations that typically contain different antibodies against different antigenic determinants (epitopes).

In addition to the above-mentioned specificity, monoclonal antibodies have the advantage that they can be synthesized from a hybridoma culture that is not contaminated with other immunoglobulins. Therefore, "monoclonal" indicates the characteristics of antibodies that can be obtained from a substantially homogeneous antibody population. This term does not indicate the requirement for any specific method for antibody production.

Basically, monoclonal antibodies can be produced by using known techniques. For example, they may be produced by the hybridoma method first described by Kohler and Milstein (Nature 256: 495-7, 1975), or by the recombinant DNA method (Cabilly et al., Proc. Natl. Acad. Sci. USA 81:3273-7, 1984), but the methods are not limited thereto. For example, when using the hybridoma method, an A beta oligomer is used as a sensitizing antigen, and immunization is carried out according to a conventional immunization method. The obtained immune cells are fused with known parent cells by a conventional cell fusion method, and monoclonal antibody-producing cells can be screened and isolated using a conventional screening method.

The monoclonal antibodies of the present invention can be produced, for example, as follows. First, synthetic A beta 1-42 (Peptide Institute, Inc., Osaka) is dissolved in distilled deionized water or a 10 mM phosphate buffer solution, and this is incubated at 37 degrees C. for 18 hours. Then, the peptides are separated by 4-12% SDS-PAGE, and visualized by CBB staining, and the portion of the A beta 1-42 tetramer alone which is not contaminated with the A beta 1-42 monomer is cut out. Next, BALB/c mice are immunized at their foot pad with 2.5 micro g of the A beta 1-42 tetramer emulsified using complete Freund's adjuvant. Subsequently, booster immunizations are carried out six times. Hybridomas are produced from the inguinal lymph node by fusion with Sp2/O—Ag14 cells using Polyethylene Glycol 1500.

In the present invention, the animals immunized with sensitizing antigens are not particularly limited, but are preferably selected considering the compatibility with parent cells used for cell fusion. Generally, rodents, lagomorphs, or primates are used. Rodents include, for example, mice, rats, and hamsters. Lagomorphs include, for example, rabbits. Primates include, for example, Catarrhini (old-world) monkeys such as *Macaca fascicularis, Macaca mulatta, hamadryas*, and *chimpanzees*.

Animals are immunized with sensitizing antigens according to known methods. For example, as a standard method, immunization is performed by intraperitoneal or subcutaneous injection of a sensitizing antigen into mammals.

An example of the parent cells fused with the aforementioned immunocytes is the Sp2/O—Ag14 cell, which will be described below in the Examples. However, various other known cell lines can be used.

Cell fusion between the aforementioned immunocyte and a myeloma cell can be carried out basically according to known methods including the method by Kohler and Milstein (Kohler G. and Milstein C., Methods Enzymol. (1981) 73, 3-46).

Hybridomas obtained in this manner are selected by culturing them in a conventional selection culture medium such as a HAT culture medium, which contains hypoxanthine, aminopterin, and thymidine. Culturing in the above-mentioned HAT culture medium is generally continued for several days to several weeks for an adequate time for killing cells other than the desired hybridomas (non-fused cells). Next, a conventional limiting dilution method is performed for screening and singly-cloning of a hybridoma that produces the desired antibody.

Thereafter, the obtained hybridoma is transplanted into the abdominal cavity of a mouse, and ascitic fluid containing the desired monoclonal antibodies is extracted. For example, the antibodies can be purified from the ascitic fluid by conventional protein separation and/or purification methods such as a selected combination of column chromatography including, but not limited to, affinity chromatography, filtration, ultrafiltration, salt precipitation, dialysis, SDS polyacrylamide gel electrophoresis, and isoelectric focusing (Antibodies: A Laboratory manual, Harlow and David, Lane (edit.), Cold Spring Harbor Laboratory, 1988).

Protein A columns and Protein G columns can be used for affinity columns. Examples of the Protein A columns used include Hyper D, POROS, and Sepharose F.F. (Pharmacia).

Chromatography (excluding affinity chromatography) includes ion exchange chromatography, hydrophobic chromatography, gel filtration, reverse-phase chromatography, and adsorption chromatography ("Strategies for Protein Purification and Characterization: A Laboratory Course Manual", Daniel R Marshak et al., Cold Spring Harbor Laboratory Press, 1996). When chromatography is carried out, liquid-phase chromatography methods such as HPLC and FPLC can be used.

Monoclonal antibody-producing hybridomas prepared in this manner can be subcultured in a conventional culture medium, and they can be stored for a long time in liquid nitrogen.

Any mammal can be immunized using an immunogen for antibody production. However, when preparing monoclonal antibodies by producing hybridomas, the compatibility with parent cells used in cell fusion for hybridoma production is preferably considered.

Generally, rodents, lagomorphs, or primates are used for the immunization. Rodents include, for example, mice, rats, and hamsters. Lagomorphs include, for example, rabbits. Primates include, for example, Catarrhini (old-world) monkeys such as *Macaca fascicularis, Macaca mulatta, hamadryas*, and *chimpanzees*.

The use of transgenic animals that have a human antibody gene repertoire is known in the art (Ishida I, et al., Cloning and Stem Cells 4: 91-102, 2002). As with other animals, to obtain human monoclonal antibodies, the transgenic animals are immunized, then antibody-producing cells are collected from the animals and fused with myeloma cells to produce hybridomas, and anti-protein human antibodies can be prepared from these hybridomas (see International Publication Nos. WO92/03918, WO94/02602, WO94/25585, WO96/33735, and WO96/34096).

Alternatively, lymphocytes immortalized with oncogenes may be used for monoclonal antibody production. For example, human lymphocytes infected with EB virus or such is immunized in vitro with immunogens. Next, the immunized lymphocytes are fused with human-derived myeloma cells (U266, etc) capable of unlimited division, and thus hybridomas that produce the desired human antibodies are obtained (Japanese Patent Application Kokai Publication No. (JP-A) S63-17688 (unexamined, published Japanese patent application)).

Once monoclonal antibodies can be obtained by any of the aforementioned methods, the antibodies may also be prepared using genetic engineering methods (see, for example, Borrebaeck C A K and Larrick J W, Therapeutic Monoclonal Antibodies, MacMillan Publishers, UK, 1990). For example, recombinant antibodies may be prepared by cloning DNAs that encode the desired antibodies from antibody-producing cells such as hybridomas or immunized lymphocytes that produce the antibodies, then inserting the cloned DNAs into appropriate vectors, and transfecting the vectors into suitable host cells. Such recombinant antibodies are also included in the present invention.

Examples of the monoclonal antibodies of the present invention include the following: the IR-003, IR-091, IR-099, IR-103, IR-130, and IR-148 antibodies.

For the IR-003 antibody of the present invention:

the amino acid sequence and the nucleotide sequence of the H-chain variable region (VH) are shown in SEQ ID NO: 98 and SEQ ID NO: 97, respectively;

the amino acid sequence and the nucleotide sequence of the L-chain variable region (VL) are shown in SEQ ID NO: 100 and SEQ ID NO: 99, respectively;

the amino acid sequence and the nucleotide sequence of the H-chain CDR1 are shown in SEQ ID NO: 6 and SEQ ID NO: 5, respectively;

the amino acid sequence and the nucleotide sequence of the H-chain CDR2 are shown in SEQ ID NO: 8 and SEQ ID NO: 7, respectively;

the amino acid sequence and the nucleotide sequence of the H-chain CDR3 are shown in SEQ ID NO: 10 and SEQ ID NO: 9, respectively;

the amino acid sequence and the nucleotide sequence of the L-chain CDR1 are shown in SEQ ID NO: 12 and SEQ ID NO: 11, respectively;

the amino acid sequence and the nucleotide sequence of the L-chain CDR2 are shown in SEQ ID NO: 14 and SEQ ID NO: 13, respectively; and the amino acid sequence and the nucleotide sequence of the L-chain CDR3 are shown in SEQ ID NO: 16 and SEQ ID NO: 15, respectively.

For the IR-091 antibody of the present invention:

the amino acid sequence and the nucleotide sequence of the H-chain variable region (VH) are shown in SEQ ID NO: 102 and SEQ ID NO: 101, respectively;

the amino acid sequence and the nucleotide sequence of the L-chain variable region (VL) are shown in SEQ ID NO: 104 and SEQ ID NO: 103, respectively;

the amino acid sequence and the nucleotide sequence of the H-chain CDR1 are shown in SEQ ID NO: 22 and SEQ ID NO: 21, respectively;

the amino acid sequence and the nucleotide sequence of the H-chain CDR2 are shown in SEQ ID NO: 24 and SEQ ID NO: 23, respectively;

the amino acid sequence and the nucleotide sequence of the H-chain CDR3 are shown in SEQ ID NO: 26 and SEQ ID NO: 25, respectively;

the amino acid sequence and the nucleotide sequence of the L-chain CDR1 are shown in SEQ ID NO: 28 and SEQ ID NO: 27, respectively;

the amino acid sequence and the nucleotide sequence of the L-chain CDR2 are shown in SEQ ID NO: 30 and SEQ ID NO: 29, respectively; and the amino acid sequence and the nucleotide sequence of the L-chain CDR3 are shown in SEQ ID NO: 32 and SEQ ID NO: 31, respectively.

For the IR-099 antibody of the present invention:

the amino acid sequence and the nucleotide sequence of the H-chain variable region (VH) are shown in SEQ ID NO: 106 and SEQ ID NO: 105, respectively;

the amino acid sequence and the nucleotide sequence of the L-chain variable region (VL) are shown in SEQ ID NO: 108 and SEQ ID NO: 107, respectively;

the amino acid sequence and the nucleotide sequence of the H-chain CDR1 are shown in SEQ ID NO: 38 and SEQ ID NO: 37, respectively;

the amino acid sequence and the nucleotide sequence of the H-chain CDR2 are shown in SEQ ID NO: 40 and SEQ ID NO: 39, respectively;

the amino acid sequence and the nucleotide sequence of the H-chain CDR3 are shown in SEQ ID NO: 42 and SEQ ID NO: 41, respectively;

the amino acid sequence and the nucleotide sequence of the L-chain CDR1 are shown in SEQ ID NO: 44 and SEQ ID NO: 43, respectively;

the amino acid sequence and the nucleotide sequence of the L-chain CDR2 are shown in SEQ ID NO: 46 and SEQ ID NO: 45, respectively; and the amino acid sequence and the nucleotide sequence of the L-chain CDR3 are shown in SEQ ID NO: 48 and SEQ ID NO: 47, respectively.

For the IR-103 antibody of the present invention:

the amino acid sequence and the nucleotide sequence of the H-chain variable region (VH) are shown in SEQ ID NO: 110 and SEQ ID NO: 109, respectively;

the amino acid sequence and the nucleotide sequence of the L-chain variable region (VL) are shown in SEQ ID NO: 112 and SEQ ID NO: 111, respectively;

the amino acid sequence and the nucleotide sequence of the H-chain CDR1 are shown in SEQ ID NO: 54 and SEQ ID NO: 53, respectively;

the amino acid sequence and the nucleotide sequence of the H-chain CDR2 are shown in SEQ ID NO: 56 and SEQ ID NO: 55, respectively;

the amino acid sequence and the nucleotide sequence of the H-chain CDR3 are shown in SEQ ID NO: 58 and SEQ ID NO: 57, respectively;

the amino acid sequence and the nucleotide sequence of the L-chain CDR1 are shown in SEQ ID NO: 60 and SEQ ID NO: 59, respectively;

the amino acid sequence and the nucleotide sequence of the L-chain CDR2 are shown in SEQ ID NO: 62 and SEQ ID NO: 61, respectively; and the amino acid sequence and the nucleotide sequence of the L-chain CDR3 are shown in SEQ ID NO: 64 and SEQ ID NO: 63, respectively.

For the IR-130 antibody of the present invention:
the amino acid sequence and the nucleotide sequence of the H-chain variable region (VH) are shown in SEQ ID NO: 114 and SEQ ID NO: 113, respectively;
the amino acid sequence and the nucleotide sequence of the L-chain variable region (VL) are shown in SEQ ID NO: 116 and SEQ ID NO: 115, respectively;
the amino acid sequence and the nucleotide sequence of the H-chain CDR1 are shown in SEQ ID NO: 70 and SEQ ID NO: 69, respectively;
the amino acid sequence and the nucleotide sequence of the H-chain CDR2 are shown in SEQ ID NO: 72 and SEQ ID NO: 71, respectively;
the amino acid sequence and the nucleotide sequence of the H-chain CDR3 are shown in SEQ ID NO: 74 and SEQ ID NO: 73, respectively;
the amino acid sequence and the nucleotide sequence of the L-chain CDR1 are shown in SEQ ID NO: 76 and SEQ ID NO: 75, respectively;
the amino acid sequence and the nucleotide sequence of the L-chain CDR2 are shown in SEQ ID NO: 78 and SEQ ID NO: 77, respectively; and
the amino acid sequence and the nucleotide sequence of the L-chain CDR3 are shown in SEQ ID NO: 80 and SEQ ID NO: 79, respectively.

For the IR-148 antibody of the present invention:
the amino acid sequence and the nucleotide sequence of the H-chain variable region (VH) are shown in SEQ ID NO: 118 and SEQ ID NO: 117, respectively;
the amino acid sequence and the nucleotide sequence of the L-chain variable region (VL) are shown in SEQ ID NO: 120 and SEQ ID NO: 119, respectively;
the amino acid sequence and the nucleotide sequence of the H-chain CDR1 are shown in SEQ ID NO: 86 and SEQ ID NO: 85, respectively;
the amino acid sequence and the nucleotide sequence of the H-chain CDR2 are shown in SEQ ID NO: 88 and SEQ ID NO: 87, respectively;
the amino acid sequence and the nucleotide sequence of the H-chain CDR3 are shown in SEQ ID NO: 90 and SEQ ID NO: 89, respectively;
the amino acid sequence and the nucleotide sequence of the L-chain CDR1 are shown in SEQ ID NO: 92 and SEQ ID NO: 91, respectively;
the amino acid sequence and the nucleotide sequence of the L-chain CDR2 are shown in SEQ ID NO: 94 and SEQ ID NO: 93, respectively; and
the amino acid sequence and the nucleotide sequence of the L-chain CDR3 are shown in SEQ ID NO: 96 and SEQ ID NO: 95, respectively.

In an embodiment, the antibodies of the present invention include minibodies. A minibody contains an antibody fragment lacking a portion of a whole antibody, and is not particularly limited as long as it has the ability to bind to an antigen. Examples of antibody fragments include Fab, Fab', F(ab')2, and Fv. Examples of minibodies include Fab, Fab', F(ab')2, Fv, scFv (single chain Fv), diabody, and sc(Fv)2 (single chain (Fv)2).

These minibodies can be obtained, for example, by treating an antibody with an enzyme to produce an antibody fragment. Known enzymes for producing an antibody fragment include papain, pepsin, and plasmin. Alternatively, a gene construct encoding an antibody fragment can be produced, inserted into an expression vector, and expressed in a suitable host cell (see, for example, Co, M. S. et al., J. Immunol. (1994) 152, 2968-2976, Better, M. and Horwitz, A. H. Methods in Enzymology (1989) 178, 476-496, Plueckthun, A. and Skerra, A. Methods in Enzymology (1989) 178, 476-496, Lamoyi, E., Methods in Enzymology (1989) 121, 652-663, Rousseaux, J. et al., Methods in Enzymology (1989) 121, 663-669, Bird, R. E. et al., TIBTECH (1991) 9, 132-137).

Herein, "antigen-binding fragments" means the above-mentioned antibody fragments having antigen-binding ability, or minibodies including the antibody fragments having antigen-binding ability. Antibody fragments that bind to A beta oligomers but not to A beta monomers, or antibody fragments that bind to A beta oligomers but not to A beta monomers and amyloid precursor protein, are also included in the present invention. Hereinafter, reference to "antibody" includes reference to the above "antigen-binding fragment".

Polyclonal antibodies of the present invention can be obtained by the following methods. To obtain the polyclonal antibodies, blood is removed from a mammal sensitized with an antigen after the mammal is immunized with an A beta oligomer (e.g., A beta tetramer) as a sensitizing antigen using a conventional method and the serum level of the desired antibody is confirmed to be increased. Serum is separated from blood by a known method. When a polyclonal antibody is used, serum containing the polyclonal antibody may be utilized. Alternatively, if necessary, a fraction containing the polyclonal antibody may be isolated from serum and then used. For example, immunoglobulin G or M can be prepared by obtaining a fraction that specifically recognizes an A beta oligomer using an affinity column coupled with an A beta oligomer, and then purifying this fraction using a Protein A or Protein G column.

The present invention provides A beta oligomers bound by the antibodies of the present invention. Preferably, the antibodies include the following: the IR-003, IR-091, IR-099, IR-103, IR-130, and IR-148 antibodies. The A beta oligomers can be used as antigens for preparing antibodies, or vaccines.

In other words, in the present invention, the A beta oligomers are antigens bound by the following antibodies: the IR-003, IR-091, IR-099, IR-103, IR-130, and IR-148 antibodies.

Furthermore, the antibodies of the present invention include antibodies that bind to the antigens bound by the following antibodies: the IR-003, IR-091, IR-099, IR-103, IR-130, and IR-148 antibodies.

Furthermore, the present invention provides an antibody of any one of (1) to (12) below:
(1) an antibody that comprises an H chain having CDR1, CDR2, and CDR3, which are identified in VH comprising the amino acid sequence of SEQ ID NO: 98;
(2) an antibody that comprises an L chain having CDR1, CDR2, and CDR3, which are identified in VL comprising the amino acid sequence of SEQ ID NO: 100;
(3) an antibody that comprises an H chain having CDR1, CDR2, and CDR3, which are identified in VH comprising the amino acid sequence of SEQ ID NO: 102;
(4) an antibody that comprises an L chain having CDR1, CDR2, and CDR3, which are identified in VL comprising the amino acid sequence of SEQ ID NO: 104;
(5) an antibody that comprises an H chain having CDR1, CDR2, and CDR3, which are identified in VH comprising the amino acid sequence of SEQ ID NO: 106;
(6) an antibody that comprises an L chain having CDR1, CDR2, and CDR3, which are identified in VL comprising the amino acid sequence of SEQ ID NO: 108;
(7) an antibody that comprises an H chain having CDR1, CDR2, and CDR3, which are identified in VH comprising the amino acid sequence of SEQ ID NO: 110;

(8) an antibody that comprises an L chain having CDR1, CDR2, and CDR3, which are identified in VL comprising the amino acid sequence of SEQ ID NO: 112;

(9) an antibody that comprises an H chain having CDR1, CDR2, and CDR3, which are identified in VH comprising the amino acid sequence of SEQ ID NO: 114;

(10) an antibody that comprises an L chain having CDR1, CDR2, and CDR3, which are identified in VL comprising the amino acid sequence of SEQ ID NO: 116;

(11) an antibody that comprises an H chain having CDR1, CDR2, and CDR3, which are identified in VH comprising the amino acid sequence of SEQ ID NO: 118;

(12) an antibody that comprises an L chain having CDR1, CDR2, and CDR3, which are identified in VL comprising the amino acid sequence of SEQ ID NO: 120.

As mentioned above, "CDR1, CDR2, and CDR3" refers to CDR determined by a method well-known in the art (e.g., see Kabat, Elvin A., Sequences of proteins of immunological interest 5th ed., National Institutes of Health, 1991; Chothia et al, J Mol Biol 196:901-917, 1987). It is a technical common knowledge in the art that the amino acid sequences of CDR1, CDR2, and CDR3 can be identified in amino acid sequences of regions including CDR1, CDR2, and CDR3, using a method well-known in the art. In the following embodiments, for each antibody, an example of the CDR amino acid sequence determined according to the definition by Kabat is shown.

In a preferred embodiment, the antibody of the present invention is any one of (1) to (38) below.

IR-003 antibody:

(1) an antibody that comprises an H chain having the amino acid sequence of SEQ ID NO: 6 as CDR1, the amino acid sequence of SEQ ID NO: 8 as CDR2, and the amino acid sequence of SEQ ID NO: 10 as CDR3;

(2) an antibody that comprises an L chain having the amino acid sequence of SEQ ID NO: 12 as CDR1, the amino acid sequence of SEQ ID NO: 14 as CDR2, and the amino acid sequence of SEQ ID NO: 16 as CDR3;

(3) an antibody that comprises the H chain of (1) and the L chain of (2);

(4) an antibody that comprises an H chain having the amino acid sequence of SEQ ID NO: 98 as VH;

(5) an antibody that comprises an L chain having the amino acid sequence of SEQ ID NO: 100 as VL;

(6) an antibody that comprises the H chain of (4) and the L chain of (5);

IR-091 antibody:

(7) an antibody that comprises an H chain having the amino acid sequence of SEQ ID NO: 22 as CDR1, the amino acid sequence of SEQ ID NO: 24 as CDR2, and the amino acid sequence of SEQ ID NO: 26 as CDR3;

(8) an antibody that comprises an L chain having the amino acid sequence of SEQ ID NO: 28 as CDR1, the amino acid sequence of SEQ ID NO: 30 as CDR2, and the amino acid sequence of SEQ ID NO: 32 as CDR3;

(9) an antibody that comprises the H chain of (7) and the L chain of (8);

(10) an antibody that comprises an H chain having the amino acid sequence of SEQ ID NO: 102 as VH;

(11) an antibody that comprises an L chain having the amino acid sequence of SEQ ID NO: 104 as VL; (12) an antibody that comprises the H chain of (10) and the L chain of (11);

IR-099 antibody:

(13) an antibody that comprises an H chain having the amino acid sequence of SEQ ID NO: 38 as CDR1, the amino acid sequence of SEQ ID NO: 40 as CDR2, and the amino acid sequence of SEQ ID NO: 42 as CDR3;

(14) an antibody that comprises an L chain having the amino acid sequence of SEQ ID NO: 44 as CDR1, the amino acid sequence of SEQ ID NO: 46 as CDR2, and the amino acid sequence of SEQ ID NO: 48 as CDR3;

(15) an antibody that comprises the H chain of (13) and the L chain of (14);

(16) an antibody that comprises an H chain having the amino acid sequence of SEQ ID NO: 106 as VH;

(17) an antibody that comprises an L chain having the amino acid sequence of SEQ ID NO: 108 as VL;

(18) an antibody that comprises the H chain of (16) and the L chain of (17);

IR-103 antibody:

(19) an antibody that comprises an H chain having the amino acid sequence of SEQ ID NO: 54 as CDR1, the amino acid sequence of SEQ ID NO: 56 as CDR2, and the amino acid sequence of SEQ ID NO: 58 as CDR3;

(20) an antibody that comprises an L chain having the amino acid sequence of SEQ ID NO: 60 as CDR1, the amino acid sequence of SEQ ID NO: 62 as CDR2, and the amino acid sequence of SEQ ID NO: 64 as CDR3;

(21) an antibody that comprises the H chain of (19) and the L chain of (20);

(22) an antibody that comprises an H chain having the amino acid sequence of SEQ ID NO: 110 as VH;

(23) an antibody that comprises an L chain having the amino acid sequence of SEQ ID NO: 112 as VL;

(24) an antibody that comprises the H chain of (22) and the L chain of (23);

IR-130 antibody:

(25) an antibody that comprises an H chain having the amino acid sequence of SEQ ID NO: 70 as CDR1, the amino acid sequence of SEQ ID NO: 72 as CDR2, and the amino acid sequence of SEQ ID NO: 74 as CDR3;

(26) an antibody that comprises an L chain having the amino acid sequence of SEQ ID NO: 76 as CDR1, the amino acid sequence of SEQ ID NO: 78 as CDR2, and the amino acid sequence of SEQ ID NO: 80 as CDR3; (27) an antibody that comprises the H chain of (25) and the L chain of (26);

(28) an antibody that comprises an H chain having the amino acid sequence of SEQ ID NO: 114 as VH;

(29) an antibody that comprises an L chain having the amino acid sequence of SEQ ID NO: 116 as VL;

(30) an antibody that comprises the H chain of (28) and the L chain of (29);

IR-148 antibody:

(31) an antibody that comprises an H chain having the amino acid sequence of SEQ ID NO: 86 as CDR1, the amino acid sequence of SEQ ID NO: 88 as CDR2, and the amino acid sequence of SEQ ID NO: 90 as CDR3;

(32) an antibody that comprises an L chain having the amino acid sequence of SEQ ID NO: 92 as CDR1, the amino acid sequence of SEQ ID NO: 94 as CDR2, and the amino acid sequence of SEQ ID NO: 96 as CDR3;

(33) an antibody that comprises the H chain of (31) and the L chain of (32);

(34) an antibody that comprises an H chain having the amino acid sequence of SEQ ID NO: 118 as VH;

(35) an antibody that comprises an L chain having the amino acid sequence of SEQ ID NO: 120 as VL;

(36) an antibody that comprises the H chain of (34) and the L chain of (35);

(37) an antibody that comprises one or more amino acid substitutions, deletions, additions, and/or insertions in the antibody of any one of (1) to (36), which has equivalent activity to the antibody of any one of (1) to (36); and

(38) an antibody that binds to the epitope bound by the antibody of any one of (1) to (36).

IR-003 antibody:

An example of the VH in the above-mentioned "H chain having the amino acid sequence of SEQ ID NO: 6 (sequence of the IR-003 antibody H-chain CDR1) as CDR1, the amino acid sequence of SEQ ID NO: 8 (sequence of the IR-003 antibody H-chain CDR2) as CDR2, and the amino acid sequence of SEQ ID NO: 10 (sequence of the IR-003 antibody H-chain CDR3) as CDR3" of (1) is a VH comprising the amino acid sequence of SEQ ID NO: 98 (sequence of the IR-003 antibody VH).

An example of the VL in the above-mentioned "L chain having the amino acid sequence of SEQ ID NO: 12 (sequence of the IR-003 antibody L-chain CDR1) as CDR1, the amino acid sequence of SEQ ID NO: 14 (sequence of the IR-003 antibody L-chain CDR2) as CDR2, and the amino acid sequence of SEQ ID NO: 16 (sequence of the IR-003 antibody L-chain CDR3) as CDR3" of (2) is a VL comprising the amino acid sequence of SEQ ID NO: 4, more preferably a VL comprising the amino acid sequence of SEQ ID NO: 100 (sequence of the IR-003 antibody VL).

IR-091 antibody:

An example of the VH in the above-mentioned "H chain having the amino acid sequence of SEQ ID NO: 22 (sequence of the IR-091 antibody H-chain CDR1) as CDR1, the amino acid sequence of SEQ ID NO: 24 (sequence of the IR-091 antibody H-chain CDR2) as CDR2, and the amino acid sequence of SEQ ID NO: 26 (sequence of the IR-091 antibody H-chain CDR3) as CDR3" of (7) is a VH comprising the amino acid sequence of SEQ ID NO: 102 (sequence of the IR-091 antibody VH).

An example of the VL in the above-mentioned "L chain having the amino acid sequence of SEQ ID NO: 28 (sequence of the IR-091 antibody L-chain CDR1) as CDR1, the amino acid sequence of SEQ ID NO: 30 (sequence of the IR-091 antibody L-chain CDR2) as CDR2, and the amino acid sequence of SEQ ID NO: 32 (sequence of the IR-091 antibody L-chain CDR3) as CDR3" of (8) is a VL comprising the amino acid sequence of SEQ ID NO: 20, more preferably a VL comprising the amino acid sequence of SEQ ID NO: 104 (sequence of the IR-091 antibody VL).

IR-099 antibody:

An example of the VH in the above-mentioned "H chain having the amino acid sequence of SEQ ID NO: 38 (sequence of the IR-099 antibody H-chain CDR1) as CDR1, the amino acid sequence of SEQ ID NO: 40 (sequence of the IR-099 antibody H-chain CDR2) as CDR2, and the amino acid sequence of SEQ ID NO: 42 (sequence of the IR-099 antibody H-chain CDR3) as CDR3" of (13) is a VH comprising the amino acid sequence of SEQ ID NO: 106 (sequence of the IR-099 antibody VH).

An example of the VL in the above-mentioned "L chain having the amino acid sequence of SEQ ID NO: 44 (sequence of the IR-099 antibody L-chain CDR1) as CDR1, the amino acid sequence of SEQ ID NO: 46 (sequence of the IR-099 antibody L-chain CDR2) as CDR2, and the amino acid sequence of SEQ ID NO: 48 (sequence of the IR-099 antibody L-chain CDR3) as CDR3" of (14) is a VL comprising the amino acid sequence of SEQ ID NO: 36, more preferably a VL comprising the amino acid sequence of SEQ ID NO: 108 (sequence of the IR-099 antibody VL).

IR-103 antibody:

An example of the VH in the above-mentioned "H chain having the amino acid sequence of SEQ ID NO: 54 (sequence of the IR-103 antibody H-chain CDR1) as CDR1, the amino acid sequence of SEQ ID NO: 56 (sequence of the IR-103 antibody H-chain CDR2) as CDR2, and the amino acid sequence of SEQ ID NO: 58 (sequence of the IR-103 antibody H-chain CDR3) as CDR3" of (19) is a VH comprising the amino acid sequence of SEQ ID NO: 110 (sequence of the IR-103 antibody VH).

An example of the VL in the above-mentioned "L chain having the amino acid sequence of SEQ ID NO: 60 (sequence of the IR-103 antibody L-chain CDR1) as CDR1, the amino acid sequence of SEQ ID NO: 62 (sequence of the IR-103 antibody L-chain CDR2) as CDR2, and the amino acid sequence of SEQ ID NO: 64 (sequence of the IR-103 antibody L-chain CDR3) as CDR3" of (20) is a VL comprising the amino acid sequence of SEQ ID NO: 52, more preferably a VL comprising the amino acid sequence of SEQ ID NO: 112 (sequence of the IR-103 antibody VL).

IR-130 antibody:

An example of the VH in the above-mentioned "H chain having the amino acid sequence of SEQ ID NO: 70 (sequence of the IR-130 antibody H-chain CDR1) as CDR1, the amino acid sequence of SEQ ID NO: 72 (sequence of the IR-130 antibody H-chain CDR2) as CDR2, and the amino acid sequence of SEQ ID NO: 74 (sequence of the IR-130 antibody H-chain CDR3) as CDR3" of (25) is a VH comprising the amino acid sequence of SEQ ID NO: 114 (sequence of the IR-130 antibody VH).

An example of the VL in the above-mentioned "L chain having the amino acid sequence of SEQ ID NO: 76 (sequence of the IR-130 antibody L-chain CDR1) as CDR1, the amino acid sequence of SEQ ID NO: 78 (sequence of the IR-130 antibody L-chain CDR2) as CDR2, and the amino acid sequence of SEQ ID NO: 80 (sequence of the IR-130 antibody L-chain CDR3) as CDR3" of (26) is a VL comprising the amino acid sequence of SEQ ID NO: 68, more preferably a VL comprising the amino acid sequence of SEQ ID NO: 116 (sequence of the IR-130 antibody VL).

IR-148 antibody:

An example of the VH in the above-mentioned "H chain having the amino acid sequence of SEQ ID NO: 86 (sequence of the IR-148 antibody H-chain CDR1) as CDR1, the amino acid sequence of SEQ ID NO: 88 (sequence of the IR-148 antibody H-chain CDR2) as CDR2, and the amino acid sequence of SEQ ID NO: 90 (sequence of the IR-148 antibody H-chain CDR3) as CDR3" of (31) is a VH comprising the amino acid sequence of SEQ ID NO: 118 (sequence of the IR-148 antibody VH).

An example of the VL in the above-mentioned "L chain having the amino acid sequence of SEQ ID NO: 92 (sequence of the IR-148 antibody L-chain CDR1) as CDR1, the amino acid sequence of SEQ ID NO: 94 (sequence of the IR-148 antibody L-chain CDR2) as CDR2, and the amino acid sequence of SEQ ID NO: 96 (sequence of the IR-148 antibody L-chain CDR3) as CDR3" of (32) is a VL comprising the amino acid sequence of SEQ ID NO: 84, more preferably a VL comprising the amino acid sequence of SEQ ID NO: 120 (sequence of the IR-148 antibody VL).

The above-mentioned H chains, L chains, VHs, and VLs can be used to prepare the antibodies of the present invention. The present invention also relates to the above-mentioned H chains, L chains, VHs, and VLs.

The above-mentioned antibodies of (1) to (38) include not only monovalent antibodies but also multivalent antibodies with two or more valencies. The multivalent antibodies of the present invention include multivalent antibodies whose antigen binding sites are all the same and multivalent antibodies whose antigen binding sites are partially or completely different.

In a preferred embodiment, the above-mentioned antibody of (37) is an antibody with no modified CDRs. For example, the "antibody that comprises one or more amino acid substitutions, deletions, additions, and/or insertions in the antibody of (1), which has equivalent activity as the antibody of (1)" of the above-mentioned antibody of (37) is preferably "an antibody that has equivalent activity as the antibody of (1), and comprises one or more amino acid substitutions, deletions, additions, and/or insertions in the antibody of (1), and comprises an H chain having the amino acid sequence of SEQ ID NO: 6 as CDR1, the amino acid sequence of SEQ ID NO: 8 as CDR2, and the amino acid sequence of SEQ ID NO: 10 as CDR3". Another preferred antibody of the above-mentioned antibody of (37) can be expressed in a similar manner.

However, the above-mentioned antibody of (37) does not exclude an antibody in which CDR(s) is/are modified. Those skilled in the art can modify a CDR amino acid sequence without losing an equivalent activity. Amino acid mutations without losing an equivalent activity can be predicted, for example, using molecular modeling techniques.

Therefore, for the above-mentioned antibody of (37), an antibody having an equivalent activity as an antibody having an H-chain CDR and/or L-chain CDR of:

the IR-003, IR-091, IR-099, IR-103, IR-130, or IR-148 antibody can be expressed as follows:

an antibody that has equivalent activity as an antibody comprising an H chain having the amino acid sequence of SEQ ID NO: a as CDR1, the amino acid sequence of SEQ ID NO: b as CDR2, and the amino acid sequence of SEQ ID NO: c as CDR3, wherein the "antibody that has equivalent activity" comprises an H chain having: as CDR1, the amino acid sequence of SEQ ID NO: a, or an amino acid sequence with one or several amino acid substitutions, deletions, additions and/or insertions in the amino acid sequence of SEQ ID NO: a;

as CDR2, the amino acid sequence of SEQ ID NO: b, or an amino acid sequence with one or several amino acid substitutions, deletions, additions and/or insertions in the amino acid sequence of SEQ ID NO: b;

as CDR3, the amino acid sequence of SEQ ID NO: c, or an amino acid sequence with one or several amino acid substitutions, deletions, additions and/or insertions in the amino acid sequence of SEQ ID NO: c;

an antibody that has equivalent activity as an antibody comprising an L chain having the amino acid sequence of SEQ ID NO: d as CDR1, the amino acid sequence of SEQ ID NO: e as CDR2, and the amino acid sequence of SEQ ID NO: f as CDR3, wherein the "antibody that has equivalent activity" comprises an L chain having:

as CDR1, the amino acid sequence of SEQ ID NO: d, or an amino acid sequence with one or several amino acid substitutions, deletions, additions and/or insertions in the amino acid sequence of SEQ ID NO: d;

as CDR2, the amino acid sequence of SEQ ID NO: e, or an amino acid sequence with one or several amino acid substitutions, deletions, additions and/or insertions in the amino acid sequence of SEQ ID NO: e;

as CDR3, the amino acid sequence of SEQ ID NO: f, or an amino acid sequence with one or several amino acid substitutions, deletions, additions and/or insertions in the amino acid sequence of SEQ ID NO: f; or an antibody that has equivalent activity as an antibody comprising an H chain having the amino acid sequence of SEQ ID NO: a as CDR1, the amino acid sequence of SEQ ID NO: b as CDR2, and the amino acid sequence of SEQ ID NO: c as CDR3, and an L chain having the amino acid sequence of SEQ ID NO: d as CDR1, the amino acid sequence of SEQ ID NO: e as CDR2, and the amino acid sequence of SEQ ID NO: f as CDR3, wherein the "antibody that has equivalent activity" comprises: an H chain having:

as CDR1, the amino acid sequence of SEQ ID NO: a, or an amino acid sequence with one or several amino acid substitutions, deletions, additions and/or insertions in the amino acid sequence of SEQ ID NO: a;

as CDR2, the amino acid sequence of SEQ ID NO: b, or an amino acid sequence with one or several amino acid substitutions, deletions, additions and/or insertions in the amino acid sequence of SEQ ID NO: b;

as CDR3, the amino acid sequence of SEQ ID NO: c, or an amino acid sequence with one or several amino acid substitutions, deletions, additions and/or insertions in the amino acid sequence of SEQ ID NO: c and an L chain having:

as CDR1, the amino acid sequence of SEQ ID NO: d, or an amino acid sequence with one or several amino acid substitutions, deletions, additions and/or insertions in the amino acid sequence of SEQ ID NO: d;

as CDR2, the amino acid sequence of SEQ ID NO: e, or an amino acid sequence with one or several amino acid substitutions, deletions, additions and/or insertions in the amino acid sequence of SEQ ID NO: e;

as CDR3, the amino acid sequence of SEQ ID NO: f, or an amino acid sequence with one or several amino acid substitutions, deletions, additions and/or insertions in the amino acid sequence of SEQ ID NO: f.

The antibody of (37) for each of the above antibodies can be expressed by referring to the amino acid SEQ ID NO of H chain CDR1 for "a" above, the amino acid SEQ ID NO of H chain CDR2 for "b" above, the amino acid SEQ ID NO of H chain CDR3 for "c" above, the amino acid SEQ ID NO of L chain CDR1 for "d" above, the amino acid SEQ ID NO of L chain CDR2 for "e" above, the amino acid SEQ ID NO of L chain CDR3 for "f" above. For example, the antibody of (37) for an antibody having equivalent activity as an antibody that has the H chain CDR and/or L chain CDR of the IR-003 antibody can be expressed as follows:

an antibody that has equivalent activity as an antibody comprising an H chain having the amino acid sequence of SEQ ID NO: 6 as CDR1, the amino acid sequence of SEQ ID NO: 8 as CDR2, and the amino acid sequence of SEQ ID NO: 10 as CDR3, wherein the "antibody that has equivalent activity" comprises an H chain having:

as CDR1, the amino acid sequence of SEQ ID NO: 6, or an amino acid sequence with one or several amino acid substitutions, deletions, additions and/or insertions in the amino acid sequence of SEQ ID NO: 6;

as CDR2, the amino acid sequence of SEQ ID NO: 8, or an amino acid sequence with one or several amino acid substitutions, deletions, additions and/or insertions in the amino acid sequence of SEQ ID NO: 8;

as CDR3, the amino acid sequence of SEQ ID NO: 10, or an amino acid sequence with one or several amino acid substitutions, deletions, additions and/or insertions in the amino acid sequence of SEQ ID NO: 10;

an antibody that has equivalent activity as an antibody comprising an L chain having the amino acid sequence of SEQ ID NO: 12 as CDR1, the amino acid sequence of SEQ ID NO: 14 as CDR2, and the amino acid sequence of SEQ ID NO: 16 as CDR3, wherein the "antibody that has equivalent activity" comprises an L chain having:

as CDR1, the amino acid sequence of SEQ ID NO: 12, or an amino acid sequence with one or several amino acid substitutions, deletions, additions and/or insertions in the amino acid sequence of SEQ ID NO: 12;

as CDR2, the amino acid sequence of SEQ ID NO: 14, or an amino acid sequence with one or several amino acid substitutions, deletions, additions and/or insertions in the amino acid sequence of SEQ ID NO: 14;

as CDR3, the amino acid sequence of SEQ ID NO: 16, or an amino acid sequence with one or several amino acid substitutions, deletions, additions and/or insertions in the amino acid sequence of SEQ ID NO: 16; or an antibody that has equivalent activity as an antibody comprising an H chain having the amino acid sequence of SEQ ID NO: 6 as CDR1, the amino acid sequence of SEQ ID NO: 8 as CDR2, and the amino acid sequence of SEQ ID NO: 10 as CDR3, and an L chain having the amino acid sequence of SEQ ID NO: 12 as CDR1, the amino acid sequence of SEQ ID NO: 14 as CDR2, and the amino acid sequence of SEQ ID NO: 16 as CDR3, wherein the "antibody that has equivalent activity" comprises: an H chain having:

as CDR1, the amino acid sequence of SEQ ID NO: 6, or an amino acid sequence with one or several amino acid substitutions, deletions, additions and/or insertions in the amino acid sequence of SEQ ID NO: 6;

as CDR2, the amino acid sequence of SEQ ID NO: 8, or an amino acid sequence with one or several amino acid substitutions, deletions, additions and/or insertions in the amino acid sequence of SEQ ID NO: 8;

as CDR3, the amino acid sequence of SEQ ID NO: 10, or an amino acid sequence with one or several amino acid substitutions, deletions, additions and/or insertions in the amino acid sequence of SEQ ID NO: 10 and an L chain having:

as CDR1, the amino acid sequence of SEQ ID NO: 12, or an amino acid sequence with one or several amino acid substitutions, deletions, additions and/or insertions in the amino acid sequence of SEQ ID NO: 12;

as CDR2, the amino acid sequence of SEQ ID NO: 14, or an amino acid sequence with one or several amino acid substitutions, deletions, additions and/or insertions in the amino acid sequence of SEQ ID NO: 14;

as CDR3, the amino acid sequence of SEQ ID NO: 16, or an amino acid sequence with one or several amino acid substitutions, deletions, additions and/or insertions in the amino acid sequence of SEQ ID NO: 16.

Furthermore, as mentioned above, regarding the antibodies in the embodiments mentioned below, the antibody of (37) for each of the antibodies can be expressed by referring to the amino acid SEQ ID NOs of VH, VL, CDR of:

the IR-003, IR-091, IR-099, IR-103, IR-130, or IR-148 antibody for "a" to "h".

In the above antibodies in which CDRs are modified, "several" means, preferably five amino acids or less, more preferably four amino acids or less, more preferably three amino acids or less, more preferably two amino acids. The number of amino acids substituted, deleted, added, and/or inserted between two amino acid sequences can be identified by aligning the amino acid sequences using sequence analysis programs. The programs for alignment include, for example, FASTA (Lipman D J, Pearson W R (1985) Science 227 (4693):1435-1441; Pearson, W R., Lipman, D J (1988) Proc. Natl. Acad. Sci. USA 85 (8): 2444-2448), BLAST (Altschul et al (1990) J. Mol. Biol. 215:403-410; Altschul et al (1997) Nucleic Acids Res. 25: 3389-402).

It is known to those skilled in the art that, in the binding specificity or affinity of an antibody to an antigen, CDR3 plays a particularly important role. Thus, in the antibodies of (37), the CDR3 sequence is preferably conserved. Therefore, in a preferred embodiment, the antibody of (37) can be expressed as follows:

an antibody that has equivalent activity as an antibody comprising an H chain having the amino acid sequence of SEQ ID NO: a as CDR1, the amino acid sequence of SEQ ID NO: b as CDR2, and the amino acid sequence of SEQ ID NO: c as CDR3, wherein the "antibody that has equivalent activity" comprises an H chain having:

as CDR1, the amino acid sequence of SEQ ID NO: a, or an amino acid sequence with one or several amino acid substitutions, deletions, additions and/or insertions in the amino acid sequence of SEQ ID NO: a;

as CDR2, the amino acid sequence of SEQ ID NO: b, or an amino acid sequence with one or several amino acid substitutions, deletions, additions and/or insertions in the amino acid sequence of SEQ ID NO: b;

as CDR3, the amino acid sequence of SEQ ID NO: c;

an antibody that has equivalent activity as an antibody comprising an L chain having the amino acid sequence of SEQ ID NO: d as CDR1, the amino acid sequence of SEQ ID NO: e as CDR2, and the amino acid sequence of SEQ ID NO: f as CDR3, wherein the "antibody that has equivalent activity" comprises an L chain having:

as CDR1, the amino acid sequence of SEQ ID NO: d, or an amino acid sequence with one or several amino acid substitutions, deletions, additions and/or insertions in the amino acid sequence of SEQ ID NO: d;

as CDR2, the amino acid sequence of SEQ ID NO: e, or an amino acid sequence with one or several amino acid substitutions, deletions, additions and/or insertions in the amino acid sequence of SEQ ID NO: e;

as CDR3, the amino acid sequence of SEQ ID NO: f; or an antibody that has equivalent activity as an antibody comprising an H chain having the amino acid sequence of SEQ ID NO: a as CDR1, the amino acid sequence of SEQ ID NO: b as CDR2, and the amino acid sequence of SEQ ID NO: c as CDR3, and an L chain having the amino acid sequence of SEQ ID NO: d as CDR1, the amino acid sequence of SEQ ID NO: e as CDR2, and the amino acid sequence of SEQ ID NO: f as CDR3, wherein the "antibody that has equivalent activity" comprises: an H chain having:

as CDR1, the amino acid sequence of SEQ ID NO: a, or an amino acid sequence with one or several amino acid substitutions, deletions, additions and/or insertions in the amino acid sequence of SEQ ID NO: a;

as CDR2, the amino acid sequence of SEQ ID NO: b, or an amino acid sequence with one or several amino acid substitutions, deletions, additions and/or insertions in the amino acid sequence of SEQ ID NO: b;

as CDR3, the amino acid sequence of SEQ ID NO: c and an L chain having:

as CDR1, the amino acid sequence of SEQ ID NO: d, or an amino acid sequence with one or several amino acid substitutions, deletions, additions and/or insertions in the amino acid sequence of SEQ ID NO: d;

as CDR2, the amino acid sequence of SEQ ID NO: e, or an amino acid sequence with one or several amino acid substitutions, deletions, additions and/or insertions in the amino acid sequence of SEQ ID NO: e;

as CDR3, the amino acid sequence of SEQ ID NO: f.

Regarding the antibodies of (37), an antibody having equivalent activity as an antibody that has the VH and/or VL of:

the IR-003, IR-091, IR-099, IR-103, IR-130, or IR-148 antibody can be expressed as follows:

an antibody that has equivalent activity as an antibody comprising an H chain having VH comprising the amino acid sequence of SEQ ID NO: g, wherein the "antibody that has equivalent activity" comprises an H chain having VH comprising an amino acid sequence in which one or several amino acids are substituted, deleted, added, and/or inserted in the amino acid sequence of SEQ ID NO: g;

an antibody that has equivalent activity as an antibody comprising an L chain having VL comprising the amino acid sequence of SEQ ID NO: h, wherein the "antibody that has equivalent activity" comprises an H chain having VL comprising an amino acid sequence in which one or several amino acids are substituted, deleted, added, and/or inserted in the amino acid sequence of SEQ ID NO: h;

or an antibody that has equivalent activity as an antibody comprising an H chain having VH comprising the amino acid sequence of SEQ ID NO: g and an L chain having VL comprising the amino acid sequence of SEQ ID NO: h, wherein the "antibody that has equivalent activity" comprises an H chain having VH comprising the amino acid sequence of SEQ ID NO: g, or an amino acid sequence in which one or several amino acids are substituted, deleted, added, and/or inserted in the amino acid sequence of SEQ ID NO: g, and an L chain having VL comprising the amino acid sequence of SEQ ID NO: h, or an amino acid sequence in which one or several amino acids are substituted, deleted, added, and/or inserted in the amino acid sequence of SEQ ID NO: h.

The antibody of (37) for each of the above antibodies can be expressed by referring to the amino acid SEQ ID NO of VH for "g" above, and the amino acid SEQ ID NO of VL for "h" above. For example, the antibody of (37) for an antibody having equivalent activity as an antibody that has the VH and/or VL chain of the IR-003 antibody can be expressed as follows:

an antibody that has equivalent activity as an antibody comprising an H chain having VH comprising the amino acid sequence of SEQ ID NO: 98, wherein the "antibody that has equivalent activity" comprises an H chain having VH comprising an amino acid sequence in which one or several amino acids are substituted, deleted, added, and/or inserted in the amino acid sequence of SEQ ID NO: 98;

an antibody that has equivalent activity as an antibody comprising an L chain having VL comprising the amino acid sequence of SEQ ID NO: 100, wherein the "antibody that has equivalent activity" comprises an H chain having VL comprising an amino acid sequence in which one or several amino acids are substituted, deleted, added, and/or inserted in the amino acid sequence of SEQ ID NO: 100;

or an antibody that has equivalent activity as an antibody comprising an H chain having VH comprising the amino acid sequence of SEQ ID NO: 98 and an L chain having VL comprising the amino acid sequence of SEQ ID NO: 100, wherein the "antibody that has equivalent activity" comprises an H chain having VH comprising the amino acid sequence of SEQ ID NO: 98, or an amino acid sequence in which one or several amino acids are substituted, deleted, added, and/or inserted in the amino acid sequence of SEQ ID NO: 98, and an L chain having VL comprising the amino acid sequence of SEQ ID NO: 100, or an amino acid sequence in which one or several amino acids are substituted, added, and/or inserted in the amino acid sequence of SEQ ID NO: 100.

In the above antibodies in which VH and/or VL are modified, "several" means, preferably 50 amino acids or less, 30 amino acids or less, 20 amino acids or less, 15 amino acids or less, or 10 amino acids or less, more preferably nine, eight, seven, six, five, four, three, or two amino acids. As long as the equivalent activity is retained, the positions of the modified amino acids are not particularly limited; however, amino acids in FR are preferably modified.

Thus, in a preferred embodiment, among the antibodies of (37), an antibody having equivalent activity as an antibody that has the VH and/or VL of:

the IR-003, IR-091, IR-099, IR-103, IR-130, or IR-148 antibody can be expressed as follows:

an antibody that has equivalent activity as an antibody comprising an H chain having VH comprising the amino acid sequence of SEQ ID NO: a, wherein the "antibody that has equivalent activity" comprises an H chain having VH comprising an amino acid sequence in which one or several amino acids are substituted, deleted, added, and/or inserted in the amino acid sequence of SEQ ID NO: a, and the amino acid sequence of SEQ ID NO: b as CDR1, the amino acid sequence of SEQ ID NO: c as CDR2, and the amino acid sequence of SEQ ID NO: d as CDR3;

an antibody that has equivalent activity as an antibody comprising an L chain having VL comprising the amino acid sequence of SEQ ID NO: e, wherein the "antibody that has equivalent activity" comprises an L chain having VL comprising an amino acid sequence in which one or several amino acids are substituted, deleted, added, and/or inserted in the amino acid sequence of SEQ ID NO: e, and the amino acid sequence of SEQ ID NO: f as CDR1, the amino acid sequence of SEQ ID NO: g as CDR2, and the amino acid sequence of SEQ ID NO: h as CDR3;

or an antibody that has equivalent activity as an antibody comprising an H chain having VH comprising the amino acid sequence of SEQ ID NO: a and VL comprising the amino acid sequence of SEQ ID NO: e, wherein the "antibody that has equivalent activity" comprises:

an H chain having VH comprising the amino acid sequence of SEQ ID NO: a, or an amino acid sequence in which one or several amino acids are substituted, deleted, added, and/or inserted in the amino acid sequence of SEQ ID NO: a, and the amino acid sequence of SEQ ID NO: b as CDR1, the amino acid sequence of SEQ ID NO: c as CDR2, and the amino acid sequence of SEQ ID NO: d as CDR3, and an L chain having VL comprising the amino acid sequence of SEQ ID NO: e, or an amino acid sequence in which one or several amino acids are substituted, deleted, added, and/or inserted in the amino acid sequence of SEQ ID NO: e, and the amino acid sequence of SEQ ID NO: f as CDR1, the amino acid sequence of SEQ ID NO: g as CDR2, and the amino acid sequence of SEQ ID NO: h as CDR3.

The antibody of (37) for each of the above antibodies can be expressed by referring to the amino acid SEQ ID NO of VH for "a" above, the amino acid SEQ ID NO of H chain CDR1 for "b" above, the amino acid SEQ ID NO of H chain CDR2 for "c" above, the amino acid SEQ ID NO of H chain CDR3 for "d" above, the amino acid SEQ ID NO of VL for "e" above, the amino acid SEQ ID NO of L chain CDR1 for "f" above, the amino acid SEQ ID NO of L chain CDR2 for "g" above, the amino acid SEQ ID NO of L chain CDR3 for "h" above. For example, the antibody of (37) for an antibody having equivalent activity as an antibody that has the VH and/or VL of the IR-003 antibody can be expressed as follows:

an antibody that has equivalent activity as an antibody comprising an H chain having VH comprising the amino acid sequence of SEQ ID NO: 98, wherein the "antibody that has equivalent activity" comprises an H chain having VH comprising an amino acid sequence in which one or several amino acids are substituted, deleted, added, and/or inserted in the amino acid sequence of SEQ ID NO: 98, and the amino acid sequence of SEQ ID NO: 6 as CDR1, the amino acid sequence of SEQ ID NO: 8 as CDR2, and the amino acid sequence of SEQ ID NO: 10 as CDR3; an antibody that has equivalent activity as an antibody comprising an L chain having VL comprising the amino acid sequence of SEQ ID NO: 100, wherein the "antibody that has equivalent activity" comprises an L chain having VL comprising an amino acid sequence in which one or several amino acids are substituted, deleted, added, and/or inserted in the amino acid sequence of SEQ ID NO: 100, and the amino acid sequence of SEQ ID NO: 12 as CDR1, the amino acid sequence of SEQ ID NO: 14 as CDR2, and the amino acid sequence of SEQ ID NO: 16 as CDR3;

or an antibody that has equivalent activity as an antibody comprising an H chain having VH comprising the amino acid sequence of SEQ ID NO: 98 and VL comprising the amino acid sequence of SEQ ID NO: 100, wherein the "antibody that has equivalent activity" comprises:

an H chain having VH comprising the amino acid sequence of SEQ ID NO: 98, or an amino acid sequence in which one or several amino acids are substituted, deleted, added, and/or inserted in the amino acid sequence of SEQ ID NO: 98, and the amino acid sequence of SEQ ID NO: 6 as CDR1, the amino acid sequence of SEQ ID NO: 8 as CDR2, and the amino acid sequence of SEQ ID NO: 10 as CDR3, and an L chain having VL comprising the amino acid sequence of SEQ ID NO: 100, or an amino acid sequence in which one or several amino acids are substituted, deleted, added, and/or inserted in the amino acid sequence of SEQ ID NO: 100, and the amino acid sequence of SEQ ID NO: 12 as CDR1, the amino acid sequence of SEQ ID NO: 14 as CDR2, and the amino acid sequence of SEQ ID NO: 16 as CDR3.

In the modified antibodies that have the H chain CDR and/or L chain CDR, or VH and/or VL of:

the IR-003, IR-091, IR-099, IR-103, IR-130, or IR-148 antibody, the amino acid modifications are preferably conserved amino acid substitutions, as described below in detail. Thus, in a more preferred embodiment, in the antibodies of (37) described above, "conservative amino acid substitution" can be performed, instead of "substitution, deletion, addition, and/or insertion".

Methods for preparing a polypeptide having activity equivalent to that of a certain polypeptide that are well known to those skilled in the art include methods for introducing mutations into a polypeptide. For example, one skilled in the art can prepare an antibody having activity equivalent to that of an antibody of the present invention by introducing appropriate mutations into the antibody using site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc. Natl. Acad. Sci. USA. 82, 488-492; Kunkel (1988) Methods Enzymol. 85, 2763-2766) and such. Amino acid mutations may also occur naturally. The antibodies of the present invention also include an antibody that comprises an amino acid sequence with one or more amino acid mutations in the amino acid sequence of an antibody of the present invention, and which has activity equivalent to that of the antibody of the present invention.

Amino acid residues are preferably mutated into other amino acids that conserve the properties of the amino acid side chains. For example, amino acids are categorized as follows depending on the side chain properties: hydrophobic amino acids (A, I, L, M, F, P, W, Y, and V), hydrophilic amino acids (R, D, N, C, E, Q, G, H, K, S, and T), amino acids with aliphatic side chains (G, A, V, L, I, and P), amino acids with hydroxyl-containing side chains (S, T, and Y), amino acids with sulfur atom-containing side chains (C and M), amino acids with carboxylic acid- and amide-containing side chains (D, N, E, and Q), amino acids with basic side chains (R, K, and H), and amino acids with aromatic ring-containing side chains (H, F, Y, and W) (amino acids are represented by one-letter codes in parentheses). "Conservative amino acid substitution" refers to substitution of an amino acid with another amino acid with a conserved amino acid side chain characteristics. In the antibodies of (37), amino acid sequence mutations in an antibody are preferably "conservative amino acid substitutions".

Generally, a polypeptide having an amino acid sequence, in which one or more amino acid residues are modified (deleted, added, and/or substituted with other amino acids) in a certain amino acid sequence, is known to retain its original biological activity (function).

In addition to the above-mentioned modifications, the antibodies of the present invention may be conjugated to other substances as long as the activity is maintained. Examples of the substances include peptides, lipids, sugars and sugar chains, acetyl groups, and natural and synthetic polymers. These modifications may be performed to confer additional functions to the antibodies, or to stabilize the antibodies.

Antibodies in which several amino acid residues have been added to the amino acid sequence of an antibody of the present invention include fusion proteins containing the antibody. In the fusion proteins, the antibody is fused with another peptide or protein. Methods for producing a fusion protein can be carried out by ligating a polynucleotide encoding an antibody of the present invention in frame with a polynucleotide encoding another peptide or polypeptide, and inserting this into an expression vector, and expressing the fusion construct in a host. Techniques known to those skilled in the art can be used for this purpose. The peptides or polypeptides fused with an antibody of the present invention include, for example, known peptides such as FLAG (Hopp, T. P. et al., BioTechnology (1988) 6, 1204-1210), 6×His consisting of six histidine (His) residues, 10×His, Influenza hemagglutinin (HA), human c-myc fragments, VSV-GP fragments, p18HIV fragments, T7-tag, HSV-tag, E-tag, SV40T antigen fragments, lck tag, alpha-tubulin fragments, B-tag, and Protein C fragments; glutathione-S-transferase (GST); immunoglobulin constant regions; beta-galactosidase; and maltose-binding protein (MBP), etc. Commercially available polynucleotides encoding these peptides or polypeptides can be fused with polynucleotides encoding the antibodies of the present invention, and the fusion polypeptides can be produced by expressing the fusion polynucleotides thus prepared.

The antibodies of the present invention may differ in the amino acid sequence, molecular weight, presence or absence of sugar chains, structure and such, depending on the cell or host producing the antibodies or the purification method.

However, as long as the obtained antibody has an activity equivalent to an antibody of the present invention, it is included in the present invention.

Herein, "equivalent activity" means that the antibody of interest has the same biological or biochemical activity as an antibody of the present invention. The "activity" of the present invention includes, for example, activity to specifically bind to A beta oligomers but not bind to A beta monomers, activity to specifically bind to A beta oligomers but not bind to A beta monomers and amyloid precursor protein, anti-neurotoxic activity, A beta amyloid fibril formation suppressing activity, anti-synaptic toxicity activity, anti-memory impairment activity, anti-A beta deposition activity, anti-thioflavin S-positive plaque formation activity, and anti-A beta oligomer accumulation activity.

In a preferred embodiment, the "activity" of the present invention is activity to specifically bind to A beta oligomers but not bind to A beta monomers. As shown in the Example, the "activity to specifically bind to A beta oligomers but not bind to A beta monomer" is preferably assessed by dot blot or competitive ELISA. Specific methods of dot blot or competitive ELISA include methods described in the Examples. Furthermore, the binding activity towards A beta oligomers and monomers can be assessed by other immunodetection methods, for example, absorbance measurement, enzyme-linked immunosorbent assay (ELISA), enzyme immunoassay (EIA), radioimmunoassay (RIA), immunofluorescent method, etc. For example, in ELISA, an antibody is immobilized onto a plate, an antigen for the antibody is added to the plate, and a culture supernatant of antibody-producing cells or a purified antibody is added. Then, a secondary antibody that recognizes a primary antibody and that is tagged with an enzyme such as alkali phosphatase is added, and the plate is incubated. After washing, an enzyme substrate such as p-nitrophenyl phosphate is added to the plate, and the absorbance is measured to assess the antigen-binding ability of a sample of interest. The binding abilities for A beta oligomers and monomers are preferably measured by the same method; however, they can be measured by different methods. For example, the binding to A beta oligomers can be analysed using Biacore (GE Healthcare Sciences).

When the "activity" of the present invention is the activity to specifically bind to A beta oligomers but not bind to A beta monomers and amyloid precursor protein, the activity can be assessed by the above-mentioned methods or methods described in the Examples.

When the "activity" of the present invention is anti-neurotoxic activity, this activity can be assessed by, for example, culturing neurons with A beta in the presence or absence of an antibody, and measuring the A beta-induced cytotoxicity level inhibited by the antibody. A beta-induced cytotoxicity can be measured by, for example, live/dead two color fluorescent assay, measurement of the LDH amount derived from dead cells released into a medium. For the measurement of the LDH amount, for example, CytoTox96 (Promega) or such can be used. Specific methods for measuring anti-neurotixic activity include the methods described in the Examples.

When the "activity" of the present invention is A beta amyloid fibril formation suppressing activity, this activity can be assessed, for example, by incubating an A beta solution with or without an antibody, and detecting the A beta amyloid fibril formation level suppressed by the antibody. The amount of A beta amyloid fibril is assessed, for example, by adding a ThT (Thioflavin T) solution to a culture, and the amount of ThT bound to amyloid fibrils with ThT fluoresence. Specific methods for measuring A beta amyloid fibril formation suppressing activity include the methods described in the Examples.

When the "activity" of the present invention is anti-synaptic toxicity activity, this activity can be assessed, for example, by detecting synaptic toxicity suppressing effect by antibody administration to mutant human APP gene-expressing mice (for example, Tg2576 mice, Taconics, USA). The assessment of synaptic toxicity can be performed by mouse memory impairment test, analysis of the number of swollen dystrophic neurites using an anti-synaptophysin antibody, immunofluorescent analysis of mouse brain sections using anti-synaptophysin or anti-drebrin antibodies. When the "activity" of the present invention is anti-memory impairment activity, this activity is assessed by memory impairment test using mutant APP gene-expressing mice. If the "activity" of the present invention is anti-A beta deposition activity, anti-thioflavin S-positive plaque formation activity, or anti-A beta oligomer accumulation activity, these activities can be assessed by antibody administration test using mutant APP gene-expressing mice.

Specific methods for measuring the anti-memory impairment activity, anti-synaptic toxicity activity, anti-A beta deposition activity, anti-thioflavin S-positive plaque formation activity, and anti-A beta oligomer accumulation activity include the following method.

Female non-transgenic (non-Tg) mice for control, and Tg2576 mice having and overexpressing the Swedish-type mutant human APP gene with dual mutations (K670N and M671L) derived from familial AD are administered with the antibody of the present invention (dosage within the range of 0.4 to 5.0 mg/kg/w) or PBS into the caudal vein. The mouse age at the initiation of administration is six months or later at which memory and learning impairments are expressed, for monitoring therapeutic effect; or four months for monitoring prophylactic effect. Antibody administration period is two months for monitoring therapeutic effect, and nine months for monitoring prophylactic effect. To measure the anti-memory impairment activity, the following three behavioral paradigms are analysed after the antibody administration period (Mouri A, FASEB J, 21: 2135-2148, 2007): (1) Y-maze test for short-term memory; (2) novel object recognition test; (3) contextual fear conditioning test. To assess the other activities, mice are sacrificed after the behavioral analysis, and the brain hemispheres are sliced into 10 to 30-micro m-thick sagittal sections using a cryotome (RM 2145; Leica, Wetzlar, Germany). To observe thioflavin S-positive plaque formation, thioflavin S staining is performed as described in Wyss-Coray et al., 2001. The formation of swollen dystrophic neurites is observed using an anti-synaptophysin antibody (Chemicon, Temecula, Calif.). For each mouse, the number of thioflavin S-positive plaques and synaptophysin-positive swollen dystrophic neurites are calculated in four or five sections from a brain hemisphere at 40-fold magnification. To observe A beta deposition, serial sections briefly pre-treated with formic acid or Protease K are stained using an A beta immunostaining kit (Sigma, St. Louis, Mo.) or anti-A beta polyclonal antibody (Biosource), and immuno-positive signals are visualized using an ABC elite kit (Vector Laboratories). Images of the cerebral cortex and hippocampus are recorded using a digital camera connected with a microscope, and analyzed using a simple PCI software (Compix Imaging System, Lake Oswego, Oreg.). The number of thioflavin S-positive plaques and synaptophysin-positive swollen dystrophic neurites was determined in a double blind manner. Synaptic degeneration is observed by immunostaining using anti-synaptophysin or anti-drebrin antibodies. To assess the anti-A beta oligomer deposition activity, brain homogenates are prepared from the other brain hemisphere of the same mouse using the method by Kawarabayashi et al., J. Neuroscience 2001), and the amount of A beta oligomers is measured by SDS-PAGE and immunoblot analysis. For detection antibodies, commercially available anti-A beta oligomer monoclonal antibodies (e.g., 6E10, Covance Immuno-Technologies, Dedham, Mass.) or polyclonal antibodies (e.g., A11, Biosource, Carmarillo, Calif.) can be used.

The term "equivalent" in "equivalent activity" means that a value obtained as a biological or biochemical activity differs within 20% between two antibodies compared. The difference of the activity value is, preferably within 15%, within 10%, within 5%, or within 2.5%. Antibodies that bind to an epitope to which an antibody of any one of (1) to (36) above binds can be obtained by methods known to those skilled in the art. For example, the antibodies can be obtained by (i) determining the epitope bound by the antibody of any one of (1) to (36) using a conventional method, and producing the antibodies using a polypeptide comprising an amino acid sequence included in the epitope as an immunogen; or (ii) determining the epitopes of antibodies produced by a conventional method, and selecting antibodies whose epitope is the same as that of the antibody of any one of (1) to (36).

The above-mentioned antibodies of (1) to (38) also include any type of antibodies such as the above-described minibodies, antibodies with modified amino acid sequences such as humanized antibodies and chimeric antibodies, non-human animal antibodies, human antibodies, modified antibodies conjugated to other molecules (for example, polymers such as polyethylene glycol), and sugar chain-modified antibodies.

In a preferred embodiment, the antibodies of the present invention include:

the IR-003, IR-091, IR-099, IR-103, IR-130, and IR-148 antibodies. These antibodies can be obtained by the method described in the Examples. Alternatively, the antibodies can be prepared based on their sequence information.

In a preferred embodiment, the antibodies of the present invention include modified antibodies such as chimeric antibodies or humanized antibodies. In a more preferred embodiment, the chimeric antibodies include antibodies comprise a variable region derived from:

the IR-003, IR-091, IR-099, IR-103, IR-130, or IR-148 antibody;

and a constant region derived from human immunoglobulin. In a more preferred embodiment, humanized antibodies include antibodies comprise CDR derived from: the IR-003, IR-091, IR-099, IR-103, IR-130, or IR-148 antibody;

and FR derived from human immunoglobulin, and a constant region derived from human immunoglobulin.

The above chimeric antibodies can be expressed as follows:

an antibody that comprises an H chain having VH comprising the amino acid sequence of SEQ ID NO: a, and CH of a human antibody;

an antibody that comprises an L chain having VL comprising the amino acid sequence of SEQ ID NO: b, and CL of a human antibody; or an antibody that comprises an H chain having VH comprising the amino acid sequence of SEQ ID NO: a, and CH of a human antibody, and an L chain having VL comprising the amino acid sequence of SEQ ID NO: b, and CL of a human antibody.

Preferred embodiments of chimeric antibodies from each of the above antibodies can be expressed by referring to the amino acid SEQ ID NO of VH for "a" above, and the amino acid SEQ ID NO of VL for "b" above. For example, chimeric antibodies for the IR-003 antibody can be expressed as follows:

an antibody that comprises an H chain having VH comprising the amino acid sequence of SEQ ID NO: 98, and CH of a human antibody;

an antibody that comprises an L chain having VL comprising the amino acid sequence of SEQ ID NO: 100, and CL of a human antibody; or an antibody that comprises an H chain having VH comprising the amino acid sequence of SEQ ID NO: 98, and CH of a human antibody, and an L chain having VL comprising the amino acid sequence of SEQ ID NO: 100, and CL of a human antibody.

The above humanized antibodies can be expressed as follows:

an antibody that comprises an H chain having CDR of VH comprising the amino acid sequence of SEQ ID NO: a, FR of VH of a human antibody, and CH of a human antibody;

an antibody that comprises an L chain having CDR of VL comprising the amino acid sequence of SEQ ID NO: b, FR of VL of a human antibody, and CL of a human antibody; or an antibody that comprises an H chain having CDR of VH comprising the amino acid sequence of SEQ ID NO: a, FR of VH of a human antibody, and CH of a human antibody, and an L chain having CDR of VL comprising the amino acid sequence of SEQ ID NO: b, FR of VL of a human antibody, and CL of a human antibody.

Preferred embodiments of humanized antibodies from each of the above antibodies can be expressed by referring to the amino acid SEQ ID NO of VH for "a" above, and the amino acid SEQ ID NO of VL for "b" above. For example, humanized antibodies for the IR-003 antibody can be expressed as follows:

an antibody that comprises an H chain having CDR of VH comprising the amino acid sequence of SEQ ID NO: 98, FR of VH of a human antibody, and CH of a human antibody;

an antibody that comprises an L chain having CDR of VL comprising the amino acid sequence of SEQ ID NO: 100, FR of VL of a human antibody, and CL of a human antibody; or an antibody that comprises an H chain having CDR of VH comprising the amino acid sequence of SEQ ID NO: 98, FR of VH of a human antibody, and CH of a human antibody, and an L chain having CDR of VL comprising the amino acid sequence of SEQ ID NO: 100, FR of VL of a human antibody, and CL of a human antibody.

The above modified antibodies can be produced using known methods.

Since the antigenicity of a chimeric antibody or a humanized antibody in the human body is reduced, such an antibody is useful for administration to humans for therapeutic purposes or such.

Chimeric antibodies are produced by combining sequences derived from different animals. Examples of chimeric antibodies include antibodies comprising the heavy-chain and light-chain variable regions of a mouse antibody and the heavy-chain and light-chain constant regions of a human antibody. The production of chimeric antibodies can be carried out using known methods (see, for example, Jones et al., Nature 321:522-5, 1986; Riechmann et al., Nature 332:323-7, 1988; and Presta, Curr. Opin. Struct. Biol. 2:593-6, 1992). For example, first, genes encoding the variable regions or CDRs of the antibody of interest are prepared from the RNAs of antibody-producing cells by polymerase chain reaction (PCR) or such (see, for example, Larrick et al., "Methods: a Companion to Methods in Enzymology", Vol. 2: 106, 1991; Courtenay-Luck, "Genetic Manipulation of Monoclonal Antibodies" in Monoclonal Antibodies: Production, Engineering and Clinical Application; Ritter et al. (eds.), page 166, Cambridge University Press, 1995, and Ward et al., "Genetic Manipulation and Expression of Antibodies" in Monoclonal Antibodies: Principles and Applications; and Birch et al. (eds.), page 137, Wiley-Liss, Inc., 1995). To prepare chimeric antibodies from any one of the AL-201 to AL-333 antibodies, a gene encoding a variable region or CDR can be synthesized based on the sequence information of each of the antibodies disclosed herein. The prepared genes encoding the variable regions or CDRs are linked to genes encoding the constant regions (e.g., human antibody constant regions) or framework regions (e.g., human antibody framework regions). The genes encoding the constant regions or framework regions may be determined in a manner similar to that for the variable region-encoding or CDR-encoding genes, or alternatively, they can be prepared based on the sequence information of known antibodies. DNA sequences encoding chimeric products and CDR-grafted products may be synthesized completely or partially using oligonucleotide synthesis techniques. For example, the oligonucleotide synthesis described by Jones et al. (Nature 321:522-5, 1986) may be performed. Furthermore, in some cases, site-directed mutagenesis and polymerase chain reaction techniques may be appropriately used. Techniques for oligonucleotide-specific mutagenesis of known variable regions described by Verhoeyen et al. (Science 239: 1534-6, 1988) and Riechmann et al. (Nature 332: 323-7, 1988) may be used for modifying the variable region sequences, for example, to enhance the binding ability of chimeric antibodies. Furthermore, if necessary, enzymatic fill-in of gapped oligonucleotides using T4 DNA polymerase may be performed, for example, as described by Queen et al. (Proc. Natl. Acad. Sci. USA 86: 10029-33, 1989; and WO 90/07861).

For example, CDR-grafting techniques are known in the art ("Immunoglobulin genes", Academic Press (London), pp 260-74, 1989; and Michael A et al., Proc. Natl. Acad. Sci. USA 91: 969-73, 1994). Using the techniques, the CDRs of a certain antibody are replaced with the CDRs of another antibody. Through such replacement, the binding specificity of the former antibody is changed to that of the latter antibody. Among such chimeric antibodies, those in which the framework amino acids are derived from a human antibody are called "humanized antibodies (CDR-grafted antibodies)". When using antibodies to treat humans, human antibodies or humanized antibodies are preferably utilized.

Generally, chimeric antibodies comprise the variable regions of a non-human mammal-derived antibody and the constant regions derived from a human antibody. On the other hand, humanized antibodies comprise the complementarity-determining regions (CDR) of a non-human mammal-derived antibody and the framework regions and constant regions derived from a human antibody.

After producing the chimeric antibodies or humanized antibodies, amino acids in the variable regions (for example, FRs) or the constant regions may be substituted with other amino acids.

The origin of the variable regions of the chimeric antibodies or the CDRs of the humanized antibodies is not particularly limited.

Human antibody-derived C-regions are used for the C-regions of the chimeric antibodies and humanized antibodies. For example, C gamma1, C gamma2, C gamma3, C gamma4, C mu, C delta, C alpha 1, C alpha2, and C epsilon can be used for the H-chain C-regions, and C kappa and C lambda can be used for the L-chain C-regions. Their sequences are known. Furthermore, the human antibody C regions can be modified to improve the stability of the antibodies or their production.

The present invention provides polynucleotides encoding the above antibodies of the present invention or antigen-binding fragments thereof.

The polynucleotides of the present invention are not particularly limited as long as they encode the antibodies of the present invention, and may be a DNA or RNA. Furthermore, they may include a non-natural base. The polynucleotides of the present invention can be used for producing the antibodies of the present invention by genetic engineering techniques.

The polynucleotides of the present invention can be obtained by isolating mRNA from antibody-producing cells that produce an antibody of the present invention, obtaining cDNA by reverse transcription reaction, and amplifying the obtained cDNA by PCR or such, as described in the Examples.

In a preferred embodiment, the polynucleotides of the present invention include a polynucleotide encoding an antibody comprising the H chain CDR and/or L chain CDR of each of the following antibodies, or antigen-binding fragments thereof: the IR-003, IR-091, IR-099, IR-103, IR-130, or IR-148 antibody.

In another embodiment, the polynucleotides of the present invention include a polynucleotide encoding an antibody comprising the VH and/or VL of each of the following antibodies, or antigen-binding fragments thereof: the IR-003, IR-091, IR-099, IR-103, IR-130, or IR-148 antibody.

In the above embodiments, the polynucleotides can be obtained by synthesizing the polynucleotides based on the amino acid sequence information of each of the above antibodies described herein.

Furthermore, the present invention provides vectors comprising the polynucleotides of the present invention. The vectors of the present invention are preferably expression vectors for expressing an antibody of the present invention in a host cell. The vectors of the present invention may be used for producing the antibodies of the present invention.

The vectors of the present invention preferably comprise a promoter sequence that enables expression in a host cell, in addition to a polypeptide of the present invention. Furthermore, they may comprise a signal sequence for secretion of an antibody of the present invention. Furthermore, they may comprise a marker gene for selection of a host cell into which a vector of the present invention has been introduced. The components comprised in the vectors are not limited thereto, and may be a suitable component appropriately selected by those skilled in the art.

For example, expression vectors for expression in *E. coli* include vectors that have "ori" for amplification in *E. coli*, and have a promoter such as lacZ promoter (Ward et al., Nature (1989) 341, 544-546; FASEB J. (1992) 6, 2422-2427), araB promoter (Better et al., Science (1988) 240, 1041-1043), or T7 promoter, and a marker gene such as a drug-resistance gene against ampicillin, tetracycline, kanamycin, chloramphenicol, etc. The vectors include M13 vectors, pUC vectors, pBR322, pBluescript, pCR-Script, etc. Furthermore, for a signal sequence, the pelB signal sequence (Lei, S. P. et al J. Bacteriol. (1987) 169, 4379) or such can be used.

The vectors of the present invention other than *E. coli* expression vectors include, for example, mammal-derived expression vectors (e.g., pcDNA3 (Invitrogen), pEGF-BOS (Nucleic Acids. Res. 1990, 18(17), p5322), pEF, pCDM8), insect cell-derived expression vectors (e.g, Bac-to-BAC baculovirus expression system (Gibco BRL), pBacPAK8), plant-derived expression vectors (e.g., pMH1, pMH2), animal virusderived expression vectors (e.g., pHSV, pMV, pAdexLcw), retrovirus-derived expression vectors (e.g., pZIPneo), yeast-derived expression vectors (e.g., *Pichia*

Expression Kit (Invitrogen)), pNV11, SP-Q01), and *Bacillus*-derived expression vectors (e.g., pPL608, pKTHSO).

Expression vectors for expression in animal cells such as CHO cells, COS cells, NIH3T3 cells include vectors that have a promoter such as SV40 promoter (Mulligan et al., Nature (1979) 277, 108), MMTV-LTR promoter, EF1 alpha promoter (Mizushima et al., Nucleic Acids Res. (1990) 18, 5322), CMV promoter, or such; and a marker gene such as s drug-resistance gene against neomycin, G418, etc. These vectors include, for example, pMAM, pDR2, pBK-RSV, pBK-CMV, pOPRSV, pOP13, etc. As a signal sequence, any one of those described in the Examples can be used.

Furthermore, the present invention provides host cells that produce an antibody of the present invention or antigen-binding fragment thereof. The host cells include cells that have a polynucleotide of the present invention or a vector of the present invention. The host cells of the present invention may be used to produce the antibodies or antigen-binding fragments of the present invention.

The host cells of the present invention are not limited to hybridomas that produce an antibody of the present invention, and may be prokaryotes or eukaryotes into which a vector of the present invention has been introduced. When eukaryotes are used as host cells, for example, animal cells, plant cells, or fungal cells can be used. Animal cells include mammal cells (CHO (J. Exp. Med. (1995) 108, 945), COS, 3T3, myeloma, BHK (baby hamster kidney), HeLa, Vero cells, etc.), amphibian cells (Xenopus oocytes (Valle, et al., Nature (1981) 291, 358-340), etc.), insect cells (Sf9, Sf21, Tn5, etc.). As plant cells, for example, cells derived from *Nicotiana tabacum* are known as a protein expression system, and they may be cultured into callus and used. Fungal cells include, for example, yeast (e.g., the genus *Saccharomyces* (*Saccharomyces cerevisiae*, *Saccharomyces pombe*, etc.), filamentous fungi (e.g., the genus *Aspergillus* (*Aspergillus niger*, etc.). Prokaryotic cells include, for example, *E. coli* and *Bacillus*. Vectors can be introduced into host cell by calcium phosphate methods, DEAE dextran methods, methods using cationic liposome DOTAP (Boehringer Manheim), electroporation methods, lipofection methods, etc.

Furthermore, the present invention provides antibodies produced from the above host cells.

Furthermore, the present invention provides compositions comprising the above-mentioned antibody of the present invention and a pharmaceutically acceptable carrier.

As described below, the present invention strongly suggests that the following antibodies are promising candidates for therapeutic antibodies for preventing Alzheimer-like phenotypes:

the IR-003, IR-091, IR-099, IR-103, IR-130, and IR-148 antibodies. Memory deterioration has been shown to be related to synaptic dysfunction caused by soluble A beta oligomers (Klein W L, 2001, Trends Neurosci; and Selkoe D J, 2002, Science). Excessive accumulation and deposition of A beta oligomers may trigger the complicated downstream cascades that cause Alzheimer's disease. Thus, therapeutic intervention using a composition comprising an antibody or antigen-binding fragment of the present invention and a pharmaceutically acceptable carrier could be effective for blocking the pathologic cascades, and thus this could enable the treatment of Alzheimer's disease (WO2009/051220, WO2009/099176, U.S. Ser. No. 12/533,294, and U.S. Ser. No. 12/533,348).

The "treatment" or "prevention" of the present invention does not necessarily have complete therapeutic or preventive effects against organs or tissues exhibiting symptoms of disorders or diseases, but may have partial effects or effects of suppressing the progression of symptoms.

"Treatment of Alzheimer's disease" in the present invention means amelioration or suppression of the progression of a symptom of at least one symptom that may be caused by Alzheimer's disease, and examples include amelioration or suppression of cognitive impairment, amelioration or suppression of senile plaque formation, amelioration or suppression of synaptic dysfunction, and reduction or suppression of A beta accumulation in brain tissues, blood, or such. Herein, "cognitive impairment" includes, for example, memory impairment including long term/short term memory impairment, object recognition memory impairment, spatial memory impairment, and associative and emotional memory impairment. Herein, "prevention of Alzheimer's disease" means suppression of at least one symptom that may be caused by Alzheimer's disease, and includes suppression of development of cognitive impairment, suppression of senile plaque formation, suppression of development of synaptic dysfunction, suppression of A beta accumulation in brain tissues, blood, or such.

The present invention provides pharmaceutical compositions or pharmaceutical agents which comprise as an active ingredient a composition comprising the above-described antibody or antigen-binding fragment of the present invention and a pharmaceutically acceptable carrier. The above pharmaceutical compositions or pharmaceutical agents are expressed as "pharmaceutical compositions or pharmaceutical agents comprising the above-described antibody or antigen-binding fragment of the present invention as an active ingredient, and a pharmaceutically acceptable carrier".

In the present invention, the phrase "comprising as an active ingredient a composition comprising the above-described antibody or antigen-binding fragment of the present invention and a pharmaceutically acceptable carrier", and "comprising the above-described an antibody or antigen-binding fragment as an active ingredient" mean comprising a composition comprising the above-described antibody or antigen-binding fragment of the present invention and a pharmaceutically acceptable carrier, or the above-described antibody or antigen-binding fragment of the present invention as a major ingredient or a component that shows physiological activity or pharmacological function, but does not limit its content rate.

Examples of the above-mentioned pharmaceutical compositions include agents against cognitive impairment, Alzheimer's disease therapeutic agents, agents for suppressing the progression of Alzheimer's disease, agents for suppressing senile plaque formation, agents for suppressing A beta accumulation, anti-neurotoxic agents (agents for neutralizing neurotoxicity), agents for inhibiting A beta amyloid fibril formation, and anti-synaptic toxicity agents (agents for neutralizing synaptic toxicity).

The above-mentioned pharmaceutical composition of the present invention can be expressed, for example, as "methods for suppressing Alzheimer's disease" which comprise the step of administering to a subject (individual) a composition comprising the above-described antibody or antigen-binding fragment of the present invention and a pharmaceutically acceptable carrier. Alternatively, it can be expressed, for example, as "methods for suppressing Alzheimer's disease" which comprise the step of administering to a subject a therapeutically effective amount of the above-described antibody or antigen-binding fragment of the present invention. In other embodiments, examples include methods for suppressing cognitive impairment, methods for suppressing the progression of Alzheimer's disease, methods for suppressing senile plaque formation, methods for suppressing A beta accumulation, methods for neutralizing (suppressing) neurotoxic activity, methods for inhibiting A beta amyloid fibril formation, and methods for neutralizing (suppressing) synaptic toxicity. In further embodiments, examples include methods for preventing and/or treating cognitive impairment, and methods for preventing and/or treating Alzheimer's disease.

The present invention also provides use of a composition comprising the above-described antibody or antigen-binding fragment of the present invention and a pharmaceutically acceptable carrier for the manufacture of the above-mentioned pharmaceutical composition. The present invention further provides use of the above-described antibody or antigen-binding fragment of the present invention for the manufacture of the above-described pharmaceutical composition.

Furthermore, the present invention relates to the following antibodies or antigen-binding fragments.

The above-described antibody or antigen-binding fragment of the present invention for use in preventing and/or treating cognitive impairment.

The above-described antibody or antigen-binding fragment of the present invention for use in preventing and/or treating Alzheimer's disease.

The above-described antibody or antigen-binding fragment of the present invention for use in suppressing the progression of Alzheimer's disease.

The above-described antibody or antigen-binding fragment of the present invention for use in suppressing senile plaque formation.

The above-described antibody or antigen-binding fragment of the present invention for use in suppressing A beta accumulation.

The above-described antibody or antigen-binding fragment of the present invention for use in neutralizing (suppressing) neurotoxic activity.

The above-described antibody or antigen-binding fragment of the present invention for use in inhibiting A beta amyloid fibril formation.

The above-described antibody or antigen-binding fragment of the present invention for use in neutralizing (suppressing) synaptic toxicity.

The present invention also relates to the following:

Use of the above-described antibody or antigen-binding fragment of the present invention for preventing and/or treating cognitive impairment.

Use of the above-described antibody or antigen-binding fragment of the present invention for preventing and/or treating Alzheimer's disease.

Use of the above-described antibody or antigen-binding fragment of the present invention for suppressing the progression of Alzheimer's disease.

Use of the above-described antibody or antigen-binding fragment of the present invention for suppressing senile plaque formation.

Use of the above-described antibody or antigen-binding fragment of the present invention for use in suppressing A beta accumulation.

Use of the above-described antibody or antigen-binding fragment of the present invention for neutralizing (suppressing) neurotoxicity.

Use of the above-described antibody or antigen-binding fragment of the present invention for inhibiting A beta amyloid fibril formation.

Use of the above-described antibody or antigen-binding fragment of the present invention for neutralizing (suppressing) synaptic toxicity.

The above-mentioned pharmaceutical compositions or agents of the present invention can be administered to humans or other animals. In the present invention, non-human animals to which the pharmaceutical compositions or agents are administered include mice, rats, guinea pigs, rabbits, chickens, cats, dogs, sheep, pigs, cattle, monkeys, baboons, and chimpanzees. These animals preferably exhibit at least one symptom selected from, for example, cognitive impairment, senile plaque formation, synaptic dysfunction, A beta accumulation in brain tissues or blood, etc.

Antibodies or antigen-binding fragments contained in the pharmaceutical compositions of the present invention are not particularly limited as long as they are included in the above-mentioned antibodies or antigen-binding fragments of the present invention, and examples include the antibodies or antigen-binding fragments described herein.

When using the above-mentioned antibodies or antigen-binding fragments of the present invention for pharmaceutical compositions, they may be formulated by methods known to those skilled in the art. For example, as necessary, they can be prepared in the form of injectable sterile solutions or suspensions using water or another pharmaceutically acceptable liquid, and can be administered parenterally. For example, the antibodies or antigen-binding fragments to be included in the pharmaceutical compositions can be combined with pharmaceutically acceptable carriers or media, specifically, sterile water, physiological saline, vegetable oils, emulsifiers, suspensions, surfactants, stabilizers, flavoring agents, excipients, solvents, preservatives, binders, or such, and mixed into a unit dose form required for generally accepted pharmaceutical practice. The phrase "pharmaceutically acceptable" indicates that the substance is inactive, and contains conventional substances used as diluents or vehicles for pharmaceuticals. Suitable excipients and their formulations are described, for example, in Remington's Pharmaceutical Sciences, 16th ed. (1980) Mack Publishing Co., ed. Oslo et al.

Physiological saline and other isotonic solutions containing glucose or adjuvants (for example, D-sorbitol, D-mannose, D-mannitol, and sodium chloride) can be used as aqueous solutions for injection. They can be used together with appropriate solubilizers such as alcohols, more specifically, ethanol and polyalcohols (propylene glycol, polyethylene glycol, and such), and non-ionic surfactants (Polysorbate 80™, HCO-50, and such).

Sesame oil or soybean oil can be used as an oleaginous liquid, and benzyl benzoate or benzyl alcohol can be used in combination as a solubilizer. Buffers (for example, phosphate buffer and sodium acetate buffer), soothing agents (for example, procaine hydrochloride), stabilizers (for example, benzyl alcohol and phenol), and antioxidants can be used for the formulations. Prepared injection solutions can be filled into appropriate ampules.

The administration is preferably parenteral administration, and specific examples include administration by injection, transnasal administration, transpulmonary administration, and transdermal administration. Examples of administration by injection include systemic and local administration by intravenous injection, intramuscular injection, intraperitoneal injection, subcutaneous injection, and such.

The pharmaceutical compositions contain a pharmaceutically effective amount or therapeutically effective amount of the active component (the above-mentioned antibody of the present invention). "Pharmaceutically effective amount (of a compound)" or "therapeutically effective amount" refers to an amount sufficient for treating and/or preventing disorders in which antigens for the above-mentioned antibodies of the present invention play an important role. For example, "a pharmaceutically effective amount" or "therapeutically effective amount" may be an amount required for reducing A beta accumulation, neutralizing A beta-induced toxicity, reducing A beta fibril formation, or such, thereby treating or preventing conditions caused by Alzheimer's disease, when the above-described antibody or antigen-binding fragment of the present invention is administered to individuals (patients). The reduction or neutralization may be, for example, a reduction or neutralization of at least approximately 5%, 10%, 20%, 30%, 40%, 50%, 75%, 80%, 90%, 95%, 99%, or 100%.

Assessment for determining such a pharmaceutically effective amount of the above-mentioned antibodies or antigen-binding fragments of the present invention may be carried out using a standard clinical protocol including histopathological diagnosis.

A suitable administration method may be selected depending on the age and symptoms of the patient. The dosage of an antibody-containing pharmaceutical composition may be selected, for example, within the range of 0.0001 mg to 1000 mg per kilogram body weight for each administration. Alternatively, for example, the dosage for each patient may be selected within the range of 0.001 to 100,000 mg/body; however, the dosage is not necessarily limited to these ranges. Although the dosage and administration methods vary depending on the patient's body weight, age, symptoms, and such, one skilled in the art can appropriately select them. The dosage may be selected based on the high-dose intravenous immunoglobulin therapy (400 mg/kg) covered by health insurance for humans.

In the present invention, the pharmaceutical compositions or agents comprising an antibody or antigen-binding fragment of the present invention may be included in products and kits containing materials useful for treating pathological conditions of a subject. The products may comprise any labeled container for a compound. Suitable containers include bottles, vials, and test tubes. The containers may be formed from a variety of materials such as glass and plastic. The label on the container surface should indicate that the composition is used to treat or prevent one or more conditions of the disease. The label may also indicate descriptions for administration, and such.

In addition to the above-mentioned container, a kit containing a pharmaceutical composition or agent comprising an antibody or antigen-binding fragment may optionally include a second container that stores a pharmaceutically acceptable diluent. The kit may further include other materials desirable from a commercial and user's standpoint, including other buffers, diluents, filters, needles, syringes, and package inserts with descriptions for use.

If necessary, the pharmaceutical compositions may be provided in a pack or dispenser device that may contain one or more unit dosage forms comprising an active ingredient. The pack may comprise metal or plastic foil, and, for example, it is a blister pack. The pack or dispenser device may be accompanied by instructions for administration.

In the above-mentioned pharmaceutical agents and kits, besides the antibody or antigen-binding fragment of the present invention that is an active ingredient, sterile water, physiological saline, vegetable oils, surfactants, lipids, solubilizing agents, buffers, protein stabilizers (BSA, gelatin, etc.), preservatives, blocking solutions, reaction solutions, reaction quenching solutions, reagents for treating samples, and such, may be mixed as necessary.

Furthermore, the present invention provides methods for detecting A beta oligomers (examples include A beta40 (A beta 1-40), A beta42 (A beta 1-42) oligomers, and A beta40/A beta42 oligomers) in samples (specimens). Examples of "samples" of the present invention include samples collected from subjects, cell culture supernatants, cell extracts, samples collected from subject animals, or such; however, they are not particularly limited as long as they contain A beta oligomers. Specifically, the present methods include the step of detecting A beta oligomers contained in a sample (e.g., a sample collected from a subject) using an antibody or antigen-binding fragment of the present invention. A beta oligomers in a sample can be detected by common immunological detection methods, for example, using ELISA (sandwich solid-phase enzyme immunoassay methods that use chemiluminescence (chemiluminescence ELISA), etc.), RIA, immunoprecipitation methods that use the obtained antibodies, immunoblotting, flow cytometry, mass spectrometry, and immunohistochemical analysis.

When A beta oligomers are detected in a sample collected from a subject by the above-mentioned measurement methods, the subject is a possible Alzheimer's disease patient (WO2009/051220, WO2009/099176, U.S. Ser. No. 12/533, 294, and U.S. Ser. No. 12/533,348). Thus, the present invention also provides methods of diagnosing whether a subject is a possible Alzheimer's disease patient. For example, when the amount of A beta oligomers in a sample collected from a subject is compared with that from a healthy individual, and if the amount of A beta oligomers is greater in the subject than in the healthy individual, the subject is determined to be a possible Alzheimer's disease patient. Whether or not a subject is a possible Alzheimer's disease patient is diagnosed usually by physicians (including individuals under instructions from physicians; same herein below). Data on the amount of A beta oligomers in samples collected from a subject and a healthy individual, which are obtained by the present methods of diagnosis, will be useful for diagnosis by physicians. Therefore, the present methods of diagnosis can be expressed as methods of collecting and presenting data useful for diagnosis by physicians. Furthermore, "a method of diagnosing whether or not a subject is a possible Alzheimer's disease patient" is alternatively expressed as "a method of diagnosing whether or not a subject suffers from Alzheimer's disease, or is at a risk of developing Alzheimer's disease".

Specifically, the present invention provides methods for diagnosing whether or not a subject is a possible Alzheimer's disease patient, wherein the methods comprise detecting A beta oligomers in a sample collected from the subject using an antibody or antigen-binding fragment of the present invention.

More specifically, the present invention provides a method of diagnosing whether or not a subject is a possible Alzheimer's disease patient, which comprises the steps of:

(a) contacting a sample collected from a subject with the antibody or antigen-binding fragment of the present invention; and (b) measuring the amount of A beta oligomer in the sample, wherein the subject is determined to be a possible Alzheimer's disease patient, when the amount measured in step (b) is higher than that of a healthy individual. Step (b) above can be alternatively expressed as "the step of detecting an A beta oligomer in the sample via the antibody or antigen-binding fragment of the present invention that has bound to an A beta oligomer in the sample".

Furthermore, the present invention provides methods of diagnosing whether or not a subject is a possible Alzheimer's disease patient, which comprise the steps of:

(a) contacting a sample collected from a subject with an antibody or antigen-binding fragment of the present invention and an antibody or antigen-binding fragment that binds to an A beta monomer; and (b) measuring the ratio of A beta oligomer to A beta monomer in the sample, wherein the subject is determined to be a possible Alzheimer's disease patient, if the ratio measured in step (b) is higher than that of a healthy individual.

First, in the present methods, a sample collected from a subject is contacted with an antibody or antigen-binding fragment of the present invention and an antibody or antigen-binding fragment that binds to an A beta monomer. Herein, "contact" may be carried out, for example, by adding each of the above-mentioned antibodies or antigen-binding fragments to a sample collected from a subject, which is placed in a test tube. In this case, the antibody or antigen-binding fragment is added suitably in the form of a solution, a solid obtained by freeze-drying, or such. When adding the antibody as an aqueous solution, the solution may purely contain the antibody alone, or may contain, for example, surfactants, excipients, coloring agents, flavors, preservatives, stabilizers, buffers, suspending agents, tonicity agents, binding agents, disintegrants, lubricants, fluidity promoters, or corrigents. The concentration at which the antibody is added is not particularly limited. For example, as with human immunoglobulin formulations, 500-mg, 1000-mg, and 2500-mg freeze-dried formulations and such may be suitably used. "Contact" may be performed, for example, by adding a sample to a carrier on which the above antibody or antigen-binding fragment has been immobilized. Preferred examples of the carrier on which the above antibody or antigen-binding fragment is immobilized include, for example, microplates, beads (magnetic beads, Sepharose beads, etc.

Next, the ratio of A beta oligomer to A beta monomer (herein, this is also referred to as "O/M index") in the aforementioned sample is measured. To measure this ratio, the measurement can be carried out using a method of comparing the oligomer and monomer ELISA values obtained from the same sample.

Then, this ratio is compared with the ratio for a healthy individual. When the ratio is higher in the subject than in the healthy individual, the subject is determined to be a possible Alzheimer's disease patient.

The methods of diagnosis of the present invention can be performed both in vitro and in vivo, but they are preferably performed in vitro.

Preferably, the "sample collected from a subject" of the present invention is not particularly limited as long as it is a tissue derived from a subject. Examples include the brain (brain parenchyma, and such), organs, and body fluids (blood, cerebrospinal fluid, and such) of a subject. In the present invention, the sample is preferably blood (more preferably, plasma) or cerebrospinal fluid. The "sample collected from a subject" includes a sample treated with an enzyme, treated using a column, treated by centrifugation, treated by extraction, after collection.

When the sample is a brain tissue, frozen tissue samples from the brain tissue may be homogenized and subjected to ultracentrifugation or such, to separate buffer-soluble fractions and buffer-insoluble fractions and measure A beta oligomers. For example, a brain tissue is homogenized in nine volumes of Tris-buffered saline (TS) containing a protease inhibitor cocktail, and the homogenates are ultracentrifuged at 265,000×g for 20 minutes. Then, a collected supernatant as a soluble fraction of the brain tissue can be used as a sample for immunoblotting, ELISA, RIA, immunoprecipitation, etc.

A buffer-insoluble fraction may be solublized by formic acid (e.g., 70%) extraction, and used as a sample for immunoblotting, ELISA, RIA, immunoprecipitation, etc. Formic acid extracts may be appropriately neutralized or diluted with a buffer (e.g., 1 M Tris-HCl (pH 8.0)).

When A beta oligomers present in a brain tissue are visualized and measured by immunohistochemical methods, brain tissue sections from a subject can be used as samples. To enhance the immunoreactivity, the brain tissue sections can be pre-treated with Protease K. In immunohistochemical methods, it is not essential to quantify A beta oligomers in brain tissues. For example, if A beta deposition is observed, the subject is determined to be a possible Alzheimer's disease patient.

To increase the accuracy of A beta oligomer measurements, lipoproteins may be removed from a subject-derived sample. The depletion of lipoproteins can be performed by, for example, combining ultracentrifugation, ultrafiltration, and affinity chromatography. A specific method of depleting lipoproteins from a sample is exemplified below, but not limited thereto.

The density of a sample is adjusted to 1.25 g/ml with KBr. The sample is ultracentrifuged at 100,000 rpm and 16 degrees C. for eight hours. Lipoproteins floating at a density of 1.25 g/ml and lipoprotein-depleted clarified fluid are subjected to ultrafiltration using a 3 kDa cut-off membrane (Microcon 3; Amicon, Inc), and then frozen and stored, or stored at 4 degrees C., until use. Lipoproteins are also removed by affinity chromatography using PHML-LIPOSORB (Calbiochem, La Jolla, Calif.). A sample and PHML-LIPOSORB (Calbiochem, La Jolla, Calif.) are combined at a ratio of 1.5:1, and mixed for 60 seconds. Then, the mixture is centrifuged at 3,000 rpm for ten minutes. The resulting supernatants can be used as lipoprotein-free samples. The lipoprotein-bound samples bound to PHML-LIPOSORB are eluted using 20 mM sodium deoxycholate. The removal of specific lipoproteins can be confirmed by 1% agarose gel electrophoresis, followed by staining with FAST-RED 7B (Wako, Osaka, Japan).

Furthermore, by size fractionation of A beta oligomers in a sample using size exclusion chromatography, ultrafiltration, or such, and subsequent detection of A beta oligomers in each fraction using the antibody or antigen-binding fragment of the present invention, the amount of A beta oligomer of each size in the sample can be measured. Fractionation by size exclusion chromatography can be performed by concentrating a subject-derived sample about ten-fold using a Microcon 3 kDa molecular weight cut-off filter (Millipore Corp.), and then applying the sample to a Superose 12 size exclusion column (1 cm×30 cm; Pharmacia Biotech., Uppsala, Sweden; flow rate of 0.5 ml/min) equilibrated with a phosphate buffer. Alternatively, fractionation by ultrafiltration can be performed by sequential ultrafiltration using Microcon 3 kDa, 10 kDa, 30 kDa, and 100 kDa cut-off membranes. The amount of A beta oligomer contained in each fraction can be measured by ELISA, RIA, immunoblotting, immunoprecipitation, etc.

The methods of measuring an A beta oligomer of the present invention are not particularly limited as long as they comprise the step of detecting an A beta oligomer in a sample using the antibodies or antigen-binding fragments of the present invention. Preferable methods include sandwich ELISA. When sandwich ELISA is performed, an antibody or antigen-binding fragment of the present invention may be immobilized or labeled. Alternatively, an antibody or antigen-binding fragment of the present invention may be used as a primary antibody, and a labeled secondary antibody can be bound to it. The other antibody used in sandwich ELISA may be an antibody or antigen-binding fragment of the present invention, or may be a commercially available anti-A beta antibody. A specific method of detecting A beta oligomers in a sample by sandwich ELISA is exemplified below, but not limited thereto.

Microplates are coated with an antibody or antigen-binding fragment of the present invention, and 100 micro 1 of a sample is added and incubated continuously for 24 hours at 4 degrees C. Then, horseradish peroxidase-conjugated BA27 Fab' fragment (anti-A beta 1-40 specific to A beta 40; Wako pure chemical, Osaka, Japan) or horseradish peroxidase-conjugated BCO5 Fab' fragment (anti-A beta 35-43 specific to A beta 42; Wako pure chemical, Osaka, Japan) is added and incubated at 4 degrees C. for 24 hours. The chemiluminescence generated using SuperSignal ELISA Pico Chemiluminescent Substrate (Pierce, Rockford, Ill., USA) is quantified by a Veritas Microplate Luminometer (Promega).

Furthermore, if a sample is immunoprecipitated using an antibody of the present invention, and then immunoblotting analysis is performed, the size of A beta oligomer contained in a sample can be identified without carrying out size fractionation by size exclusion chromatography, ultrafiltration, or such. A specific method is exemplified below, but not limited thereto.

Immunoprecipitation is conducted by incubating a sample with an antibody of the present invention and Protein G-Sepharose. The immunoprecipitated A beta oligomers are separated using an NuPAGE 4-12% Bis-Tris-Glycine gel, and transferred onto a nitrocellulose membrane or Immobilon P (Millipore) using 10 mM 3-cyclohexylamino-1-propane sulfonic acid (pH 11) containing 10% methanol at 400 mA for one hour. Non-specific binding sites on the membrane were blocked with a phosphate buffer containing 5% low-fat milk, 1% BSA, and 0.05% Tween-20 at room temperature for three hours. The A beta oligomers are detected by reaction with an antibody of the present invention, or a commercially available anti-A beta antibody such as 4G8 or 6E10 (Covance Immuno-Technologies, Dedham, Mass.).

Furthermore, to quantify the amount of A beta oligomer in a sample, a calibration curve may be prepared using standard samples containing a known concentration of A beta oligomer. A beta oligomers used for preparation of standard samples can be prepared by diluting a synthetic A beta (HCl form) dissolved in an HCl solution with PBS or such to a suitable concentration (e.g., 0.1 mg/ml), and incubating at 37 degrees C. for an hour. The incubation temperature and time for synthetic A beta can be suitably selected. In the methods of the present invention, to obtain the ratio of A beta oligomer to A beta monomer, a calibration curve may be also prepared for A beta monomers. A beta monomers used for preparation of standard A beta monomer samples can be prepared by diluting a synthetic A beta (TFA form) dissolved in TFA (trifluoroacetic acid) with PBS or such to a suitable concentration (e.g., 0.1 mg/ml). For synthetic A beta, A beta 1-40, A beta 1-42, or such can be used.

Furthermore, the present invention provides agents (reagents) or kits for use in the above-mentioned methods of measuring A beta oligomers in a sample, or methods of diagnosing whether or not a subject is a possible Alzheimer's disease patient.

The agents for use in the above-mentioned methods of measuring A beta oligomers, or methods of diagnosing whether or not a subject is a possible Alzheimer's disease patient include agents comprising an antibody or antigen-binding fragment of the present invention. In a preferred embodiment, the agents include antibody solutions and immobilized antibodies; however, they are not limited thereto. When the agents are in a form of antibody solution, an antibody or antigen-binding fragment of the present invention is being dissolved in a suitable solvent. Those skilled in the art can select suitable solvents for dissolving the antibody or antigen-binding fragment of the present invention such as water, physiological saline, phosphate buffer, Tris buffer, etc. The above antibody solution of the present invention may comprise, in addition to an antibody of the present invention, a buffer, protein stabilizing agent, preservative agent, blocking agent, surfactant, solubilizing agent, or such, as necessary.

When the agent of the present invention is an immobilized antibody, the antibody or antigen-binding fragment of the present invention is being carried by a suitable carrier. Examples of the carrier include microplates, beads (magnetic beads, Sepharose beads, etc.), nitrocellulose membranes, and such; however, they are not limited thereto. Those skilled in the art can select suitable carriers for immobilizing the antibodies of the present invention. Antibodies or antigen-binding fragments of the present invention can be bound to carriers using known methods.

Antibodies or antigen-binding fragments of the present invention comprised in the agents may be suitably labeled with an enzyme label, radioactive label, fluorescent label, dye label, chemical luminescence label, etc.

The kits for use in the above-mentioned methods of measuring A beta oligomers, or methods of diagnosing whether or not a subject is a possible Alzheimer's disease patient include kits comprising agents comprising an antibody or antigen-binding fragment of the present invention. Preferable examples of agents comprising an antibody or antigen-binding fragment of the present invention are as mentioned above. The kits may comprise an antibody or antigen-binding fragment of the present invention in a form of lymphilized powder. In this case, kit users dissolve the lymphilized powder of antibody or antigen-binding fragment with a suitable solvent. The kits may comprise such a solvent for dissolving the antibody or antigen-binding fragment. The kits further comprise a dilution solution for diluting the above-mentioned antibody solutions.

The kits may comprise, in addition to an agent comprising an antibody or antigen-binding fragment of the present invention, a reagent such as blocking agent, chromogenic reagent, chromogenic substrate, reaction termination solution, washing solution, buffer, primary antibody, secondary antibody, or such, as necessary. Those skilled in the art can select a suitable reagent depending on the A beta oligomer measurement method. For example, a sandwich ELISA kit comprising a microplate on which the antibody is immobilized may further comprise a labeled anti-A beta antibody, chromogenic substrate, reaction termination solution, washing solution, plate seal, etc. Furthermore, in a sandwich ELISA kit comprising an antibody solution of the present invention may further comprise a microplate on which an anti-A beta antibody is immobilized, chromogenic substrate, reaction termination solution, washing solution, plate seal, labeled secondary antibody (if the antibody of the present invention is not labeled), etc.

The kits may further comprise a standard sample for preparing a calibration curve of A beta oligomer. The standard sample may be a solution containing a known concentration of A beta oligomer. The kits may comprise a diluting solution for stepwise dilution of the standard solution. Alternatively, lymphilized powder of A beta oligomers may be included, and a solvent for dissolving the lymphilized powder may be comprised. Furthermore, the kits may comprise a solution or lymphilized powder of an A beta monomer, and kit uses may prepare an A beta oligomer standard solution by incubating the A beta monomer solution to polymerize A beta monomers.

When the kits are for use in methods of diagnosing whether or not a subject is a possible Alzheimer's disease patient, they may comprise a sample (a brain tissue, cerebrospinal fluid, blood, plasma, etc.) collected from a healthy individual as a negative control, and a sample collected from a AD brain patient as a positive control.

The kit may further include other materials desirable from a commercial and user's standpoint, including buffers, diluents, filters, needles, syringes, and attached documents including descriptions for use (instructions, CD-ROM, etc.). These agents and such contained in the kit may be included in a container with a label. Such a container includes a bottle, vial, test tube, microtube, etc.

All prior art references cited herein are incorporated by reference into this description.

EXAMPLES

Hereinbelow, the present invention is specifically described with reference to the Examples, but it is not to be construed as being limited thereto.

Methods

Preparation of Antigens

A fluorescent dye, 6-carboxytetramethylrhodamine (6-TAMRA) (SIGMA) was chemically linked to the N terminus of a synthetic A beta 1-40 peptide (Peptide Institute, Inc.) to produce a modified A beta. An oligomer-rich sample (A beta 1-40 oligomer) was prepared by copolymerizing the modified A beta and synthetic A beta 1-40 peptide. It is preferable to adjust the conditions so that the fluorescence intensity determined by ThT assay (Yamamoto N, et al: J Biol Chem, 282: 2646-2655, 2007), which is described below, is one-fourth or less the fluorescence intensity in the absence of a modified A beta. More specifically, it is preferred that 100 micro M each of the modified A beta and synthetic A beta 1-40 peptide are mixed, and polymerized for 20 hours.

Preparation of Antibody-Producing Hybridomas

BALB/c mice were immunized by injecting the antigen prepared by the method described above into their foot pads or abdominal cavities. Then, booster immunization was carried out six times. Hybridomas were prepared from inguinal lymph node cells or spleen cells by fusion with Sp2/O—Ag14 cells using Polyethylene Glycol 1500.

ELISA Screening (Primary Screening)

Hybridoma culture supernatants were added to ELISA plates immobilized with A beta oligomers and reacted. Color development was carried out using an HRP-conjugated anti-mouse IgG antibody and TMB solution. A beta oligomers used in this method is A beta1-40 (HCl form) after one hour incubation or above-described extracted antigens of A beta1-42 tetramer.

Dot Blot Analysis (Secondary Screening)

Dot blot analysis was carried out for hybridomas that gave positive result for primary screening. In this analysis, 0.1 micro g/dot of three types of A beta; synthesized A beta 1-40 (TFA form) as A beta monomer, synthesized A beta1-40 (HCl form) after 1 hour incubation as A beta oligomer, and synthesized A beta1-42, were immobilized onto nitrocellulose membrane and used. The membrane was blocked with Tris Buffer containing 5% low-fat milk and 0.05% Tween-20, and reacted with hybridoma culture supernatants and detected using an HRP-conjugated anti-mouse IgG antibody and a chemiluminescence kit (ECL).

Antibody Isotyping

Isotyping of purified immunoglobulins were carried out using a Serotec (Oxford, UK) Mouse Monoclonal Antibody Isotyping Test Kit.

Identification of Antibody Sequences

RNAs were purified from hybridomas ($1 \times 10^6$ cells) produced by the method described above using FastPure RNA Kit (TaKaRa, Japan). Using the RNAs as templates, cDNAs were synthesized using 5' RACE System (Invitrogen, USA) and primers specific to H chains or L chains of antibodies that are produced from each hybridomas. 3' side primer sequences that were used for cDNA syntheses are shown below.

```
H chain (G1) mIGC1Rv:
                                        (SEQ ID NO: 131)
AAGGCTTACAACCACAATCCCT H chain (G2a) mIGC2aRv:
                                        (SEQ ID NO: 132)
TGCTGGGCATTTGCATGGA H chain (G2b) mIGC2bRv:
                                        (SEQ ID NO: 133)
TGGGCATTTGTGACACTCC H chain (G3) mIGC3Rv:
                                        (SEQ ID NO: 134)
ACTGGGCTTGGGTATTCTAGG L chain (kappa) mIKCNRv1:
                                        (SEQ ID NO: 135)
GTCCAACTGTTCAGGACGCCATTTTGTCGTT L chain (lambda) mILCNRv1:
                                        (SEQ ID NO: 136)
TCCACAGTGTGACCTTCATGAGTGACC
```

Furthermore, using the cDNAs, VH and VL regions were amplified by PCR method. 3' side primer sequences specific to H chains or L chains used for PCR are shown below.

```
H chain mIGCNRv:
                                        (SEQ ID NO: 137)
ACAGGGATCCAGAGTTCCA L chain (kappa) mIKCNRv2:
                                        (SEQ ID NO: 138)
TAACTGCTCACTGGATGG L chain (lambda) mILCNRv2:
                                        (SEQ ID NO: 139)
AGTGTGGCCTTGTTAGTCTCGAGC
``` cDNA syntheses and PCR were carried out according to the manual attached to the product, and primers attached to the product (AAP: GGCCACGCGTCGACTAGTACGGGGGGGGGG (SEQ ID NO: 140), AUAP: GGCCACGCGTCGACTAGTAC (SEQ ID NO: 141)) were used as 5' side primers. Taq DNA polymerase High Fidelity (Invitrogen, USA) was used for PCR.

VH and VL region fragments amplified by PCR was ligated with linear vector (pGEMTM-T Easy Vector (Promega, USA)) for one hour and transformed into *E. coli* DH5 alpha strain. Formed colonies were cultured overnight in a liquid selection medium and plasmids were purified using High Purity Plasmid Miniprep System (MARIGEN BIOSCIENCES, USA). Antibody sequences were determined by gene sequence analysis using BigDye Terminator V3.1 Cycle Sequence Kit (Applied Biosystems) and 3730x1 DNA Analyzer (Applied Biosystems). Two primers described below were used for sequence analysis.

```
                                        (SEQ ID NO: 142)
SP6: CGCCAGGGTTTTCCCAGTCACGAC (SEQ ID NO: 143)
M13Rv: TCACACAGGAAACAGCTATGAC
```

Control Antibodies

Anti-A beta antibody 6E10 was used as a control antibody to compare to the antibodies of the present invention. Anti-A beta antibody 6E10 (Covance Immuno-Technologies, Dedham, Mass.) is a mouse monoclonal antibody that recognizes a sequence in A beta1-16 as an epitope, and has no selectivity against A beta oligomer (binds to A beta monomer).

Competitive ELISA

A beta oligomer antigens were prepared by diluting synthetic A beta1-40 (HCl form) at 0.1 mg/ml with PBS and incubating at 37 degrees C. for one hour. A beta monomer was prepared by diluting synthetic A beta1-40 (TFA form) at 0.1 mg/ml with PBS. First, 400 ng/well of A beta oligomer was immobilized onto 96-well immunoplate and the plate was blocked with BSA. Next, antibodies of the present invention or a control anti-A beta antibody (6E10) were each mixed with serially-diluted A beta monomer or A beta oligomer at a range of 100 pg/ml to 100 micro g/ml and incubated for two hours, then each mixture was added to 96-well immunoplate and incubated at room temperature for ten minutes. Binding abilities of each antibodies to immobilized A beta oligomer were detected by reacting with HRP-conjugated anti-mouse IgG antibody and visualized by measuring absorbance at 450 nm using TMB solution. In the present method, two types of A beta1-40 (A beta1-40 monomer and A beta1-40 oligomer), which have the same sequence but have different structure and polymerization characters due to their structure, was compared as competitive substance. Accordingly, the method can compare the binding difference of the antibodies only derived from the existence of A beta1-40 polymerization, and thus can obtain extremely reliable results.

Analysis of Affinity to A Beta Oligomer

The analysis was carried out by Surface Plasmon Resonance (SPR) using Biacore 3000 (GE Healthcare Sciences). A beta oligomer was immobilized onto a sensor chip (CM5) as a ligand and antibodies of the present invention and control 6E10 antibody were used as analyte, kinetics analysis was carried out. Analysis was conducted at analyte antibodies at the following five concentrations: 1.25, 2.50, 5.00, 10.00, and 20.00 micro g/ml, and association rate constant (ka), dissociaton rate constant (kd), and dissociation constant (KD) was calculated using BiaEvaluation software. A beta oligomer used in the analysis was prepared by diluting synthetic A beta1-40 (HCl form) at 0.1 mg/ml with PBS and incubating at 37 degrees C. for one hour.

A Beta-Induced Neurotoxicity Assay

Human neuroblastoma cell (SH-SY5Y cell) was plated into 24-well plates at a density of 150,000 cells/well, and cultured for 24 hours in DMEM containing 10% FBS. Then, the medium was replaced a serum-free medium containing 12.5 micro M A beta1-42 in the presence or absence of antibodies and cells were cultured for another 24 hours. To determine the cytotoxicity induced by A beta1-42, LDH contents released into the medium from dead cells was determined using CytoTox96 Kit (manufactured by Promega).

Activity of Suppressing A Beta Amyloid Fibril Formation

A beta1-42 solution diluted to 12.5 micro M with cell culture medium was incubated in the presence or absence of antibodies of the present invention at 37 degrees C. for 24 hours. Then, the solutions were mixed with Thioflavin T (ThT) solution (5 micro M ThT, 50 mM Glycine-NaOH, pH8.5), ThT fluorescence intensity, which is correlated with A beta amyloid fibril contents, were determined using fluorescence spectrophotometer (RF-5300PC; Shimadzu Co., Kyoto, Japan). Excitation and emission wavelengths were set at 446 nm and 490 nm, respectively. Fluorescence intensity was measured immediately after the mixture was prepared.

Immunoblotting

Brain homogenates of Tg2576 or wild type mice were used for APP binding assay. The homogenates were electrophoresed in NuPAGE Tris-Glycine 4-12% gel and transferred to a PVDF membrane. The membrane was reacted to each antibody after blocking by PVDF blocking reagent (TOYOBO). The binding ability was detected by an HRP-conjugated anti-mouse IgG antibody and a chemiluminescent regent (Immobilon western, Millipore).

Result

Selection of Anti-A Beta Olilgomer Antibodies 46 mice were immunized with A beta 1-40 oligomer antigen and inguinal lympho node or spleen were isolated from each mice. Cells derived from each organs were fused with myeloma (Sp2/O—Ag14) and dispensed into seven plates of 96-well plate per mice and cultured. Hybridomas producing the antibodies of interest were selected by adding culture supernatant from the 96-well plate onto ELISA plates immobilized with A beta oligomer, and reacting them to analyze. As a result, 507 positive cells were selected from 30,912 wells ((46 mice)×(7 plates)×(96 wells)).

The above-described ELISA screening also select antibodies that do not specifically bind to A beta oligomer (antibodies that bind to ELISA plate other than A beta oligomer). By performing dot blot analysis, these non-specific antibodies can be excluded. Accordingly, dot blot analysis using ELISA-positive cells were carried out. For dot blot analysis, two types of oligomers and A beta monomer were spotted and excluded non-specific antibodies (antibodies that do not bind to the spotted A beta oligomer were excluded), as well as specificity against A beta oligomer (absence of binding to A beta monomer) was confirmed. As a result, 6 positive antibodies among 507 ELISA-positive cells were selected (FIG. 1).

Identification of Antibody Sequences

The variable region sequences were analyzed by the above-mentioned method, for 6 antibodies (i.e., the IR-003, IR-091, IR-099, IR-103, IR-130, and IR-148) selected by the above dot blot analysis. As a result, the following nucleotide sequences of regions comprising VH CDR1, CDR2, and CDR3 were obtained:

SEQ ID NO: 1(IR-003), SEQ ID NO: 17(IR-091), SEQ ID NO: 33(IR-099), SEQ ID NO: 49(IR-103), SEQ ID NO: 65(IR-130), and SEQ ID NO: 81(IR-148). From the above nucleotide sequence, the following amino acid sequences were obtained:

SEQ ID NO: 2(IR-003), SEQ ID NO: 18(IR-091), SEQ ID NO: 34(IR-099), SEQ ID NO: 50(IR-103), SEQ ID NO: 66(IR-130), and SEQ ID NO: 82(IR-148).

Furthermore, the following nucleotide sequences of regions comprising VL CDR1, CDR2, and CDR3 were obtained:

SEQ ID NO: 3(IR-003), SEQ ID NO: 19(IR-091), SEQ ID NO: 35(IR-099), SEQ ID NO: 51(IR-103), SEQ ID NO: 67(IR-130), and SEQ ID NO: 83(IR-148). From the above nucleotide sequence, the following amino acid sequences were obtained:

SEQ ID NO: 4(IR-003), SEQ ID NO: 20(IR-091), SEQ ID NO: 36(IR-099), SEQ ID NO: 52(IR-103), SEQ ID NO: 68(IR-130), and SEQ ID NO: 84(IR-148).

CDR sequences were determined from the amino acid sequences, based on the definition by Kabat (Kabat, Elvin A., Sequences of proteins of immunological interest 5th ed., National Institutes of Health, 1991). The CDR sequences of the antibodies are shown in Table 1. In Table 1, "Name" shows the name of each antibody, "class" shows the IgG subclass of each antibody, "chain" shows whether the chain is an H or L chain, and "(na)" means "nucleic acid".

TABLE 1

| Name | class | chain | CDR1 | SEQ ID NO | SEQ ID NO (na) | CDR2 | SEQ ID NO | SEQ ID NO (na) | CDR3 | SEQ ID NO | SEQ ID NO (na) |
|---|---|---|---|---|---|---|---|---|---|---|---|
| IR-003 | 2b | H | TS GMG VS | 6 | 5 | HI YWDD DKRYNPS LKS | 8 | 7 | RGEVRRRGYY AMDY | 10 | 9 |
|  |  | L | RS SQSLVHSNGNTYLH | 12 | 11 | KVSNRF S | 14 | 13 | SQSTHVPLT | 16 | 15 |
| IR-091 | 2b | H | TS GMG VG | 22 | 21 | HI WWDD DKYYNPS LKS | 24 | 23 | RGLRRGDYFDY | 26 | 25 |
|  |  | L | RS SQS I VHSNGNTY LE | 28 | 27 | KVSNRF S | 30 | 29 | FQGSHVPLT | 32 | 31 |
| IR-099 | 1 | H | RF GMH | 38 | 37 | YI SSGR STI YYA DTVKG | 40 | 39 | GGGNYVGAMDY | 42 | 41 |
|  |  | L | RS SQSLENSNGNTYLN | 44 | 43 | RVSNRF S | 46 | 45 | LQVTHVPPT | 48 | 47 |
| IR-103 | 2b | H | SF GMH | 54 | 53 | YI SSGS STI YYA DTVKG | 56 | 55 | SPLLRLQGLAY | 58 | 57 |
|  |  | L | RS SQS I VHSNGNTY LE | 60 | 59 | KVSNRF S | 62 | 61 | FQGSHVPPT | 64 | 63 |
| IR-130 | 2a | H | DY YMY | 70 | 69 | YI SNGG GST YYP DTVKG | 72 | 71 | GTSYGSSLHYY AMDY | 74 | 73 |
|  |  | L | RS SQSLVHSNGNTYLH | 76 | 75 | KVSNRF S | 78 | 77 | SQSTHVPLT | 80 | 79 |
| IR-148 | 2a | H | SF GMH | 86 | 85 | YI SSGS STI YYA DTVKG | 88 | 87 | DYYGMDY | 90 | 89 |
|  |  | L | RS SQSLVHSNGNTYLH | 92 | 91 | KVSNRF S | 94 | 93 | SQSTHVPLT | 96 | 95 |

Some of the obtained VH and VL sequences contained signal peptides or lacked N-terminal or C-terminal sequences. If sequences are lacked, they are supplemented. Thus, the VH and VL sequences without signal sequences were determined based on the homology with previously-reported antibody sequences.

The VH and VL amino acid sequences, excluding signal peptides, of each antibody are shown in Table 2.

The amino acid sequences of H-chain signal peptides of each antibody are shown in the following sequence ID numbers:

SEQ ID NO: 122(IR-003), SEQ ID NO: 124(IR-091), SEQ ID NO: 126(IR-099, IR-103, and IR-148), SEQ ID NO: 128 (IR-130). The nucleotide sequences encoding H-chain signal peptides of each antibody are shown in the following sequence ID numbers:

TABLE 2

| Name | chain | variable region | SEQ ID NO | SEQ ID NO (na) |
|---|---|---|---|---|
| IR-003 | H | QVTLKESGPGILQPSQTLSLTCSFSGFSLSTSGMGVSWIRQPSGKGLEWLAHIYWDDDKRYNPSLKSRLTISKDTSSNQVFLKITSVDTADTATYYCARRGEVRRRGYYAMDYWGQGTSVTVSS | 98 | 97 |
|  | L | DVVMTQTPLSLPVSLGDQASISCRSSQSLVHSNGNTYLHWYLQKPGQSPKLLIYKYSNRFSGVPDRFSGSGSGTDFTLKISRVEAEDLGVYFCSQSTHVPLTFGAGTKLELK | 100 | 99 |
| IR-091 | H | QVTLKESGPGILKPSQTLSLTCSFSGFSLSTSGMGVGWIRQPSGKGLEWLAHIWWDDDKYYNPSLKSQLTISKDTSRNQVFLKITSVDTADTATYYCARRGLRRGDYFDYWGQGTTLTVSS | 102 | 101 |
|  | L | DVLMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPLTFGAGTKLELK | 104 | 103 |
| IR-099 | H | DVQLVESGGGLVQPGGSRKLSCAASGFTFSRFGMHWVRQAPEKGLEWVAYISSGRSTIYYADTVKGRFTISRDNPKNTLFLQMTSLRSEDTAMYYCARGGGNYVGAMDYWGQGTSVTVSS | 106 | 105 |
|  | L | DAVMTQTPLSLPVSLGDQASISCRSSQSLENSNGNTYLNWYLQKPGQSPQLLIYRVSNRFSGVLDRFSGSGSGTDFTLKISRVEAEDLGVYFCLQVTHVPPTFGGGTKLEIK | 108 | 107 |
| IR-103 | H | DVQLVESGGGLVQPGGSRKLSCAASGFTFSSFGMHWVRQAPEKGLEWVAYISSGSSTIYYADTVKGRFTISRDNPKNTLFLQMTSLRSEDTAMYYCARSPLLRLQGLAYWGQGTLVTVSA | 110 | 109 |
|  | L | DVLMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPPTFGGGTKLEIK | 112 | 111 |
| IR-130 | H | EVKLVESGGGLVQPGGSLKLSCATSGFTFSDYYMYWVRQTPEKRLEWVAYISNGGGSTYYPDTVKGRFTISRDNAKNTLYLQMSRLKSEDTAMYYCARGTSYGSSLHYYAMDYWGQGTSVTVSS | 114 | 113 |
|  | L | DVVMTQTPLSLPVSLGDQASISCRSSQSLVHSNGNTYLHWYLQKPGQSPKLLIYKVSNRFSGVPDRFSGSGSGTDFTLKISRVEAEDLGVYFCSQSTHVPLTFGAGTKLELK | 116 | 115 |
| IR-148 | H | DVQLVESGGGLVQPGGSRKLSCAASGFTFSSFGMHWVRQAPEKGLEWVAYISSGSSTIYYADTVKGRFTISRDNPKNTLFLQMTSLRSEDTAMYYCARDYYGMDYWGQGTSVTVSS | 118 | 117 |
|  | L | DVVMTQTPLSLPVSLGDQASISCRSSQSLVHSNGNTYLHWYLQKPGQSPKLLIYKVSNRFSGVPDRFSGSGSGTDFTLKISRVEAEDLGVYFCSQSTHVPLTFGAGTKLELK | 120 | 119 |

SEQ ID NO: 121(IR-003), SEQ ID NO: 123(IR-091), SEQ ID NO: 125(IR-099, IR-103, and IR-148), SEQ ID NO: 127 (IR-130).

The amino acid sequences of L-chain signal peptides of each antibody are shown in the following sequence ID numbers:

SEQ ID NO: 130(IR-003, IR-091, IR-099, IR-103, IR-130, and IR-148). The nucleotide sequences encoding L-chain signal peptides of each antibody are shown in the following sequence ID numbers:

SEQ ID NO: 129(IR-003, IR-091, IR-099, IR-103, IR-130, and IR-148).

Competitive ELISA Analysis

Figure 2:
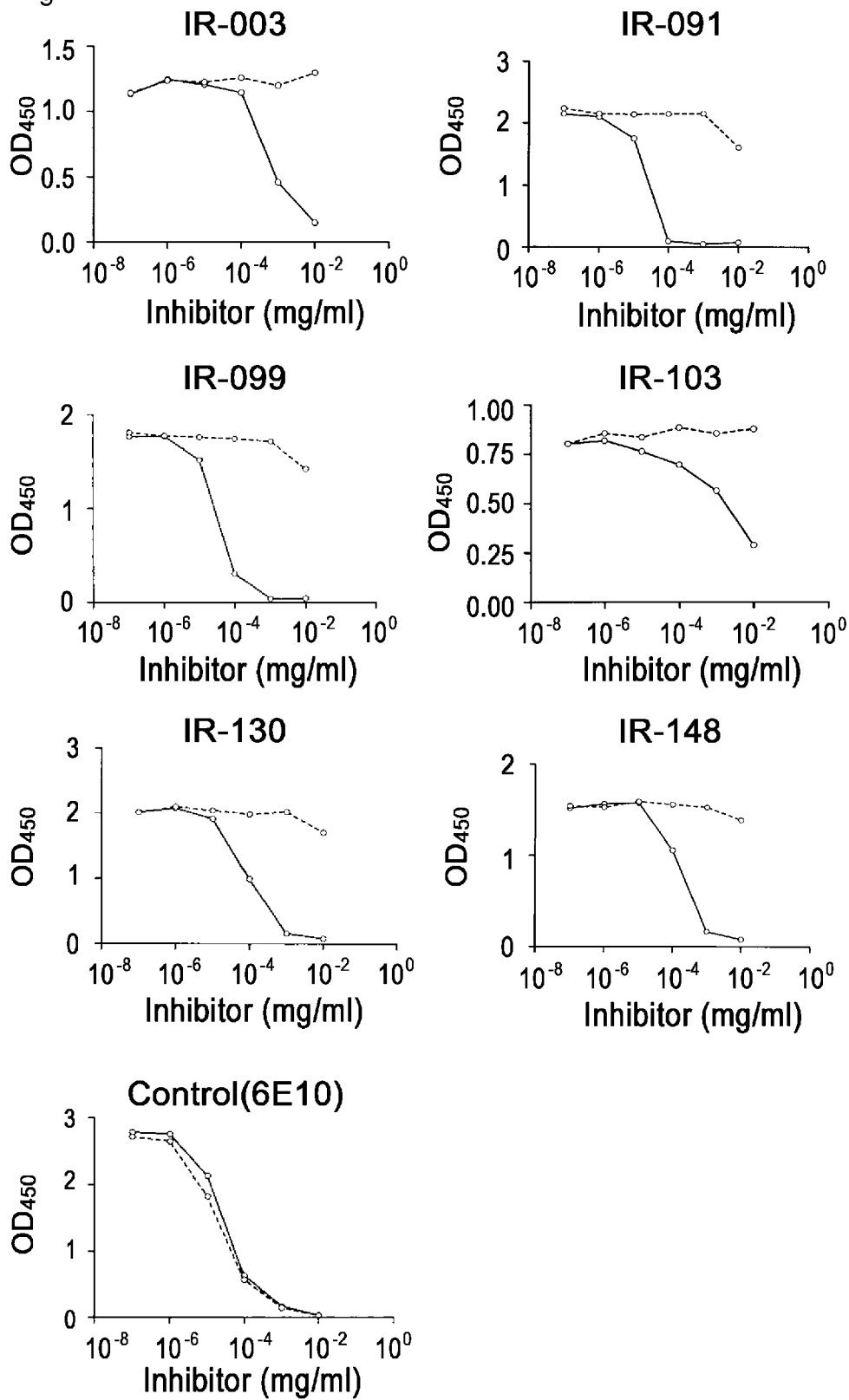
FIG. 2 presents competitive ELISA results on the six antibodies. The vertical axis shows the absorbance at a wavelength of 450 nm, and horizontal axis shows the concentration of A beta oligomer or monomer (mg/ml) used as an inhibitor. The dotted lines of each graph show the antigen binding activity when the A beta oligomer was used as an inhibitor. The solid lines of each graph show the antigen binding activity when the A beta monomer was used as an inhibitor.
Figure 3:
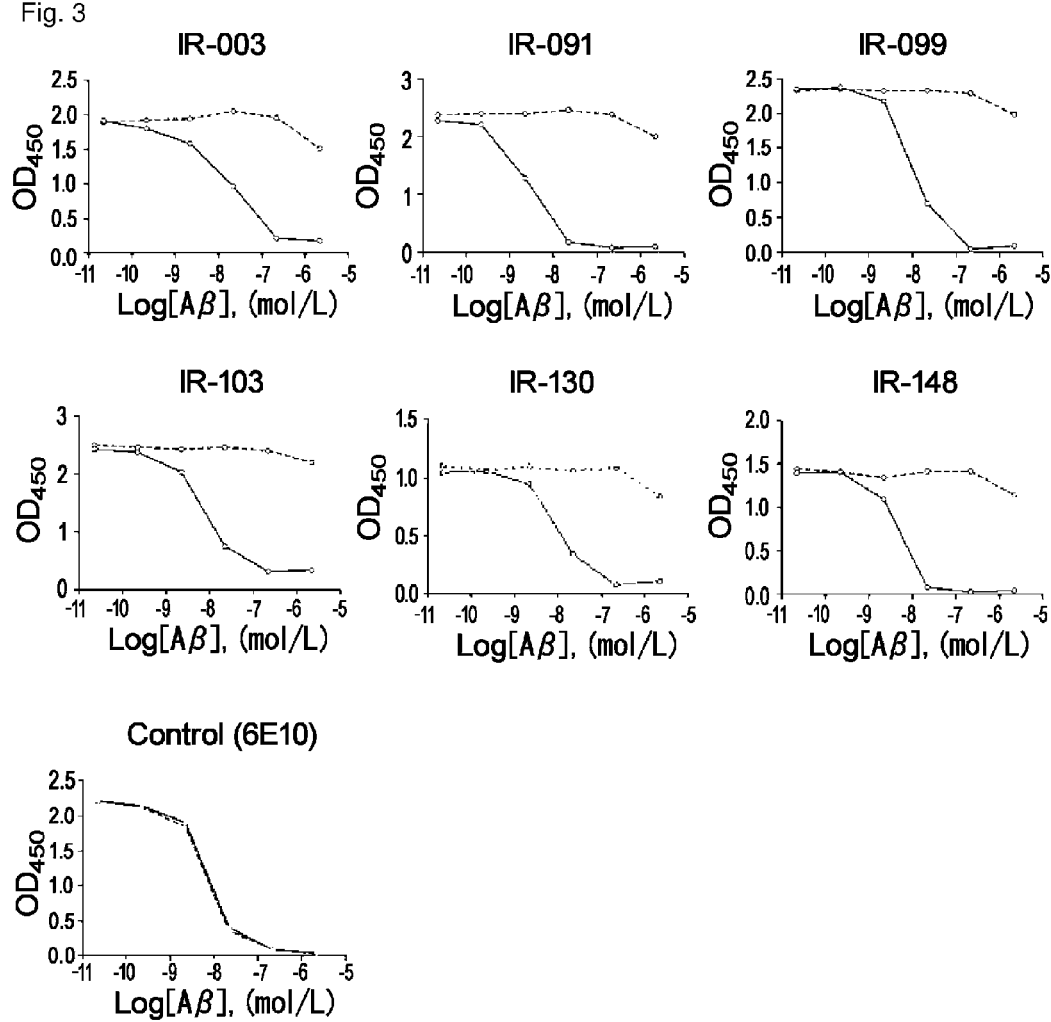
FIG. 3 presents competitive ELISA results on the six antibodies in which the inhibitor concentration is shown as molar concentration. The vertical axis shows the absorbance at a wavelength of 450 nm, and horizontal axis shows the molar concentration of A beta oligomer or monomer (mol/L) used as an inhibitor. The molar concentration (mol/L) of A beta oligomer was calculated by converting the molar number of A beta oligomer into that of A beta monomer.

Dot blot analysis is a method for analyzing a reactivity against A beta monomer or oligomer immobilized onto nitrocellulose membrane. However, A betas are solubilized into fluids such as interstitial fluid, cerebral fluid, or blood. Then, the present analysis was carried out for investigating specific binding to A beta oligomers in solutions and difference of selectivity to A beta monomer. Competitive ELISA is a method for determining oligomer specificity by preliminarily reacting with antibodies to be measured and serially-diluted A beta monomer or oligomer in solutions, and carrying out ELISA by adding the solutions to a plate immobilized with A beta oligomer. When an antibody is an A beta oligomer-specific antibody, ELISA reaction decreases in an A beta oligomer concentration-dependent manner in a solution reacted with A beta oligomer, but does not decrease in a solution reacted with A beta monomer or decreases when A beta concentration becomes higher than the oligomer concentration. The above six antibodies were analyzed and the result shown in FIG. 2 was obtained. All the antibodies showed high binding specificity even in the solution. Meanwhile, antibody that react with both A beta monomer and oligomer (6E10) used as a control showed equivalent ELISA reactivity against monomer and oligomer. Furthermore, the competitive ELISA results in which the inhibitor concentration is shown as molar concentration are shown in FIG. 3. $IC_{50}$ and A beta oligomer selectivity over A beta monomer (A beta monomer $IC_{50}$/A beta oligomer $IC_{50}$) calculated by the competitive ELISA in FIG. 3 are shown in Table 3.

TABLE 3

| Antibody | $IC_{50}$ (nmol/L) | | Selectivity |
|---|---|---|---|
| Name | monomer | oligomer | (vs monomer) |
| IR-003 | >2200 | 18.5 | >118.9 |
| IR-091 | >2200 | 2.54 | >866.1 |
| IR-099 | >2200 | 11.6 | >189.7 |
| IR-103 | >2200 | 7.5 | >293.3 |
| IR-130 | >2200 | 10.7 | >205.6 |
| IR-148 | >2200 | 4.04 | >544.6 |
| Control (6E10) | 6.84 | 7.58 | Q9 |

Analysis of Affinity for A Beta Oligomer

Figure 4:
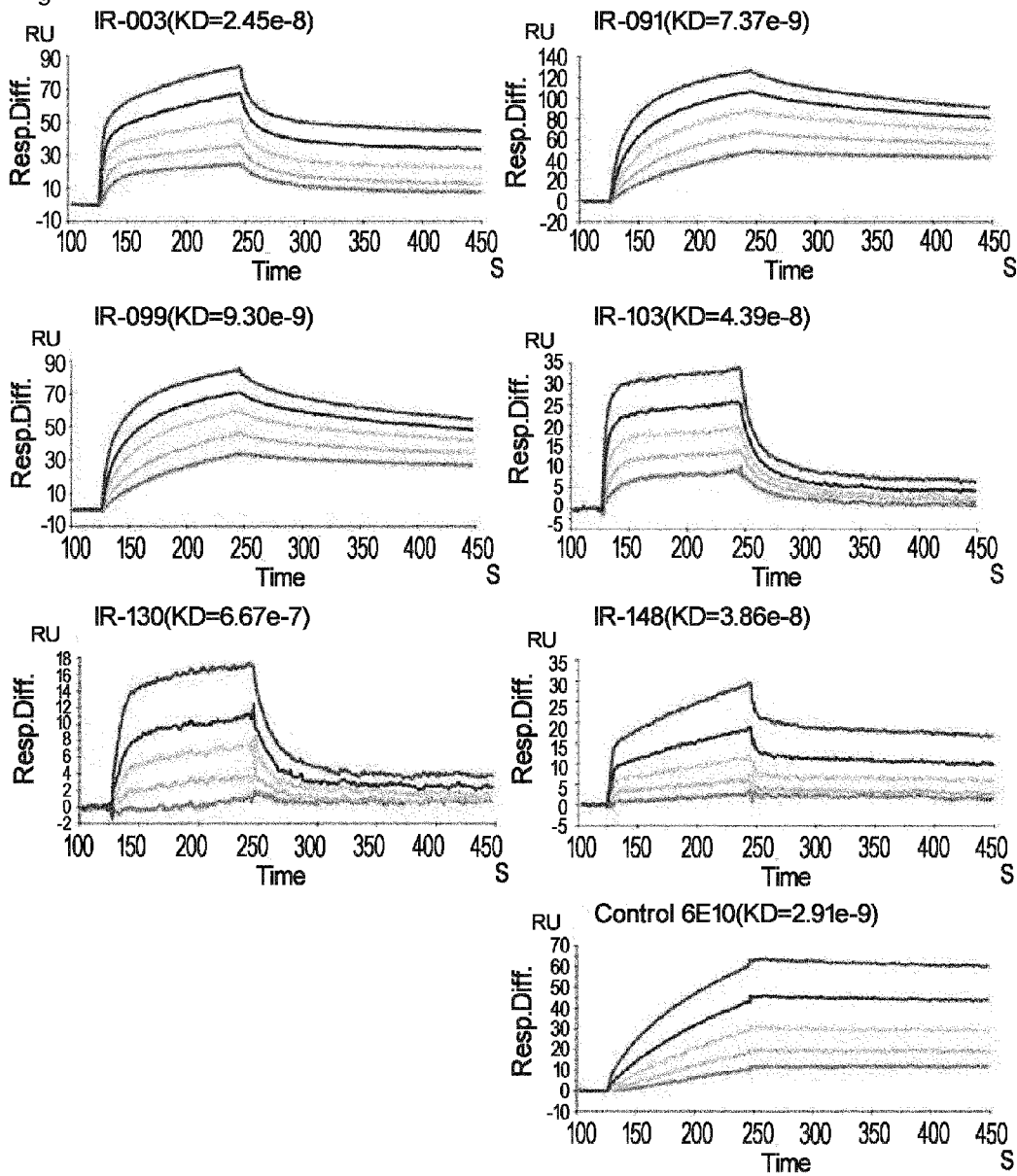
FIG. 4 shows the results of analysis of the affinity of the six antibodies to A beta oligomers, by Biacore 3000.

To investigate the binding ability of the antibodies of the present invention to A beta oligomer, affinity was analyzed (see Methods). The six antibodies were analyzed and results shown in FIG. 4 were obtained. Calculated association rate constant (ka), dissociation rate constant (kd), and dissociation constant (KD) was shown in Table 4.

TABLE 4

| Antibody | Kinetics assay | | |
|---|---|---|---|
| Name | ka ($M^{-1}s^{-1}$) | kd ($s^{-1}$) | KD = kd/ka (M) |
| IR-003 | 9.48E+04 | 2.32E−03 | 2.45E−08 |
| IR-091 | 2.55E+05 | 1.88E−03 | 7.37E−09 |
| IR-099 | 2.71E+05 | 2.52E−03 | 9.30E−09 |
| IR-103 | 1.30E+05 | 5.71E−03 | 4.39E−08 |
| IR-130 | 1.65E+05 | 0.11 | 6.67E−07 |
| IR-148 | 2.41E+04 | 9.31E−04 | 3.86E−08 |
| 6E10 | 5.78E+04 | 1.68E−04 | 2.91E−09 |

Assay of the Neutralizaion Ability of the Anti-A Beta Oligomer Antibodies Against A Beta-Induced Cytotoxicity A beta oligomers cause cytotoxicity to neuronal cells. To assess whether the anti-A beta oligomer antibodies neutralize A beta-induced cytotoxicity, in vitro assay using human neuroblastoma cells (SH-SY5Y cells) was performed. Most of the antibodies showed the neutralization ability against A beta-induced cytotoxicity. Examples of the antibodies showing the neutralization ability are shown in FIG. 5. In the graphs, the value of Y axis indicates the relative rate to the cytotoxicity of A beta only (no antibody).

Assay of the Inhibition Ability of the Anti-A Beta Oligomer Antibodies Against A Beta-Fibril Formation A beta monomers form fibrils as a result of multimerization when they are incubated in a neutral pH buffer. To assess whether the antibodies inhibit the fibril formation, an antibody and A beta were mixed and incubated for 24 hours and the mixture were measured by fluorescence of Thioflavin T which reflects the amount of fibrils. Most of the antibodies showed the inhibition ability against A beta fibril formation. Examples of the antibodies showing the inhibition ability are shown in FIG. 6. In the graph, the value of Y axis indicates the relative rate to the fibril formation of A beta only (no antibody).

Immunoblotting to Confirm that the Anti-A Beta Oligomer Antibodies do not Bind to APP (Amyloid Precursor Protein)

Figure 7:
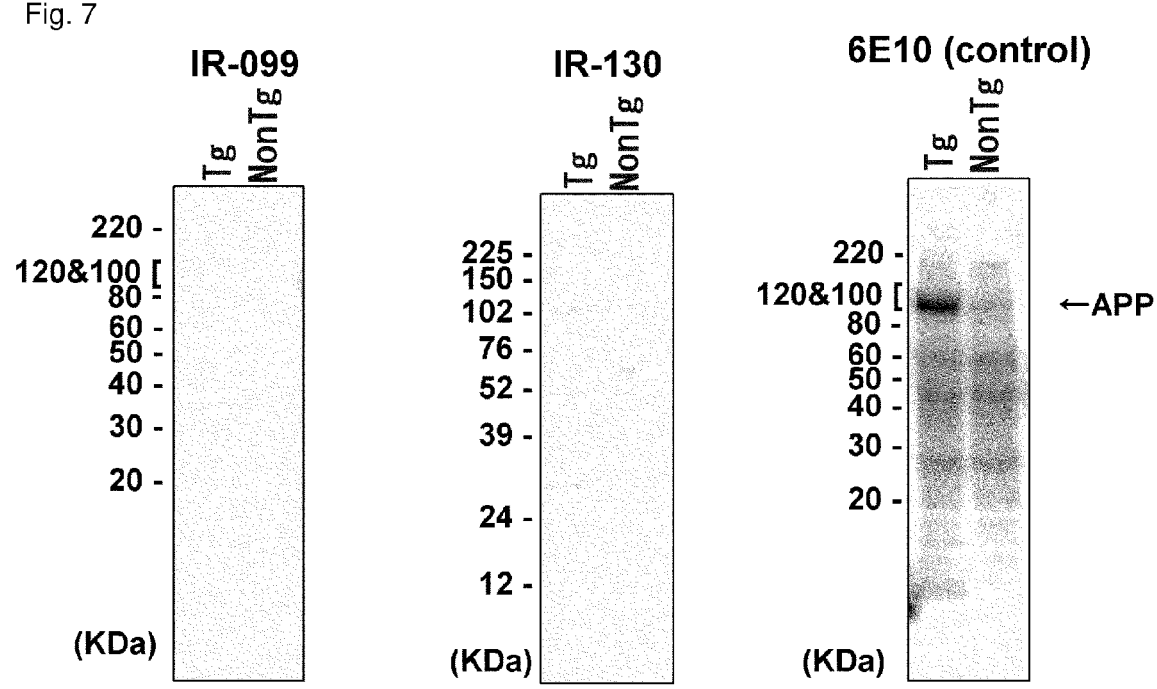
FIG. 7 shows the results of immunoblotting assay to assess whether each of the antibodies bind to human APP. Human APP was detected in the result of Tg2576 using control antibody 6E10, which is marked by the arrow.

It is important for escape of side effect that anti-A beta antibodies do not bind to APP which is the physiological protein expressed in a healthy body. Anti-A beta oligomer antibodies are expected not to bind to APP because they recognize the conformational domain of A beta oligomer that is not present in APP. Therefore, immunoblotting was performed to assess whether the anti-A beta oligomer antibodies of the present invention do not bind to APP. It was confirmed that they do not bind to human APP (compared with the result of control 6E10 antibody). Examples of immunoblotting analysis are shown in FIG. 7. This data also shows that the antibodies of the present invention have low binding affinity to proteins other than A beta oligomer, and the specificity of the antibodies is high (compared with the result of control 6E10 antibody).

INDUSTRIAL APPLICABILITY

The antibodies provided by the present invention are expected to contribute to the establishment of preventive/therapeutic methods selective to molecules responsible for evoking pathological conditions of Alzheimer's disease, and the establishment of early diagnostic markers for Alzheimer's disease.

The invention claimed is:

1. An isolated antibody that specifically binds an isolated A beta (Aβ) oligomer as an antigen, wherein the antibody does not bind to an Aβ monomer, and wherein the antibody comprises a heavy chain having CDR1, CDR2, and CDR3, which are identified in a heavy chain variable region comprising the amino acid sequence of SEQ ID NO: 106 and a light chain having CDR1, CDR2, and CDR3, which are identified in a light chain variable region comprising the amino acid sequence of SEQ ID NO: 108.

2. The antibody of claim 1, which further comprises:
   (1) heavy chain having the amino acid sequence of SEQ ID NO: 38 as CDR1, the amino acid sequence of SEQ ID NO: 40 as CDR2, and the amino acid sequence of SEQ ID NO: 42 as CDR3; or
   (2) light chain having the amino acid sequence of SEQ ID NO: 44 as CDR1, the amino acid sequence of SEQ ID NO: 46 as CDR2, and the amino acid sequence of SEQ ID NO: 48 as CDR3.

3. The antibody of claim 1, wherein the antibody is a chimeric antibody or a humanized antibody.

4. An antigen-binding fragment of the antibody of claim 1.

5. A pharmaceutical composition comprising the antibody of claim 1, and a pharmaceutically acceptable carrier.

6. The composition of claim 5, which is formulated for administration as a therapeutic agent for treating Alzheimer's disease, an agent for treating cognitive impairment associated with Aβ oligomers, an agent for suppressing senile plaque formation, an agent for suppressing Aβ accumulation, an agent for inhibiting Aβ amyloid fibril formation, or an agent for reducing Aβ-mediated synaptic toxicity.

7. A kit for detecting an Aβ oligomer contained in a sample or for diagnosing whether or not a subject is a possible Alzheimer's disease patient, the kit comprising the antibody of claim 1.

8. A method for detecting an Aβ oligomer, which comprises:
   (a) contacting a sample collected from a subject with the antibody of claim 1; and
   (b) detecting the presence of an Aβ oliqomer in the sample using an immunological detection method.

9. A method of diagnosing whether or not a subject is a possible Alzheimer's disease patient, which comprises:
   (a) contacting a sample collected from a subject with the antibody of claim 1; and (b) measuring the amount of Aβ oligomer in the sample,
wherein the subject is determined to be a possible Alzheimer's disease patient, when the amount measured in (b) is higher than that of a healthy individual.

10. A method of diagnosing whether or not a subject is a possible Alzheimer's disease patient, which comprises:
- (a) contacting a sample collected from a subject with the antibody of claim 1 and an antibody that binds to an Aβ monomer; and
- (b) measuring the ratio of Aβ oligomer to Aβ monomer in the sample, wherein the subject is determined to be a possible Alzheimer's disease patient, when the ratio measured in (b) is higher than that of a healthy individual.

11. The method of claim 8, wherein the sample is blood or cerebrospinal fluid.

12. The method of claim 9, wherein the sample is blood or cerebrospinal fluid.

13. The method of claim 10, wherein the sample is blood or cerebrospinal fluid.

* * * * *

SEQUENCE LISTING

<160> NUMBER OF SEQ ID NOS: 143

<210> SEQ ID NO 1
<211> LENGTH: 429
<212> TYPE: DNA
<213> ORGANISM: Mus musculus

<400> SEQUENCE: 1

| atgaacaggc ttacttcctc attgctgctg ctgattgtcc ctgcatatgt cctgtcccag | 60 |
| gttactctga aagagtctgg ccctgggata ttgcagccct cccagaccct cagtctgact | 120 |
| tgttctttct ctgggttttc actgagcact tctggtatgg gtgtgagctg gattcgtcag | 180 |
| ccttcaggaa agggtctgga gtggctggca cacatttact gggatgatga caagcgctat | 240 |
| aacccatccc tgaagagccg gctcacaatc tccaaggata cctccagcaa tcaggtattc | 300 |
| ctcaagatca ccagtgtgga cactgcagat actgccacat attactgtgc tcgaagaggg | 360 |
| gaggtgcgac gtcggggtta ctatgctatg gactactggg gtcaaggaac ctcagtcacc | 420 |
| gtctcctca | 429 |

<210> SEQ ID NO 2
<211> LENGTH: 143
<212> TYPE: PRT
<213> ORGANISM: Mus musculus

<400> SEQUENCE: 2

Met Asn Arg Leu Thr Ser Ser Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Gly Met Gly Val Ser Trp Ile Arg Gln Pro Ser Gly Lys
    50                  55                  60

Gly Leu Glu Trp Leu Ala His Ile Tyr Trp Asp Asp Asp Lys Arg Tyr
65                  70                  75                  80

Asn Pro Ser Leu Lys Ser Arg Leu Thr Ile Ser Lys Asp Thr Ser Ser
                85                  90                  95

Asn Gln Val Phe Leu Lys Ile Thr Ser Val Asp Thr Ala Asp Thr Ala
            100                 105                 110

Thr Tyr Tyr Cys Ala Arg Arg Gly Glu Val Arg Arg Gly Tyr Tyr
        115                 120                 125

Ala Met Asp Tyr Trp Gly Gln Gly Thr Ser Val Thr Val Ser Ser
    130                 135                 140

<210> SEQ ID NO 3
<211> LENGTH: 327
<212> TYPE: DNA
<213> ORGANISM: Mus musculus

<400> SEQUENCE: 3

| atgacccaaa ctccactctc cctgcctgtc agtcttggag atcaagcctc catctcttgc | 60 |
| agatctagtc agagccttgt acacagtaat ggaaacacct atttacattg gtacctgcag | 120 |
| aagccaggcc agtctccaaa gctcctgatc tacaaagttt ccaaccgatt ttctggggtc | 180 |
| ccagacaggt tcagtggcag tggatcaggg acagatttca cactcaagat cagcagagtg | 240 |
| gaggctgagg atctgggagt ttatttctgc tctcaaagta cacatgttcc gctcacgttc | 300 | ggtgctggga ccaagctgga gctgaaa                                                                    327

<210> SEQ ID NO 4
<211> LENGTH: 109
<212> TYPE: PRT
<213> ORGANISM: Mus musculus

<400> SEQUENCE: 4

```
Met Thr Gln Thr Pro Leu Ser Leu Pro Val Ser Leu Gly Asp Gln Ala
1               5                   10                  15

Ser Ile Ser Cys Arg Ser Ser Gln Ser Leu Val His Ser Asn Gly Asn
            20                  25                  30

Thr Tyr Leu His Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
    50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Phe Cys Ser Gln Ser Thr His Val
                85                  90                  95

Pro Leu Thr Phe Gly Ala Gly Thr Lys Leu Glu Leu Lys
            100                 105
```

<210> SEQ ID NO 5
<211> LENGTH: 21
<212> TYPE: DNA
<213> ORGANISM: Mus musculus

<400> SEQUENCE: 5
acttctggta tgggtgtgag c                                                                           21

<210> SEQ ID NO 6
<211> LENGTH: 7
<212> TYPE: PRT
<213> ORGANISM: Mus musculus

<400> SEQUENCE: 6

```
Thr Ser Gly Met Gly Val Ser
1               5
```

<210> SEQ ID NO 7
<211> LENGTH: 48
<212> TYPE: DNA
<213> ORGANISM: Mus musculus

<400> SEQUENCE: 7
cacatttact gggatgatga caagcgctat aacccatccc tgaagagc                                               48

<210> SEQ ID NO 8
<211> LENGTH: 16
<212> TYPE: PRT
<213> ORGANISM: Mus musculus

<400> SEQUENCE: 8

```
His Ile Tyr Trp Asp Asp Asp Lys Arg Tyr Asn Pro Ser Leu Lys Ser
1               5                   10                  15
```

<210> SEQ ID NO 9
<211> LENGTH: 42
<212> TYPE: DNA
<213> ORGANISM: Mus musculus

```
<400> SEQUENCE: 9
agaggggagg tgcgacgtcg gggttactat gctatggact ac                    42

<210> SEQ ID NO 10
<211> LENGTH: 14
<212> TYPE: PRT
<213> ORGANISM: Mus musculus

<400> SEQUENCE: 10

Arg Gly Glu Val Arg Arg Arg Gly Tyr Tyr Ala Met Asp Tyr
1               5                   10

<210> SEQ ID NO 11
<211> LENGTH: 48
<212> TYPE: DNA
<213> ORGANISM: Mus musculus

<400> SEQUENCE: 11
agatctagtc agagccttgt acacagtaat ggaaacacct atttacat              48

<210> SEQ ID NO 12
<211> LENGTH: 16
<212> TYPE: PRT
<213> ORGANISM: Mus musculus

<400> SEQUENCE: 12

Arg Ser Ser Gln Ser Leu Val His Ser Asn Gly Asn Thr Tyr Leu His
1               5                   10                  15

<210> SEQ ID NO 13
<211> LENGTH: 21
<212> TYPE: DNA
<213> ORGANISM: Mus musculus

<400> SEQUENCE: 13
aaagtttcca accgattttc t                                           21

<210> SEQ ID NO 14
<211> LENGTH: 7
<212> TYPE: PRT
<213> ORGANISM: Mus musculus

<400> SEQUENCE: 14

Lys Val Ser Asn Arg Phe Ser
1               5

<210> SEQ ID NO 15
<211> LENGTH: 27
<212> TYPE: DNA
<213> ORGANISM: Mus musculus

<400> SEQUENCE: 15
tctcaaagta cacatgttcc gctcacg                                     27

<210> SEQ ID NO 16
<211> LENGTH: 9
<212> TYPE: PRT
<213> ORGANISM: Mus musculus

<400> SEQUENCE: 16

Ser Gln Ser Thr His Val Pro Leu Thr
1               5

<210> SEQ ID NO 17
```

```
<211> LENGTH: 420
<212> TYPE: DNA
<213> ORGANISM: Mus musculus

<400> SEQUENCE: 17
atggacaggc ttacttcttc attcctgctg ctgattgtcc ctgcatatgt cttgtcccaa      60
gttactctaa aagagtctgg ccctgggata ttgaagccct cacagaccct cagtctgact     120
tgttcttcct ctgggttttc actgagcact tctggtatgg gtgtaggctg gattcgtcag     180
ccttcaggga agggtctgga gtggctggca cacatttggt gggatgatga aagtactat      240 aacccatccc tgaagagcca gctcacaatc tccaaggata cctccagaaa ccaggtattc     300
ctcaagatca ccagtgtgga cactgcagat actgccactt actactgtgc tcgaagagga     360
ttacgacgag ggactactt tgactactgg ggccaaggca ccactctcac agtctcctca      420

<210> SEQ ID NO 18
<211> LENGTH: 140
<212> TYPE: PRT
<213> ORGANISM: Mus musculus

<400> SEQUENCE: 18

Met Asp Arg Leu Thr Ser Ser Phe Leu Leu Ile Val Pro Ala Tyr
1               5                   10                  15

Val Leu Ser Gln Val Thr Leu Lys Glu Ser Gly Pro Gly Ile Leu Lys
            20                  25                  30

Pro Ser Gln Thr Leu Ser Leu Thr Cys Ser Phe Ser Gly Phe Ser Leu
        35                  40                  45

Ser Thr Ser Gly Met Gly Val Gly Trp Ile Arg Gln Pro Ser Gly Lys
    50                  55                  60

Gly Leu Glu Trp Leu Ala His Ile Trp Trp Asp Asp Lys Tyr Tyr
65                  70                  75                  80

Asn Pro Ser Leu Lys Ser Gln Leu Thr Ile Ser Lys Asp Thr Ser Arg
                85                  90                  95

Asn Gln Val Phe Leu Lys Ile Thr Ser Val Asp Thr Ala Asp Thr Ala
            100                 105                 110

Thr Tyr Tyr Cys Ala Arg Arg Gly Leu Arg Arg Gly Asp Tyr Phe Asp
        115                 120                 125

Tyr Trp Gly Gln Gly Thr Thr Leu Thr Val Ser Ser
    130                 135                 140

<210> SEQ ID NO 19
<211> LENGTH: 327
<212> TYPE: DNA
<213> ORGANISM: Mus musculus

<400> SEQUENCE: 19
atgacccaaa ctccactctc cctgcctgtc agtcttggag atcaagcctc catctcttgc      60
agatctagtc agagcattgt acatagtaat ggaaacacct atttagaatg gtacctgcaa     120
aaaccaggcc agtctccaaa gctcctgatc tacaaagttt ccaaccgatt ttctggggtc     180
ccagacaggt tcagtggcag tggatcaggg acagatttca cactcaagat cagcagagtg     240
gaggctgagg atctgggagt ttattactgc tttcaaggtt cacatgttcc gctcacgttc     300
ggtgctggga ccaagctgga gctgaaa                                         327

<210> SEQ ID NO 20
<211> LENGTH: 109
<212> TYPE: PRT
<213> ORGANISM: Mus musculus
```

```
<400> SEQUENCE: 20

Met Thr Gln Thr Pro Leu Ser Leu Pro Val Ser Leu Gly Asp Gln Ala
1               5                   10                  15

Ser Ile Ser Cys Arg Ser Ser Gln Ser Ile Val His Ser Asn Gly Asn
            20                  25                  30

Thr Tyr Leu Glu Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
    50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Tyr Cys Phe Gln Gly Ser His Val
                85                  90                  95

Pro Leu Thr Phe Gly Ala Gly Thr Lys Leu Glu Leu Lys
            100                 105

<210> SEQ ID NO 21
<211> LENGTH: 21
<212> TYPE: DNA
<213> ORGANISM: Mus musculus

<400> SEQUENCE: 21
acttctggta tgggtgtagg c                                           21

<210> SEQ ID NO 22
<211> LENGTH: 7
<212> TYPE: PRT
<213> ORGANISM: Mus musculus

<400> SEQUENCE: 22

Thr Ser Gly Met Gly Val Gly
1               5

<210> SEQ ID NO 23
<211> LENGTH: 48
<212> TYPE: DNA
<213> ORGANISM: Mus musculus

<400> SEQUENCE: 23
cacatttggt gggatgatga taagtactat aacccatccc tgaagagc              48

<210> SEQ ID NO 24
<211> LENGTH: 16
<212> TYPE: PRT
<213> ORGANISM: Mus musculus

<400> SEQUENCE: 24

His Ile Trp Trp Asp Asp Asp Lys Tyr Tyr Asn Pro Ser Leu Lys Ser
1               5                   10                  15

<210> SEQ ID NO 25
<211> LENGTH: 33
<212> TYPE: DNA
<213> ORGANISM: Mus musculus

<400> SEQUENCE: 25
agaggattac gacgagggga ctactttgac tac                              33

<210> SEQ ID NO 26
<211> LENGTH: 11
<212> TYPE: PRT
```

<213> ORGANISM: Mus musculus

<400> SEQUENCE: 26

Arg Gly Leu Arg Arg Gly Asp Tyr Phe Asp Tyr
1               5                   10

<210> SEQ ID NO 27
<211> LENGTH: 48
<212> TYPE: DNA
<213> ORGANISM: Mus musculus

<400> SEQUENCE: 27
agatctagtc agagcattgt acatagtaat ggaaacacct atttagaa           48

<210> SEQ ID NO 28
<211> LENGTH: 16
<212> TYPE: PRT
<213> ORGANISM: Mus musculus

<400> SEQUENCE: 28

Arg Ser Ser Gln Ser Ile Val His Ser Asn Gly Asn Thr Tyr Leu Glu
1               5                   10                  15

<210> SEQ ID NO 29
<211> LENGTH: 21
<212> TYPE: DNA
<213> ORGANISM: Mus musculus

<400> SEQUENCE: 29
aaagtttcca accgattttc t                                        21

<210> SEQ ID NO 30
<211> LENGTH: 7
<212> TYPE: PRT
<213> ORGANISM: Mus musculus

<400> SEQUENCE: 30

Lys Val Ser Asn Arg Phe Ser
1               5

<210> SEQ ID NO 31
<211> LENGTH: 27
<212> TYPE: DNA
<213> ORGANISM: Mus musculus

<400> SEQUENCE: 31
tttcaaggtt cacatgttcc gctcacg                                  27

<210> SEQ ID NO 32
<211> LENGTH: 9
<212> TYPE: PRT
<213> ORGANISM: Mus musculus

<400> SEQUENCE: 32

Phe Gln Gly Ser His Val Pro Leu Thr
1               5

<210> SEQ ID NO 33
<211> LENGTH: 417
<212> TYPE: DNA
<213> ORGANISM: Mus musculus

<400> SEQUENCE: 33
atggactcca ggctcaattt agttttcctt gtccttattt taaaggtgt ccagtgtgat    60

```
gtgcagctgg tggagtctgg gggaggctta gtgcagcctg agggtcccg gaaactctcc    120 tgtgcagcct ctggattcac tttcagtagg tttggaatgc actgggttcg tcaggctcca    180 gagaagggc tggagtgggt cgcatacatt agtagtggca aagtaccat ctactatgca    240 gacacagtga agggccgatt caccatctcc agagacaatc ccaagaacac cctgttcctg    300
caaatgacca gtctaaggtc tgaggacacg gccatgtatt actgtgcaag ggggggggt    360 aactacgttg ggctatgga ctactgggt caaggaacct cagtcaccgt ctcctca        417
```

<210> SEQ ID NO 34
<211> LENGTH: 139
<212> TYPE: PRT
<213> ORGANISM: Mus musculus

<400> SEQUENCE: 34

Met Asp Ser Arg Leu Asn Leu Val Phe Leu Val Leu Ile Leu Lys Gly
1               5                   10                  15

Val Gln Cys Asp Val Gln Leu Val Glu Ser Gly Gly Gly Leu Val Gln
            20                  25                  30

Pro Gly Gly Ser Arg Lys Leu Ser Cys Ala Ala Ser Gly Phe Thr Phe
        35                  40                  45

Ser Arg Phe Gly Met His Trp Val Arg Gln Ala Pro Glu Lys Gly Leu
    50                  55                  60

Glu Trp Val Ala Tyr Ile Ser Ser Gly Arg Ser Thr Ile Tyr Tyr Ala
65                  70                  75                  80

Asp Thr Val Lys Gly Arg Phe Thr Ile Ser Arg Asp Asn Pro Lys Asn
                85                  90                  95

Thr Leu Phe Leu Gln Met Thr Ser Leu Arg Ser Glu Asp Thr Ala Met
            100                 105                 110

Tyr Tyr Cys Ala Arg Gly Gly Gly Asn Tyr Val Gly Ala Met Asp Tyr
        115                 120                 125

Trp Gly Gln Gly Thr Ser Val Thr Val Ser Ser
    130                 135

<210> SEQ ID NO 35
<211> LENGTH: 327
<212> TYPE: DNA
<213> ORGANISM: Mus musculus

<400> SEQUENCE: 35

```
atgacccaaa ctccactctc cctgcctgtc agtcttggag atcaagcctc catctcttgc    60
aggtctagtc agagccttga aaacagtaat ggaaacacct atttgaactg gtacctccag    120
aaaccaggcc agtctccaca gctcctgatc tacagggttt ccaaccgatt ttctggggtc    180
ctagacaggt tcagtggtag tggatcaggg acagatttca cactgaaaat cagcagagtg    240
gaggctgagg atttgggagt ttatttctgc ctccaagtta cacatgtccc tccgacgttc    300
ggtggaggca ccaagctgga aatcaaa                                        327
```

<210> SEQ ID NO 36
<211> LENGTH: 109
<212> TYPE: PRT
<213> ORGANISM: Mus musculus

<400> SEQUENCE: 36

Met Thr Gln Thr Pro Leu Ser Leu Pro Val Ser Leu Gly Asp Gln Ala
1               5                   10                  15

Ser Ile Ser Cys Arg Ser Ser Gln Ser Leu Glu Asn Ser Asn Gly Asn
            20                  25                  30

```
Thr Tyr Leu Asn Trp Tyr Leu Gln Lys Pro Gly Gln Ser Pro Gln Leu
        35                  40                  45

Leu Ile Tyr Arg Val Ser Asn Arg Phe Ser Gly Val Leu Asp Arg Phe
 50                  55                  60

Ser Gly Ser Gly Ser Gly Thr Asp Phe Thr Leu Lys Ile Ser Arg Val
 65                  70                  75                  80

Glu Ala Glu Asp Leu Gly Val Tyr Phe Cys Leu Gln Val Thr His Val
                 85                  90                  95

Pro Pro Thr Phe Gly Gly Gly Thr Lys Leu Glu Ile Lys
            100                 105

<210> SEQ ID NO 37
<211> LENGTH: 15
<212> TYPE: DNA
<213> ORGANISM: Mus musculus

<400> SEQUENCE: 37
aggtttggaa tgcac                                                           15

<210> SEQ ID NO 38
<211> LENGTH: 5
<212> TYPE: PRT
<213> ORGANISM: Mus musculus

<400> SEQUENCE: 38

Arg Phe Gly Met His
 1               5

<210> SEQ ID NO 39
<211> LENGTH: 51
<212> TYPE: DNA
<213> ORGANISM: Mus musculus

<400> SEQUENCE: 39
tacattagta gtggcagaag taccatctac tatgcagaca cagtgaaggg c                   51

<210> SEQ ID NO 40
<211> LENGTH: 17
<212> TYPE: PRT
<213> ORGANISM: Mus musculus

<400> SEQUENCE: 40

Tyr Ile Ser Ser Gly Arg Ser Thr Ile Tyr Tyr Ala Asp Thr Val Lys
 1               5                  10                  15

Gly

<210> SEQ ID NO 41
<211> LENGTH: 33
<212> TYPE: DNA
<213> ORGANISM: Mus musculus

<400> SEQUENCE: 41 gggggggta actacgttgg ggctatggac tac                                        33

<210> SEQ ID NO 42
<211> LENGTH: 11
<212> TYPE: PRT
<213> ORGANISM: Mus musculus

<400> SEQUENCE: 42

Gly Gly Gly Asn Tyr Val Gly Ala Met Asp Tyr
 1               5                  10
```

<210> SEQ ID NO 43
<211> LENGTH: 48
<212> TYPE: DNA
<213> ORGANISM: Mus musculus

<400> SEQUENCE: 43
aggtctagtc agagccttga aaacagtaat ggaaacacct atttgaac       48

<210> SEQ ID NO 44
<211> LENGTH: 16
<212> TYPE: PRT
<213> ORGANISM: Mus musculus

<400> SEQUENCE: 44

Arg Ser Ser Gln Ser Leu Glu Asn Ser Asn Gly Asn Thr Tyr Leu Asn
1               5                   10                  15

<210> SEQ ID NO 45
<211> LENGTH: 21
<212> TYPE: DNA
<213> ORGANISM: Mus musculus

<400> SEQUENCE: 45
agggtttcca accgattttc t                                    21

<210> SEQ ID NO 46
<211> LENGTH: 7
<212> TYPE: PRT
<213> ORGANISM: Mus musculus

<400> SEQUENCE: 46

Arg Val Ser Asn Arg Phe Ser
1               5

<210> SEQ ID NO 47
<211> LENGTH: 27
<212> TYPE: DNA
<213> ORGANISM: Mus musculus

<400> SEQUENCE: 47
ctccaagtta cacatgtccc tccgacg                              27

<210> SEQ ID NO 48
<211> LENGTH: 9
<212> TYPE: PRT
<213> ORGANISM: Mus musculus

<400> SEQUENCE: 48

Leu Gln Val Thr His Val Pro Pro Thr
1               5

<210> SEQ ID NO 49
<211> LENGTH: 417
<212> TYPE: DNA
<213> ORGANISM: Mus musculus

<400> SEQUENCE: 49
atggactcca ggctcaattt agttttcctt gtccttattt taaaaggtgt ccagtgtgat    60
gtgcagctgg tggagtctgg gggaggctta gtgcagcctg agggtcccg gaaactctcc   120 tgtgcagcct ctggattcac tttcagtagc tttggaatgc actgggttcg tcaggctcca   180
gagaaggggc tggagtgggt cgcatacatt agtagtggca gtagtaccat ctactatgca   240

```
gacacagtga agggccgatt caccatctcc agagacaatc ccaagaacac cctgttcctg    300
caaatgacca gtctaaggtc tgaggacacg gccatgtatt actgtgcaag atccccatta    360
ctacggctac agggacttgc ttactggggc aagggactc tggtcactgt ctctgca       417
```

<210> SEQ ID NO 50
<211> LENGTH: 139
<212> TYPE: PRT
<213> ORGANISM: Mus musculus

<400> SEQUENCE: 50

```
Met Asp Ser Arg Leu Asn Leu Val Phe Leu Val Leu Ile Leu Lys Gly
1               5                   10                  15
Val Gln Cys Asp Val Gln Leu Val Glu Ser Gly Gly Gly Leu Val Gln
                20                  25                  30
Pro Gly Gly Ser Arg Lys Leu Ser Cys Ala Ala Ser Gly Phe Thr Phe
            35                  40                  45
Ser Ser Phe Gly Met His Trp Val Arg Gln Ala Pro Glu Lys Gly Leu
        50                  55                  60
Glu Trp Val Ala Tyr Ile Ser Gly Ser Ser Thr Ile Tyr Tyr Ala
65                  70                  75                  80
Asp Thr Val Lys Gly Arg Phe Thr Ile Ser Arg Asp Asn Pro Lys Asn
                85                  90                  95
Thr Leu Phe Leu Gln Met Thr Ser Leu Arg Ser Glu Asp Thr Ala Met
            100                 105                 110
Tyr Tyr Cys Ala Arg Ser Pro Leu Leu Arg Leu Gln Gly Leu Ala Tyr
        115                 120                 125
Trp Gly Gln Gly Thr Leu Val Thr Val Ser Ala
    130                 135
```

<210> SEQ ID NO 51
<211> LENGTH: 327
<212> TYPE: DNA
<213> ORGANISM: Mus musculus

<400> SEQUENCE: 51

```
atgacccaaa ctccactctc cctgcctgtc agtcttggag atcaagcctc catctcttgc    60
agatctagtc agagcattgt acatagtaat ggaaacacct atttagaatg gtacctgcag    120
aaaccaggcc agtctccaaa gctcctgatc tacaaagttt ccaaccgatt ttctggggtc    180
ccagacaggt tcagtggcag tggatcaggg acagatttca cactcaagat cagcagagtg    240
gaggctgagg atctgggagt ttattactgc tttcaaggtt cacatgttcc tcgacgttc     300 ggtggaggca ccaagctgga aatcaaa                                        327
```

<210> SEQ ID NO 52
<211> LENGTH: 109
<212> TYPE: PRT
<213> ORGANISM: Mus musculus

<400> SEQUENCE: 52

```
Met Thr Gln Thr Pro Leu Ser Leu Pro Val Ser Leu Gly Asp Gln Ala
1               5                   10                  15
Ser Ile Ser Cys Arg Ser Ser Gln Ser Ile Val His Ser Asn Gly Asn
                20                  25                  30
Thr Tyr Leu Glu Trp Tyr Leu Gln Lys Pro Gly Gln Ser Pro Lys Leu
            35                  40                  45
Leu Ile Tyr Lys Val Ser Asn Arg Phe Ser Gly Val Pro Asp Arg Phe
        50                  55                  60
```

```
Ser Gly Ser Gly Ser Gly Thr Asp Phe Thr Leu Lys Ile Ser Arg Val
65                  70                  75                  80

Glu Ala Glu Asp Leu Gly Val Tyr Tyr Cys Phe Gln Gly Ser His Val
                85                  90                  95

Pro Pro Thr Phe Gly Gly Gly Thr Lys Leu Glu Ile Lys
            100                 105
```

<210> SEQ ID NO 53
<211> LENGTH: 15
<212> TYPE: DNA
<213> ORGANISM: Mus musculus

<400> SEQUENCE: 53
agctttggaa tgcac                                                        15

<210> SEQ ID NO 54
<211> LENGTH: 5
<212> TYPE: PRT
<213> ORGANISM: Mus musculus

<400> SEQUENCE: 54

```
Ser Phe Gly Met His
1               5
```

<210> SEQ ID NO 55
<211> LENGTH: 51
<212> TYPE: DNA
<213> ORGANISM: Mus musculus

<400> SEQUENCE: 55
tacattagta gtggcagtag taccatctac tatgcagaca cagtgaaggg c                51

<210> SEQ ID NO 56
<211> LENGTH: 17
<212> TYPE: PRT
<213> ORGANISM: Mus musculus

<400> SEQUENCE: 56

```
Tyr Ile Ser Ser Gly Ser Ser Thr Ile Tyr Tyr Ala Asp Thr Val Lys
1               5                   10                  15

Gly
```

<210> SEQ ID NO 57
<211> LENGTH: 33
<212> TYPE: DNA
<213> ORGANISM: Mus musculus

<400> SEQUENCE: 57
tccccattac tacggctaca gggacttgct tac                                    33

<210> SEQ ID NO 58
<211> LENGTH: 11
<212> TYPE: PRT
<213> ORGANISM: Mus musculus

<400> SEQUENCE: 58

```
Ser Pro Leu Leu Arg Leu Gln Gly Leu Ala Tyr
1               5                   10
```

<210> SEQ ID NO 59
<211> LENGTH: 48
<212> TYPE: DNA
<213> ORGANISM: Mus musculus

<400> SEQUENCE: 59
agatctagtc agagcattgt acatagtaat ggaaacacct atttagaa                48

<210> SEQ ID NO 60
<211> LENGTH: 16
<212> TYPE: PRT
<213> ORGANISM: Mus musculus

<400> SEQUENCE: 60

Arg Ser Ser Gln Ser Ile Val His Ser Asn Gly Asn Thr Tyr Leu Glu
1               5                   10                  15

<210> SEQ ID NO 61
<211> LENGTH: 21
<212> TYPE: DNA
<213> ORGANISM: Mus musculus

<400> SEQUENCE: 61
aaagtttcca accgattttc t                                              21

<210> SEQ ID NO 62
<211> LENGTH: 7
<212> TYPE: PRT
<213> ORGANISM: Mus musculus

<400> SEQUENCE: 62

Lys Val Ser Asn Arg Phe Ser
1               5

<210> SEQ ID NO 63
<211> LENGTH: 27
<212> TYPE: DNA
<213> ORGANISM: Mus musculus

<400> SEQUENCE: 63
tttcaaggtt cacatgttcc tccgacg                                        27

<210> SEQ ID NO 64
<211> LENGTH: 9
<212> TYPE: PRT
<213> ORGANISM: Mus musculus

<400> SEQUENCE: 64

Phe Gln Gly Ser His Val Pro Pro Thr
1               5

<210> SEQ ID NO 65
<211> LENGTH: 429
<212> TYPE: DNA
<213> ORGANISM: Mus musculus

<400> SEQUENCE: 65
atgaacttgg ggctcagctt gattttcctt gtccttgttt taaaaggtgt ccagtgtgaa    60
gtgaagctgg tggagtctgg gggaggctta gtgcagcctg agggtccct gaaactctcc    120 tgtgcaacct ctggattcac tttcagtgac tattacatgt attgggttcg ccagactcca   180
gagaagaggc tggagtgggt cgcatacatt agtaatggtg gtggtagcac ctattatcca   240
gacactgtaa agggccgatt caccatctcc agagacaatg ccaagaacac cctgtacctg   300
caaatgagcc gtctgaagtc tgaggacaca gccatgtatt actgtgcaag agggacctca   360
tacggtagta gccttcatta ctatgctatg gactactggg gtcaaggaac ctcagtcacc   420
gtctcctca                                                                   429

<210> SEQ ID NO 66
<211> LENGTH: 143
<212> TYPE: PRT
<213> ORGANISM: Mus musculus

<400> SEQUENCE: 66

Met Asn Leu Gly Leu Ser Leu Ile Phe Leu Val Leu Val Leu Lys Gly
1               5                   10                  15

Val Gln Cys Glu Val Lys Leu Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

Ser Asp Tyr Tyr Met Tyr Trp Val Arg Gln Thr Pro Glu Lys Arg Leu
    50                  55                  60

Glu Trp Val Ala Tyr Ile Ser Asn Gly Gly Gly Ser Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Arg Leu Lys Ser Glu Asp Thr Ala Met
            100                 105                 110

Tyr Tyr Cys Ala Arg Gly Thr Ser Tyr Gly Ser Ser Leu His Tyr Tyr
        115                 120                 125

Ala Met Asp Tyr Trp Gly Gln Gly Thr Ser Val Thr Val Ser Ser
    130                 135                 140

<210> SEQ ID NO 67
<211> LENGTH: 327
<212> TYPE: DNA
<213> ORGANISM: Mus musculus

<400> SEQUENCE: 67
atgacccaaa ctccactctc cctgcctgtc agtcttggag atcaagcctc catctcttgc      60
agatctagtc agagccttgt acacagtaat ggaaacacct atttacattg gtacctgcag     120
aagccaggcc agtctccaaa gctcctgatc tacaaagttt ccaaccgatt ttctggggtc     180
ccagacaggt tcagtggcag tggatcaggg acagatttca cactcaagat cagcagagtg     240
gaggctgagg atctgggagt ttatttctgc tctcaaagta cacatgttcc gctcacgttc     300
ggtgctggga ccaagctgga gctgaaa                                         327

<210> SEQ ID NO 68
<211> LENGTH: 109
<212> TYPE: PRT
<213> ORGANISM: Mus musculus

<400> SEQUENCE: 68

Met Thr Gln Thr Pro Leu Ser Leu Pro Val Ser Leu Gly Asp Gln Ala
1               5                   10                  15

Ser Ile Ser Cys Arg Ser Ser Gln Ser Leu Val His Ser Asn Gly Asn
            20                  25                  30

Thr Tyr Leu His Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
    50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Phe Cys Ser Gln Ser Thr His Val
                85                  90                  95

Pro Leu Thr Phe Gly Ala Gly Thr Lys Leu Glu Leu Lys
            100                 105

<210> SEQ ID NO 69
<211> LENGTH: 15
<212> TYPE: DNA
<213> ORGANISM: Mus musculus

<400> SEQUENCE: 69
gactattaca tgtat                                                    15

<210> SEQ ID NO 70
<211> LENGTH: 5
<212> TYPE: PRT
<213> ORGANISM: Mus musculus

<400> SEQUENCE: 70

Asp Tyr Tyr Met Tyr
1               5

<210> SEQ ID NO 71
<211> LENGTH: 51
<212> TYPE: DNA
<213> ORGANISM: Mus musculus

<400> SEQUENCE: 71
tacattagta atggtggtgg tagcacctat tatccagaca ctgtaaaggg c             51

<210> SEQ ID NO 72
<211> LENGTH: 17
<212> TYPE: PRT
<213> ORGANISM: Mus musculus

<400> SEQUENCE: 72

Tyr Ile Ser Asn Gly Gly Gly Ser Thr Tyr Tyr Pro Asp Thr Val Lys
1               5                   10                  15

Gly

<210> SEQ ID NO 73
<211> LENGTH: 45
<212> TYPE: DNA
<213> ORGANISM: Mus musculus

<400> SEQUENCE: 73
gggacctcat acggtagtag ccttcattac tatgctatgg actac                   45

<210> SEQ ID NO 74
<211> LENGTH: 15
<212> TYPE: PRT
<213> ORGANISM: Mus musculus

<400> SEQUENCE: 74

Gly Thr Ser Tyr Gly Ser Ser Leu His Tyr Tyr Ala Met Asp Tyr
1               5                   10                  15

<210> SEQ ID NO 75
<211> LENGTH: 48
<212> TYPE: DNA
<213> ORGANISM: Mus musculus

<400> SEQUENCE: 75
agatctagtc agagccttgt acacagtaat ggaaacacct atttacat                48

<210> SEQ ID NO 76
<211> LENGTH: 16
<212> TYPE: PRT
<213> ORGANISM: Mus musculus

<400> SEQUENCE: 76

Arg Ser Ser Gln Ser Leu Val His Ser Asn Gly Asn Thr Tyr Leu His
1               5                   10                  15

<210> SEQ ID NO 77
<211> LENGTH: 21
<212> TYPE: DNA
<213> ORGANISM: Mus musculus

<400> SEQUENCE: 77
aaagtttcca accgattttc t                                            21

<210> SEQ ID NO 78
<211> LENGTH: 7
<212> TYPE: PRT
<213> ORGANISM: Mus musculus

<400> SEQUENCE: 78

Lys Val Ser Asn Arg Phe Ser
1               5

<210> SEQ ID NO 79
<211> LENGTH: 27
<212> TYPE: DNA
<213> ORGANISM: Mus musculus

<400> SEQUENCE: 79
tctcaaagta cacatgttcc gctcacg                                      27

<210> SEQ ID NO 80
<211> LENGTH: 9
<212> TYPE: PRT
<213> ORGANISM: Mus musculus

<400> SEQUENCE: 80

Ser Gln Ser Thr His Val Pro Leu Thr
1               5

<210> SEQ ID NO 81
<211> LENGTH: 405
<212> TYPE: DNA
<213> ORGANISM: Mus musculus

<400> SEQUENCE: 81
atggactcca ggctcaattt agttttcctt gtccttattt taaaaggtgt ccagtgtgat      60
gtgcagctgg tggagtctgg gggaggctta gtgcagcctg agggtcccg gaaactctcc     120
tgtgcagcct ctggattcac tttcagtagc tttggaatgc actgggttcg tcaggctcca     180
gagaaggggc tggagtgggt cgcatacatt agtagtggca gtagtaccat ctactatgca     240
gacacagtga agggccgatt caccatctcc agagacaatc caagaacac cctgttcctg      300
caaatgacca gtctaaggtc tgaggacacg gccatgtatt actgtgcaag agattactac     360
ggtatggact actggggtca aggaacctca gtcaccgtct cctca                    405

<210> SEQ ID NO 82
<211> LENGTH: 135
<212> TYPE: PRT

<213> ORGANISM: Mus musculus

<400> SEQUENCE: 82

Met Asp Ser Arg Leu Asn Leu Val Phe Leu Val Ile Leu Lys Gly
1               5                   10                  15
Val Gln Cys Asp Val Gln Leu Val Glu Ser Gly Gly Gly Leu Val Gln
            20                  25                  30
Pro Gly Gly Ser Arg Lys Leu Ser Cys Ala Ala Ser Gly Phe Thr Phe
        35                  40                  45
Ser Ser Phe Gly Met His Trp Val Arg Gln Ala Pro Glu Lys Gly Leu
50                  55                  60
Glu Trp Val Ala Tyr Ile Ser Ser Gly Ser Ser Thr Ile Tyr Tyr Ala
65                  70                  75                  80
Asp Thr Val Lys Gly Arg Phe Thr Ile Ser Arg Asp Asn Pro Lys Asn
                85                  90                  95
Thr Leu Phe Leu Gln Met Thr Ser Leu Arg Ser Glu Asp Thr Ala Met
            100                 105                 110
Tyr Tyr Cys Ala Arg Asp Tyr Tyr Gly Met Asp Tyr Trp Gly Gln Gly
        115                 120                 125
Thr Ser Val Thr Val Ser Ser
    130                 135

<210> SEQ ID NO 83
<211> LENGTH: 327
<212> TYPE: DNA
<213> ORGANISM: Mus musculus

<400> SEQUENCE: 83
atgacccaaa ctccactctc cctgcctgtc agtcttggag atcaagcctc catctcttgc      60
agatctagtc agagccttgt acacagtaat ggaaacacct atttacattg gtacctgcag     120
aagccaggcc agtctccaaa gctcctgatc tacaaagttt ccaaccgatt ttctggggtc     180
ccagacaggt tcagtggcag tggatcaggg acagatttca cactcaagat cagcagagtg     240
gaggctgagg atctgggagt ttatttctgc tctcaaagta cacatgttcc gctcacgttc     300
ggtgctggga ccaagctgga gctgaaa                                         327

<210> SEQ ID NO 84
<211> LENGTH: 109
<212> TYPE: PRT
<213> ORGANISM: Mus musculus

<400> SEQUENCE: 84

Met Thr Gln Thr Pro Leu Ser Leu Pro Val Ser Leu Gly Asp Gln Ala
1               5                   10                  15
Ser Ile Ser Cys Arg Ser Ser Gln Ser Leu Val His Ser Asn Gly Asn
            20                  25                  30
Thr Tyr Leu His Trp Tyr Leu Gln Lys Pro Gly Gln Ser Pro Lys Leu
        35                  40                  45
Leu Ile Tyr Lys Val Ser Asn Arg Phe Ser Gly Val Pro Asp Arg Phe
50                  55                  60
Ser Gly Ser Gly Ser Gly Thr Asp Phe Thr Leu Lys Ile Ser Arg Val
65                  70                  75                  80
Glu Ala Glu Asp Leu Gly Val Tyr Phe Cys Ser Gln Ser Thr His Val
                85                  90                  95
Pro Leu Thr Phe Gly Ala Gly Thr Lys Leu Glu Leu Lys
            100                 105

```
<210> SEQ ID NO 85
<211> LENGTH: 15
<212> TYPE: DNA
<213> ORGANISM: Mus musculus

<400> SEQUENCE: 85
agctttggaa tgcac                                                    15

<210> SEQ ID NO 86
<211> LENGTH: 5
<212> TYPE: PRT
<213> ORGANISM: Mus musculus

<400> SEQUENCE: 86

Ser Phe Gly Met His
1               5

<210> SEQ ID NO 87
<211> LENGTH: 51
<212> TYPE: DNA
<213> ORGANISM: Mus musculus

<400> SEQUENCE: 87
tacattagta gtggcagtag taccatctac tatgcagaca cagtgaaggg c             51

<210> SEQ ID NO 88
<211> LENGTH: 17
<212> TYPE: PRT
<213> ORGANISM: Mus musculus

<400> SEQUENCE: 88

Tyr Ile Ser Ser Gly Ser Ser Thr Ile Tyr Tyr Ala Asp Thr Val Lys
1               5                   10                  15
Gly

<210> SEQ ID NO 89
<211> LENGTH: 21
<212> TYPE: DNA
<213> ORGANISM: Mus musculus

<400> SEQUENCE: 89
gattactacg gtatggacta c                                             21

<210> SEQ ID NO 90
<211> LENGTH: 7
<212> TYPE: PRT
<213> ORGANISM: Mus musculus

<400> SEQUENCE: 90

Asp Tyr Tyr Gly Met Asp Tyr
1               5

<210> SEQ ID NO 91
<211> LENGTH: 48
<212> TYPE: DNA
<213> ORGANISM: Mus musculus

<400> SEQUENCE: 91
agatctagtc agagccttgt acacagtaat ggaaacacct atttacat                48

<210> SEQ ID NO 92
<211> LENGTH: 16
<212> TYPE: PRT
<213> ORGANISM: Mus musculus
```

<400> SEQUENCE: 92

Arg Ser Ser Gln Ser Leu Val His Ser Asn Gly Asn Thr Tyr Leu His
1               5                   10                  15

<210> SEQ ID NO 93
<211> LENGTH: 21
<212> TYPE: DNA
<213> ORGANISM: Mus musculus

<400> SEQUENCE: 93
aaagtttcca accgattttc t                                          21

<210> SEQ ID NO 94
<211> LENGTH: 7
<212> TYPE: PRT
<213> ORGANISM: Mus musculus

<400> SEQUENCE: 94

Lys Val Ser Asn Arg Phe Ser
1               5

<210> SEQ ID NO 95
<211> LENGTH: 27
<212> TYPE: DNA
<213> ORGANISM: Mus musculus

<400> SEQUENCE: 95
tctcaaagta cacatgttcc gctcacg                                    27

<210> SEQ ID NO 96
<211> LENGTH: 9
<212> TYPE: PRT
<213> ORGANISM: Mus musculus

<400> SEQUENCE: 96

Ser Gln Ser Thr His Val Pro Leu Thr
1               5

<210> SEQ ID NO 97
<211> LENGTH: 372
<212> TYPE: DNA
<213> ORGANISM: Mus musculus

<400> SEQUENCE: 97
caggttactc tgaaagagtc tggccctggg atattgcagc cctcccagac cctcagtctg    60
acttgttctt tctctgggtt ttcactgagc acttctggta tgggtgtgag ctggattcgt   120
cagccttcag gaaagggtct ggagtggctg gcacacattt actgggatga tgacaagcgc   180
tataacccat ccctgaagag ccggctcaca atctccaagg atacctccag caatcaggta   240
ttcctcaaga tcaccagtgt ggacactgca gatactgcca catattactg tgctcgaaga   300
ggggaggtgc gacgtcgggg ttactatgct atggactact ggggtcaagg aacctcagtc   360
accgtctcct ca                                                      372

<210> SEQ ID NO 98
<211> LENGTH: 124
<212> TYPE: PRT
<213> ORGANISM: Mus musculus

<400> SEQUENCE: 98

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
            35                  40                  45

Trp Leu Ala His Ile Tyr Trp Asp Asp Lys Arg Tyr Asn Pro Ser
50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Thr Ala Thr Tyr Tyr
            85                  90                  95

Cys Ala Arg Arg Gly Glu Val Arg Arg Gly Tyr Tyr Ala Met Asp
            100                 105                 110

Tyr Trp Gly Gln Gly Thr Ser Val Thr Val Ser Ser
            115                 120

<210> SEQ ID NO 99
<211> LENGTH: 336
<212> TYPE: DNA
<213> ORGANISM: Mus musculus

<400> SEQUENCE: 99
gatgttgtga tgacccaaac tccactctcc ctgcctgtca gtcttggaga tcaagcctcc      60
atctcttgca gatctagtca gagccttgta cacagtaatg gaaacaccta tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttccg     300
ctcacgttcg gtgctgggac caagctggag ctgaaa                               336

<210> SEQ ID NO 100
<211> LENGTH: 112
<212> TYPE: PRT
<213> ORGANISM: Mus musculus

<400> SEQUENCE: 100

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
            85                  90                  95

Thr His Val Pro Leu Thr Phe Gly Ala Gly Thr Lys Leu Glu Leu Lys
            100                 105                 110

<210> SEQ ID NO 101
<211> LENGTH: 363
<212> TYPE: DNA
<213> ORGANISM: Mus musculus

<400> SEQUENCE: 101
caagttactc taaaagagtc tggccctggg atattgaagc cctcacagac cctcagtctg      60

```
acttgttctt tctctgggtt ttcactgagc acttctggta tgggtgtagg ctggattcgt      120
cagccttcag ggaagggtct ggagtggctg gcacacattt ggtgggatga tgataagtac      180
tataacccat ccctgaagag ccagctcaca atctccaagg atacctccag aaaccaggta      240
ttcctcaaga tcaccagtgt ggacactgca gatactgcca cttactactg tgctcgaaga      300
ggattacgac gaggggacta ctttgactac tggggccaag gcaccactct cacagtctcc      360
tca                                                                    363
```

<210> SEQ ID NO 102
<211> LENGTH: 121
<212> TYPE: PRT
<213> ORGANISM: Mus musculus

<400> SEQUENCE: 102

```
Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Gly Leu Arg Arg Gly Asp Tyr Phe Asp Tyr Trp Gly
            100                 105                 110

Gln Gly Thr Thr Leu Thr Val Ser Ser
        115                 120
```

<210> SEQ ID NO 103
<211> LENGTH: 336
<212> TYPE: DNA
<213> ORGANISM: Mus musculus

<400> SEQUENCE: 103

```
gatgttttga tgacccaaac tccactctcc ctgcctgtca gtcttggaga tcaagcctcc      60
atctcttgca gatctagtca gagcattgta catagtaatg aaacacccta tttagaatgg      120
tacctgcaaa aaccaggcca gtctccaaag ctcctgatct acaaagtttc caaccgattt      180
tctggggtcc cagacaggtt cagtggcagt ggatcaggga cagatttcac actcaagatc      240
agcagagtgg aggctgagga tctgggagtt tattactgct tcaaggttc acatgttccg      300 ctcacgttcg gtgctgggac caagctggag ctgaaa                                336
```

<210> SEQ ID NO 104
<211> LENGTH: 112
<212> TYPE: PRT
<213> ORGANISM: Mus musculus

<400> SEQUENCE: 104

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
```

```
                   35                  40                  45
Pro Lys Leu Leu Ile Tyr Lys Val Ser Asn Arg Phe Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Leu Gly Val Tyr Tyr Cys Phe Gln Gly
                     85                  90                  95
Ser His Val Pro Leu Thr Phe Gly Ala Gly Thr Lys Leu Glu Leu Lys
            100                 105                 110

<210> SEQ ID NO 105
<211> LENGTH: 360
<212> TYPE: DNA
<213> ORGANISM: Mus musculus

<400> SEQUENCE: 105
gatgtgcagc tggtggagtc tgggggaggc ttagtgcagc ctggagggtc ccggaaactc      60
tcctgtgcag cctctggatt cactttcagt aggtttggaa tgcactgggt tcgtcaggct     120
ccagagaagg ggctggagtg ggtcgcatac attagtagtg cagaagtac catctactat      180 gcagacacag tgaagggccg attcaccatc tccagagaca atcccaagaa caccctgttc     240
ctgcaaatga ccagtctaag gtctgaggac acggccatgt attactgtgc aagagggggg     300
ggtaactacg ttggggctat ggactactgg ggtcaaggaa cctcagtcac cgtctcctca     360

<210> SEQ ID NO 106
<211> LENGTH: 120
<212> TYPE: PRT
<213> ORGANISM: Mus musculus

<400> SEQUENCE: 106

Asp Val Gln Leu Val Glu Ser Gly Gly Gly Leu Val Gln Pro Gly Gly
  1               5                  10                  15

Ser Arg Lys Leu Ser Cys Ala Ala Ser Gly Phe Thr Phe Ser Arg Phe
                 20                  25                  30

Gly Met His Trp Val Arg Gln Ala Pro Glu Lys Gly Leu Glu Trp Val
             35                  40                  45

Ala Tyr Ile Ser Ser Gly Arg Ser Thr Ile Tyr Tyr Ala Asp Thr Val
 50                  55                  60

Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                     85                  90                  95

Ala Arg Gly Gly Gly Asn Tyr Val Gly Ala Met Asp Tyr Trp Gly Gln
            100                 105                 110

Gly Thr Ser Val Thr Val Ser Ser
        115                 120

<210> SEQ ID NO 107
<211> LENGTH: 336
<212> TYPE: DNA
<213> ORGANISM: Mus musculus

<400> SEQUENCE: 107
gatgctgtga tgacccaaac tccactctcc ctgcctgtca gtcttggaga tcaagcctcc      60
atctcttgca ggtctagtca gagccttgaa aacagtaatg gaaacaccta tttgaactgg     120
tacctccaga aaccaggcca gtctccacag ctcctgatct acaggtttc caaccgattt      180
```

```
tctgggtcc tagacaggtt cagtggtagt ggatcaggga cagatttcac actgaaaatc      240
agcagagtgg aggctgagga tttgggagtt tatttctgcc tccaagttac acatgtccct      300
ccgacgttcg gtggaggcac aagctggaa atcaaa                                336
```

<210> SEQ ID NO 108
<211> LENGTH: 112
<212> TYPE: PRT
<213> ORGANISM: Mus musculus

<400> SEQUENCE: 108

```
Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Pro Thr Phe Gly Gly Gly Thr Lys Leu Glu Ile Lys
            100                 105                 110
```

<210> SEQ ID NO 109
<211> LENGTH: 360
<212> TYPE: DNA
<213> ORGANISM: Mus musculus

<400> SEQUENCE: 109

```
gatgtgcagc tggtggagtc tgggggaggc ttagtgcagc ctggagggtc ccggaaactc       60
tcctgtgcag cctctggatt cactttcagt agctttggaa tgcactgggt tcgtcaggct      120
ccagagaagg ggctggagtg gtcgcatac attagtagtg gcagtagtac catctactat      180
gcagacacag tgaagggccg attcaccatc tccagagaca atcccaagaa caccctgttc      240
ctgcaaatga ccagtctaag gtctgaggac acggccatgt attactgtgc aagatcccca      300
ttactacggc tacagggact tgcttactgg ggccaaggga ctctggtcac tgtctctgca      360
```

<210> SEQ ID NO 110
<211> LENGTH: 120
<212> TYPE: PRT
<213> ORGANISM: Mus musculus

<400> SEQUENCE: 110

```
Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95
```

Ala Arg Ser Pro Leu Leu Arg Leu Gln Gly Leu Ala Tyr Trp Gly Gln
                100                 105                 110

Gly Thr Leu Val Thr Val Ser Ala
        115                 120

<210> SEQ ID NO 111
<211> LENGTH: 336
<212> TYPE: DNA
<213> ORGANISM: Mus musculus

<400> SEQUENCE: 111
gatgttttga tgacccaaac tccactctcc ctgcctgtca gtcttggaga tcaagcctcc      60
atctcttgca gatctagtca gagcattgta catagtaatg aaacaccta tttagaatgg     120 tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttcct     300
ccgacgttcg gtggaggcac caagctggaa atcaaa                              336

<210> SEQ ID NO 112
<211> LENGTH: 112
<212> TYPE: PRT
<213> ORGANISM: Mus musculus

<400> SEQUENCE: 112

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 113
<211> LENGTH: 372
<212> TYPE: DNA
<213> ORGANISM: Mus musculus

<400> SEQUENCE: 113
gaagtgaagc tggtggagtc tgggggaggc ttagtgcagc ctggagggtc cctgaaactc      60
tcctgtgcaa cctctggatt cactttcagt gactattaca tgtattgggt tcgccagact     120
ccagagaaga ggctggagtg gtcgcatac attagtaatg gtggtggtag cacctattat     180
ccagacactg taaagggccg attcaccatc tccagagaca atgccaagaa caccctgtac     240
ctgcaaatga gccgtctgaa gtctgaggac acagccatgt attactgtgc aagagggacc     300
tcatacggta gtagccttca ttactatgct atggactact ggggtcaagg aacctcagtc     360
accgtctcct ca                                                        372

<210> SEQ ID NO 114

```
<211> LENGTH: 124
<212> TYPE: PRT
<213> ORGANISM: Mus musculus

<400> SEQUENCE: 114

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Gly Thr Ser Tyr Gly Ser Ser Leu His Tyr Tyr Ala Met Asp
            100                 105                 110

Tyr Trp Gly Gln Gly Thr Ser Val Thr Val Ser Ser
        115                 120

<210> SEQ ID NO 115
<211> LENGTH: 336
<212> TYPE: DNA
<213> ORGANISM: Mus musculus

<400> SEQUENCE: 115
gatgttgtga tgacccaaac tccactctcc ctgcctgtca gtcttggaga tcaagcctcc      60
atctcttgca gatctagtca gagccttgta cacagtaatg gaaacaccta tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttccg     300
ctcacgttcg gtgctgggac caagctggag ctgaaa                                336

<210> SEQ ID NO 116
<211> LENGTH: 112
<212> TYPE: PRT
<213> ORGANISM: Mus musculus

<400> SEQUENCE: 116

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110
```

<210> SEQ ID NO 117
<211> LENGTH: 348
<212> TYPE: DNA
<213> ORGANISM: Mus musculus

<400> SEQUENCE: 117

| | | |
|---|---|---|
| gatgtgcagc tggtggagtc tgggggaggc ttagtgcagc ctggagggtc ccggaaactc | 60 |
| tcctgtgcag cctctggatt cactttcagt agctttggaa tgcactgggt tcgtcaggct | 120 |
| ccagagaagg ggctggagtg ggtcgcatac attagtagtg gcagtagtac catctactat | 180 |
| gcagacacag tgaagggccg attcaccatc tccagagaca atcccaagaa caccctgttc | 240 |
| ctgcaaatga ccagtctaag gtctgaggac acggccatgt attactgtgc aagagattac | 300 |
| tacggtatgg actactgggg tcaaggaacc tcagtcaccg tctcctca | 348 |

<210> SEQ ID NO 118
<211> LENGTH: 116
<212> TYPE: PRT
<213> ORGANISM: Mus musculus

<400> SEQUENCE: 118

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Asp Tyr Tyr Gly Met Asp Tyr Trp Gly Gln Gly Thr Ser Val
            100                 105                 110

Thr Val Ser Ser
        115

<210> SEQ ID NO 119
<211> LENGTH: 336
<212> TYPE: DNA
<213> ORGANISM: Mus musculus

<400> SEQUENCE: 119

| | | |
|---|---|---|
| gatgttgtga tgacccaaac tccactctcc ctgcctgtca gtcttggaga tcaagcctcc | 60 |
| atctcttgca gatctagtca gagccttgta cacagtaatg gaaacaccta tttacattgg | 120 |
| tacctgcaga agccaggcca gtctccaaag ctcctgatct acaaagtttc caaccgattt | 180 |
| tctggggtcc cagacaggtt cagtggcagt ggatcaggga cagatttcac actcaagatc | 240 |
| agcagagtgg aggctgagga tctgggagtt tatttctgct ctcaaagtac acatgttccg | 300 |
| ctcacgttcg gtgctgggac caagctggag ctgaaa | 336 |

<210> SEQ ID NO 120
<211> LENGTH: 112
<212> TYPE: PRT
<213> ORGANISM: Mus musculus

<400> SEQUENCE: 120

Asp Val Val Met Thr Gln Thr Pro Leu Ser Leu Pro Val Ser Leu Gly

```
                1               5               10              15
Asp Gln Ala Ser Ile Ser Cys Arg Ser Ser Gln Ser Leu Val His Ser
                20              25              30

Asn Gly Asn Thr Tyr Leu His Trp Tyr Leu Gln Lys Pro Gly Gln Ser
                35              40              45

Pro Lys Leu Leu Ile Tyr Lys Val Ser Asn Arg Phe Ser Gly Val Pro
                50              55              60

Asp Arg Phe Ser Gly Ser Gly Ser Gly Thr Asp Phe Thr Leu Lys Ile
65              70              75              80

Ser Arg Val Glu Ala Glu Asp Leu Gly Val Tyr Phe Cys Ser Gln Ser
                85              90              95

Thr His Val Pro Leu Thr Phe Gly Ala Gly Thr Lys Leu Glu Leu Lys
                100             105             110
```

<210> SEQ ID NO 121
<211> LENGTH: 57
<212> TYPE: DNA
<213> ORGANISM: Mus musculus

<400> SEQUENCE: 121
atgaacaggc ttacttcctc attgctgctg ctgattgtcc ctgcatatgt cctgtcc         57

<210> SEQ ID NO 122
<211> LENGTH: 19
<212> TYPE: PRT
<213> ORGANISM: Mus musculus

<400> SEQUENCE: 122

```
Met Asn Arg Leu Thr Ser Ser Leu Leu Leu Ile Val Pro Ala Tyr
1               5               10              15

Val Leu Ser
```

<210> SEQ ID NO 123
<211> LENGTH: 57
<212> TYPE: DNA
<213> ORGANISM: Mus musculus

<400> SEQUENCE: 123
atggacaggc ttacttcttc attcctgctg ctgattgtcc ctgcatatgt cttgtcc         57

<210> SEQ ID NO 124
<211> LENGTH: 19
<212> TYPE: PRT
<213> ORGANISM: Mus musculus

<400> SEQUENCE: 124

```
Met Asp Arg Leu Thr Ser Ser Phe Leu Leu Ile Val Pro Ala Tyr
1               5               10              15

Val Leu Ser
```

<210> SEQ ID NO 125
<211> LENGTH: 57
<212> TYPE: DNA
<213> ORGANISM: Mus musculus

<400> SEQUENCE: 125
atggactcca ggctcaattt agtttttcctt gtccttattt taaaaggtgt ccagtgt         57

<210> SEQ ID NO 126
<211> LENGTH: 19
<212> TYPE: PRT

<213> ORGANISM: Mus musculus

<400> SEQUENCE: 126

Met Asp Ser Arg Leu Asn Leu Val Phe Leu Val Leu Ile Leu Lys Gly
1               5                   10                  15

Val Gln Cys

<210> SEQ ID NO 127
<211> LENGTH: 57
<212> TYPE: DNA
<213> ORGANISM: Mus musculus

<400> SEQUENCE: 127
atgaacttgg ggctcagctt gattttcctt gtccttgttt taaaaggtgt ccagtgt     57

<210> SEQ ID NO 128
<211> LENGTH: 19
<212> TYPE: PRT
<213> ORGANISM: Mus musculus

<400> SEQUENCE: 128

Met Asn Leu Gly Leu Ser Leu Ile Phe Leu Val Leu Val Leu Lys Gly
1               5                   10                  15

Val Gln Cys

<210> SEQ ID NO 129
<211> LENGTH: 57
<212> TYPE: DNA
<213> ORGANISM: Mus musculus

<400> SEQUENCE: 129
atgaagttgc ctgttaggct gttggtgctg atgttctgga ttcctgcttc cagcagt     57

<210> SEQ ID NO 130
<211> LENGTH: 19
<212> TYPE: PRT
<213> ORGANISM: Mus musculus

<400> SEQUENCE: 130

Met Lys Leu Pro Val Arg Leu Leu Val Leu Met Phe Trp Ile Pro Ala
1               5                   10                  15

Ser Ser Ser

<210> SEQ ID NO 131
<211> LENGTH: 22
<212> TYPE: DNA
<213> ORGANISM: Artificial Sequence
<220> FEATURE:
<223> OTHER INFORMATION: a primer sequence

<400> SEQUENCE: 131
aaggcttaca accacaatcc ct                                           22

<210> SEQ ID NO 132
<211> LENGTH: 19
<212> TYPE: DNA
<213> ORGANISM: Artificial Sequence
<220> FEATURE:
<223> OTHER INFORMATION: a primer sequence

<400> SEQUENCE: 132
tgctgggcat ttgcatgga                                               19

<210> SEQ ID NO 133
<211> LENGTH: 19
<212> TYPE: DNA
<213> ORGANISM: Artificial Sequence
<220> FEATURE:
<223> OTHER INFORMATION: a primer sequence

<400> SEQUENCE: 133
tgggcatttg tgacactcc                                                    19

<210> SEQ ID NO 134
<211> LENGTH: 21
<212> TYPE: DNA
<213> ORGANISM: Artificial Sequence
<220> FEATURE:
<223> OTHER INFORMATION: a primer sequence

<400> SEQUENCE: 134
actgggcttg ggtattctag g                                                 21

<210> SEQ ID NO 135
<211> LENGTH: 31
<212> TYPE: DNA
<213> ORGANISM: Artificial Sequence
<220> FEATURE:
<223> OTHER INFORMATION: a primer sequence

<400> SEQUENCE: 135
gtccaactgt tcaggacgcc attttgtcgt t                                      31

<210> SEQ ID NO 136
<211> LENGTH: 27
<212> TYPE: DNA
<213> ORGANISM: Artificial Sequence
<220> FEATURE:
<223> OTHER INFORMATION: a primer sequence

<400> SEQUENCE: 136
tccacagtgt gaccttcatg agtgacc                                           27

<210> SEQ ID NO 137
<211> LENGTH: 19
<212> TYPE: DNA
<213> ORGANISM: Artificial Sequence
<220> FEATURE:
<223> OTHER INFORMATION: a primer sequence

<400> SEQUENCE: 137
acagggatcc agagttcca                                                    19

<210> SEQ ID NO 138
<211> LENGTH: 18
<212> TYPE: DNA
<213> ORGANISM: Artificial Sequence
<220> FEATURE:
<223> OTHER INFORMATION: a primer sequence

<400> SEQUENCE: 138
taactgctca ctggatgg                                                     18

<210> SEQ ID NO 139
<211> LENGTH: 24
<212> TYPE: DNA
<213> ORGANISM: Artificial Sequence
<220> FEATURE:
<223> OTHER INFORMATION: a primer sequence

<400> SEQUENCE: 139

```
<210> SEQ ID NO 140
<211> LENGTH: 30
<212> TYPE: DNA
<213> ORGANISM: Artificial Sequence
<220> FEATURE:
<223> OTHER INFORMATION: a primer sequence

<400> SEQUENCE: 140
ggccacgcgt cgactagtac gggggggggg                                    30

<210> SEQ ID NO 141
<211> LENGTH: 20
<212> TYPE: DNA
<213> ORGANISM: Artificial Sequence
<220> FEATURE:
<223> OTHER INFORMATION: a primer sequence

<400> SEQUENCE: 141
ggccacgcgt cgactagtac                                               20

<210> SEQ ID NO 142
<211> LENGTH: 24
<212> TYPE: DNA
<213> ORGANISM: Artificial Sequence
<220> FEATURE:
<223> OTHER INFORMATION: a primer sequence

<400> SEQUENCE: 142
cgccagggtt ttcccagtca cgac                                          24

<210> SEQ ID NO 143
<211> LENGTH: 22
<212> TYPE: DNA
<213> ORGANISM: Artificial Sequence
<220> FEATURE:
<223> OTHER INFORMATION: a primer sequence

<400> SEQUENCE: 143
tcacacagga aacagctatg ac                                            22
```